(12) United States Patent
Berka et al.

(10) Patent No.: US 7,601,499 B2
(45) Date of Patent: Oct. 13, 2009

US007601499B2

(54) PAIRED END SEQUENCING

(75) Inventors: Jan Berka, Guilford, CT (US); Zhoutao Chen, Milford, CT (US); Michael Egholm, Woodbridge, CT (US); Brian C. Godwin, North Haven, CT (US); Stephen Kyle Hutchison, Branford, CT (US); John Harris Leamon, Guilford, CT (US); Gary James Sarkis, Guilford, CT (US); Jan Fredrik Simons, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 0 days.

(21) Appl. No.: 11/448,462

(22) Filed: Jun. 6, 2006

(65) Prior Publication Data

US 2006/0292611 A1 Dec. 28, 2006

Related U.S. Application Data

(60) Provisional application No. 60/717,964, filed on Sep. 16, 2005, provisional application No. 60/771,818, filed on Feb. 8, 2006, provisional application No. 60/688,042, filed on Jun. 6, 2005.

(51) Int. Cl.
*C12Q 1/68* (2006.01)
*C12P 19/34* (2006.01)
*C07H 21/04* (2006.01)

(52) U.S. Cl. .................... 435/6; 435/91.2; 536/23.1

(58) Field of Classification Search ............. None
See application file for complete search history.

(56) References Cited

U.S. PATENT DOCUMENTS

| | | | |
|---|---|---|---|
| 5,714,320 A | 2/1998 | Kool | |
| 5,989,892 A | 11/1999 | Nishimaki et al. | |
| 6,459,103 B1 | 10/2002 | Liu et al. | |
| 6,489,103 B1 | 12/2002 | Griffiths et al. | 435/6 |
| 6,498,023 B1 * | 12/2002 | Abarzua | 435/91.2 |
| 6,815,167 B2 * | 11/2004 | Crothers et al. | 435/6 |
| 2004/0002090 A1 * | 1/2004 | Mayer et al. | 435/6 |
| 2005/0130173 A1 | 6/2005 | Leamon et al. | |
| 2006/0024681 A1 * | 2/2006 | Smith et al. | 435/6 |

FOREIGN PATENT DOCUMENTS

| | | |
|---|---|---|
| WO | WO 03/012119 | 2/2003 |
| WO | WO 03/074734 | 9/2003 |
| WO | WO 2005/042781 | 5/2005 |
| WO | WO 06/003721 | 1/2006 |
| WO | WO 07/145612 | 12/2007 |

OTHER PUBLICATIONS

Bobovnikovna et al. Insert selection by BamHI methyltransferase protection in P1 phage-based cloning. Gene (1996) 170: 39- 44.*
Watson et al. Cloning and assembly of PCR products using modified primers and DNA repair enzymes. Biotechniques (1997) 23(5): 858-860, 862, 864.*
Smith, M.W. et al, (1994) Nature Genetics 7: 40-47.
Goryshin, I.Y. and Reznikoff, W.S., (1998) J. Biol. Chem. 273(13): 7367-7374.
Reznikoff, W.S. et al, (2004) Methods Mol. Biol. 260: 83-96.
Colegio, O.R. et al, (2001) J. Bacteriol. 183(7): 2384-2388.
Pelicic, V. et al, (2000) J. Bacteriol. 182: 5391-5398.
Yao, M. And Kow, Y.W. (1995) J. Biol. Chem. 270(48): 28609-28616.
Yao, M. And Kow, Y.W. (1994) J. Biol. Chem. 269(50): 31390-31396.
Yao, M. et al, (1994) Ann. NY Acad. Sci. 726: 315-316.
U.S. Appl. No. 60/476,602, filed Jun. 6, 2003, Costa, et al.
U.S. Appl. No. 60/476,504, filed Jun. 6, 2003, Berka, et al.
U.S. Appl. No. 60/443,471, filed Jan. 29, 2003, Weiner, et al.
U.S. Appl. No. 60/476,313, filed Jun. 6, 2003, Chen, et al.
U.S. Appl. No. 60/476,592, filed Jun. 6, 2003, Leamon, et al.
U.S. Appl. No. 60/465,071, filed Apr. 23, 2003, Lohman, K.L.
U.S. Appl. No. 60/497,985, filed Aug. 25, 2003, Leamon, et al.
Yao, M. et al, (1994) J. Biol. Chem. 269(23): 16260-16268.
Watkins, N. E. and SantaLucia, J. (2005) Nucleic Acids Res. 33(19): 6258-6267.
DeAngelis, M.M. et al, (1995) Nucleic Acids Res. 23: 4742-4743.
Link, D.R. et al, (2006) Angew. Chem. Int. Ed. 45: 2556-2560.
Griffiths, A.D. and Tawfik D.S. (2003) EMBO J. 22: 24-35.
Metzker, M.L. et al. (2005) Genome Res. 15(12): 1767-1776.
Ghadessy et al. (2001), PNAS, 98:4552-4557.
International Search Report for PCT/US2006/022206 mailed Jun. 22, 2007.

* cited by examiner

*Primary Examiner*—Gary Benzion
*Assistant Examiner*—Angela Bertagna
(74) *Attorney, Agent, or Firm*—Ivor R. Elrifi, Esq.; Mintz Levin Cohn Ferris Glovsky and Popeo PC

(57) ABSTRACT

The present invention provides for a method of preparing a target nucleic acid fragments to produce a smaller nucleic acid which comprises the two ends of the target nucleic acid. Specifically, the invention provides cloning and DNA manipulation strategies to isolate the two ends of a large target nucleic acid into a single small DNA construct for rapid cloning, sequencing, or amplification.

53 Claims, 46 Drawing Sheets
(41 of 46 Drawing Sheet(s) Filed in Color)

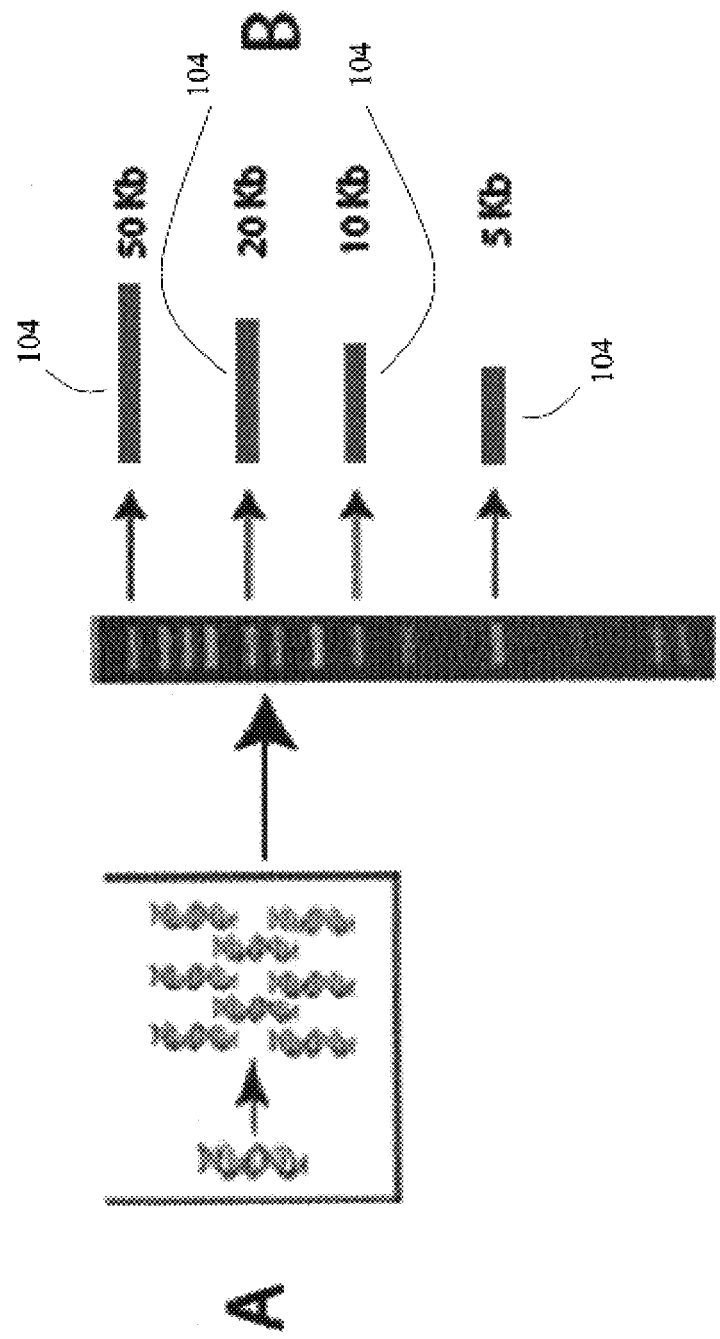
Figure 1 A, B

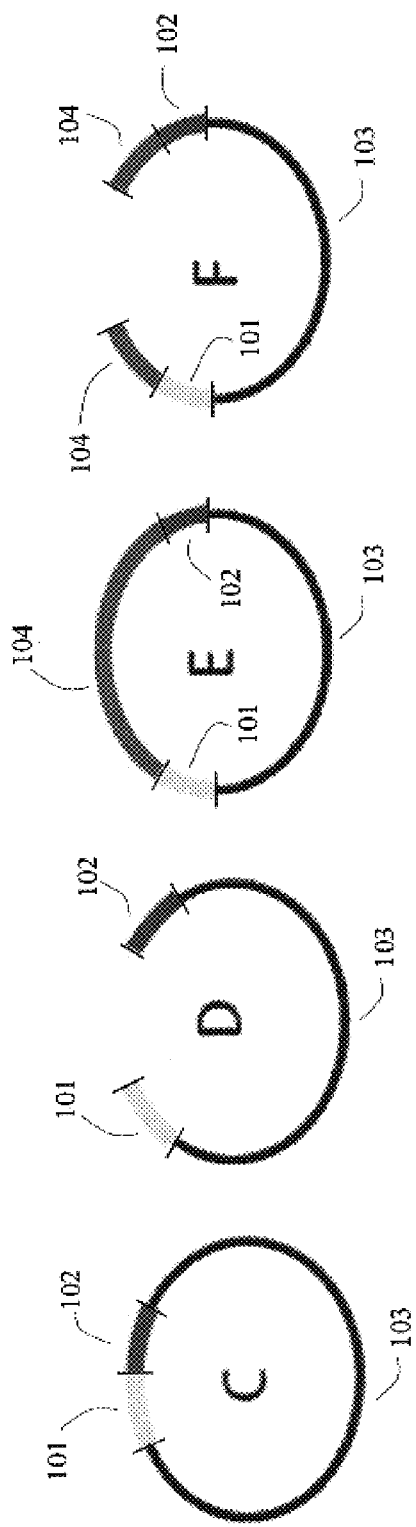
Figure 1 C-F

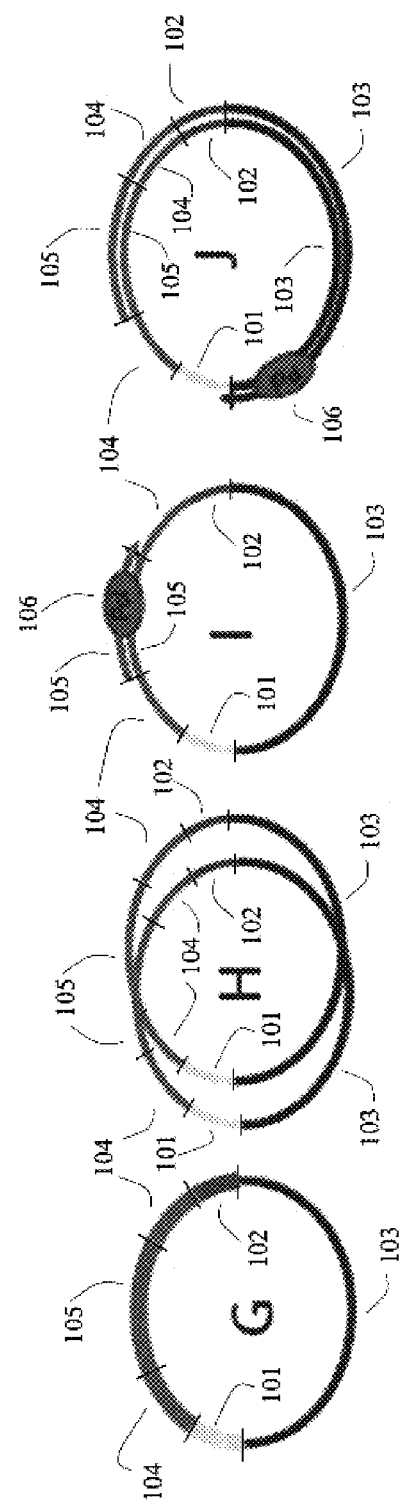
Figure 1 G-J

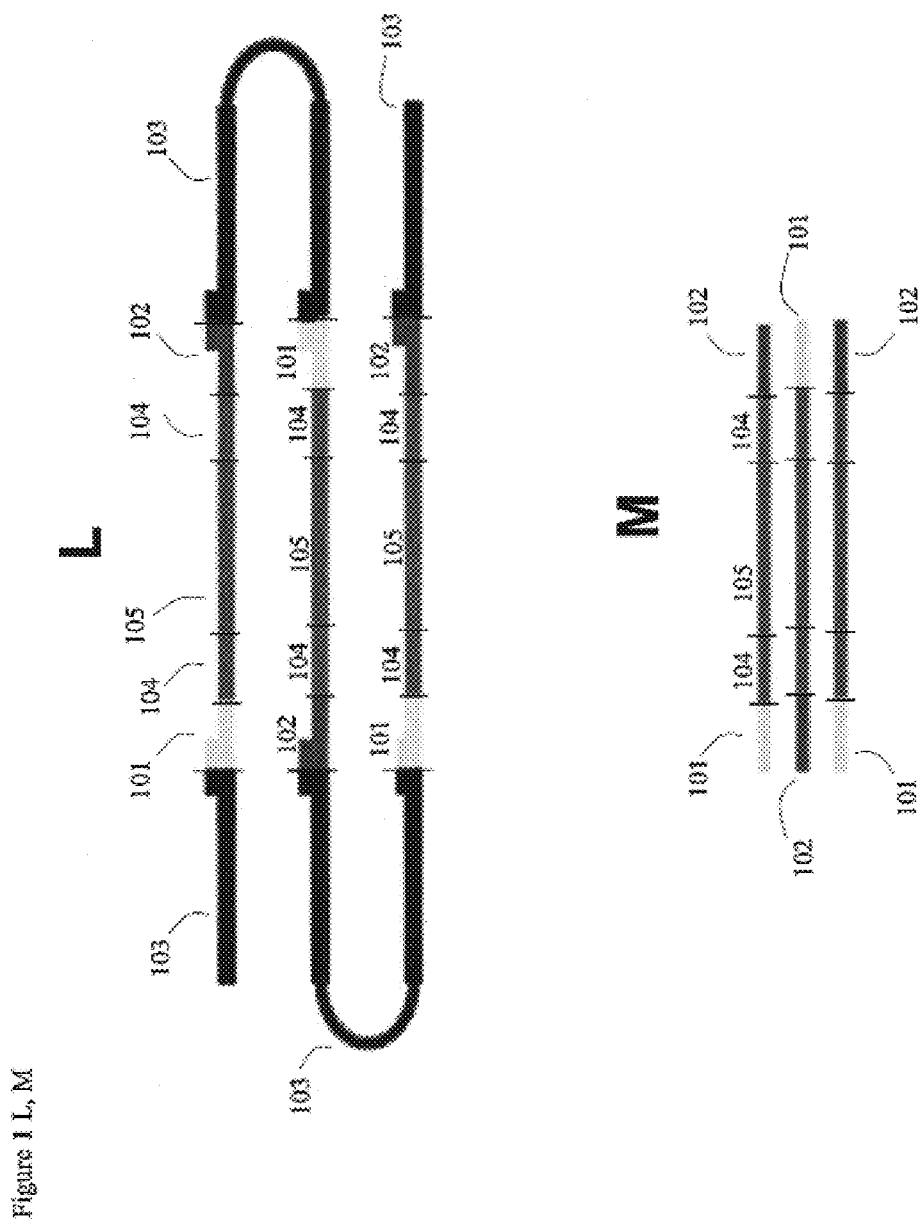
Figure 1 L, M

Figure 3

A  Paired-End Capture Fragment:

```
Product:  MMP7A            UA3              NotI        UA3B            MMP2B           (SEQ ID NO:1)
          CTGAGACACGCAACAGGGGATAGGCAAGGCACACAGGGgcggccgcCCATCTCATCCCTGCGTGTCCCATCTGTTCCCTCCCTGTCTCAG  (96 bp)

Oligo1:   CTGAGACACGCAACAGGGGATAGGCAAGGCACACAGGG                                                       (SEQ ID NO:2)

Oligo2:              TAGGCAAGGCACACAGGGGATAGGgcggccgcCCATC                                             (SEQ ID NO:3)

Oligo3:                                ATAGGgcggccgcCCATCTCATCCCTGCGTGTCCAT                            (SEQ ID NO:4)

Oligo4:                                              CATCCCTGCGTGTCCCATCTGTTCCCTCCCTGTCTCAG            (SEQ ID NO:5)
```

Paired-End Capture Fragment (type II, MmeI):

```
          MmeI         MMP7A            UA3              NotI        UA3B            MMP2B          MmeI
Product:  gtccaCTGAGACACGCAACAGGGGATAGGCAAGGCACACAGGGgcggccgcCCATCTCATCCCTGCGTGTCCCATCTGTTCCCTCCCTGTCTCAGtccgac   (108 bp)
                                                                                                               (SEQ ID NO:6)
```

B  Short Adaptor Paired-End Capture Fragment:

```
          SAD1B            NotI       SAD1A
Product:  CTGAGCGGGCTGGCAAGGCgcccGCCTCCCTGCGCCATCAG       (42 bp)  (SEQ ID NO:7)
```

Short Adaptor Paired-End Capture Fragment (type II, MmeI):

```
          MmeI    SAD1B             NotI       SAD1A         MmeI
Product:  gtccaCTGAGCGGGCTGGCAAGGCggccGCCTCCCTGCGCCATCAGtccgac    (54 bp)   (SEQ ID NO:8)
```

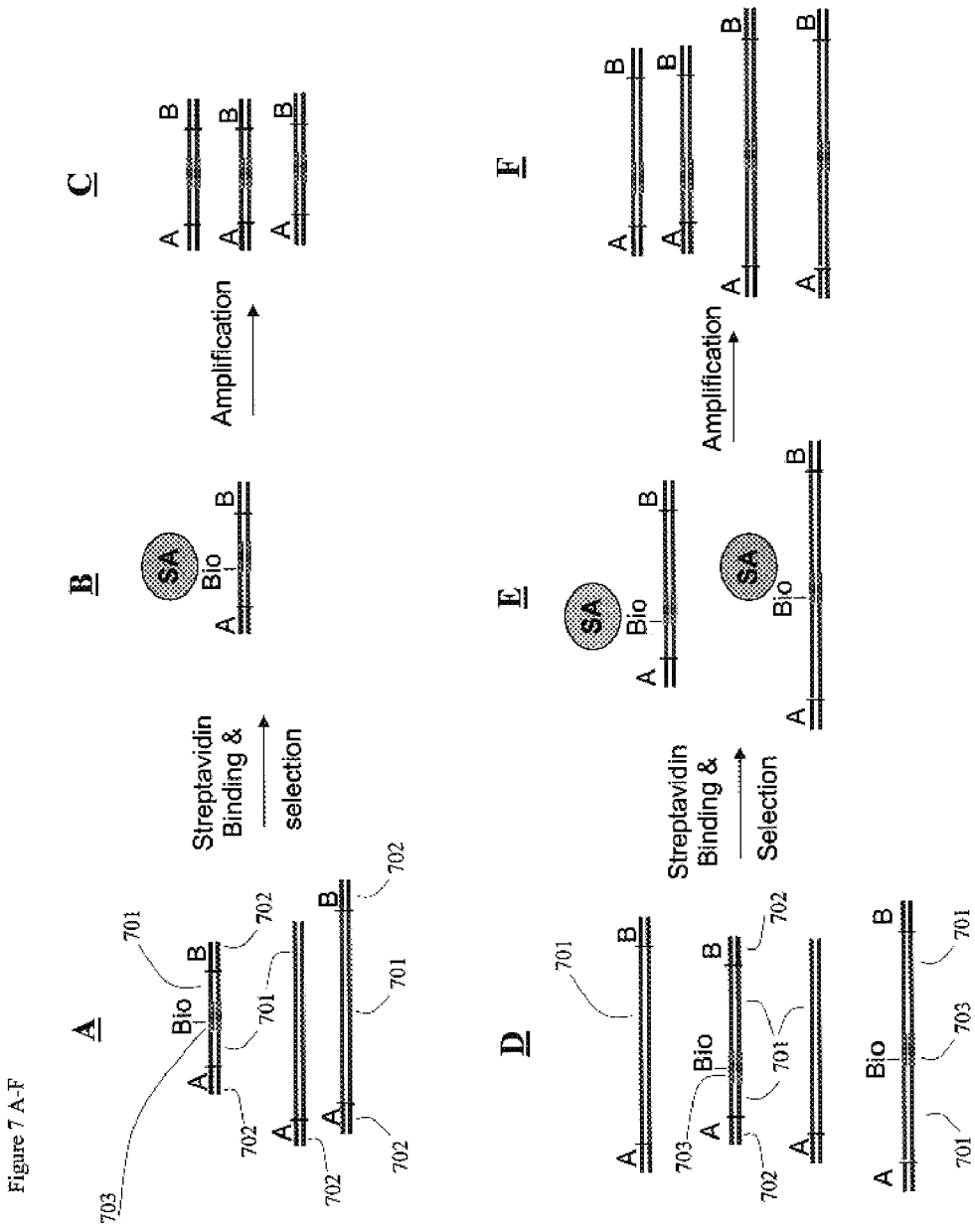

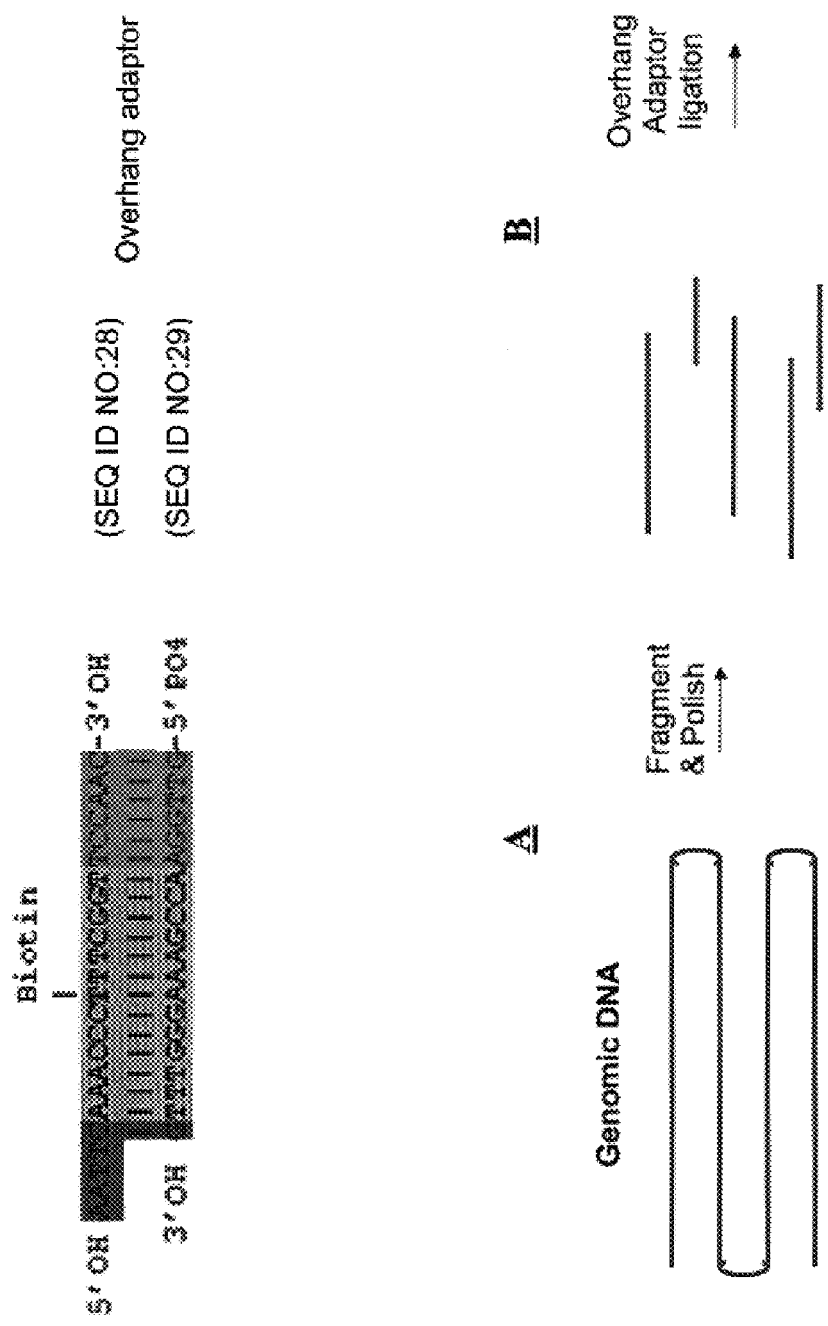
Figure 8 A, B

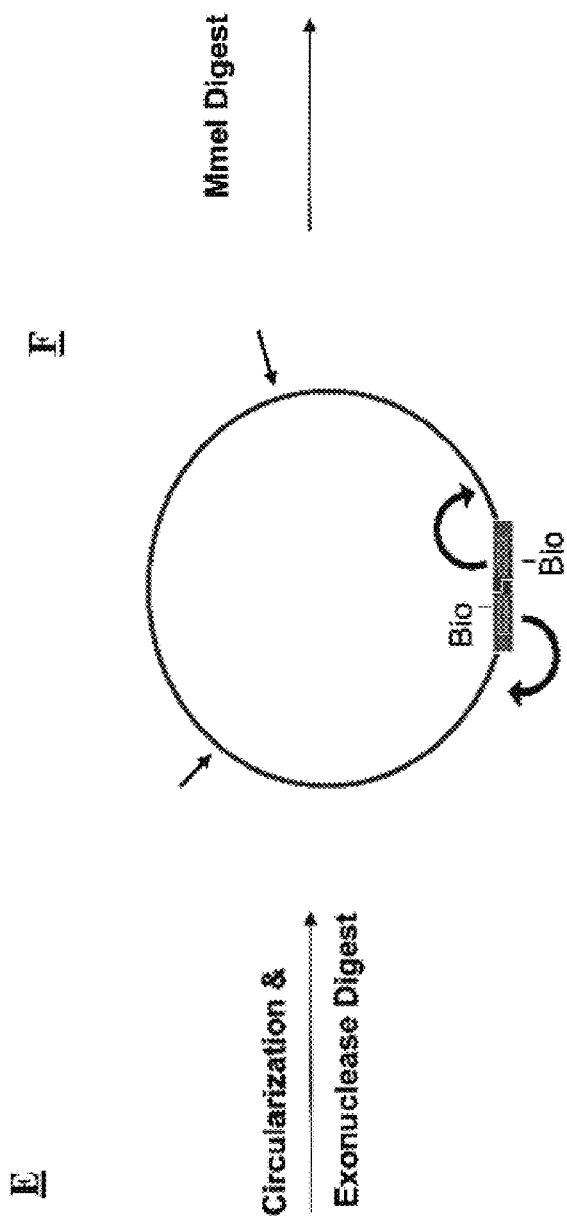

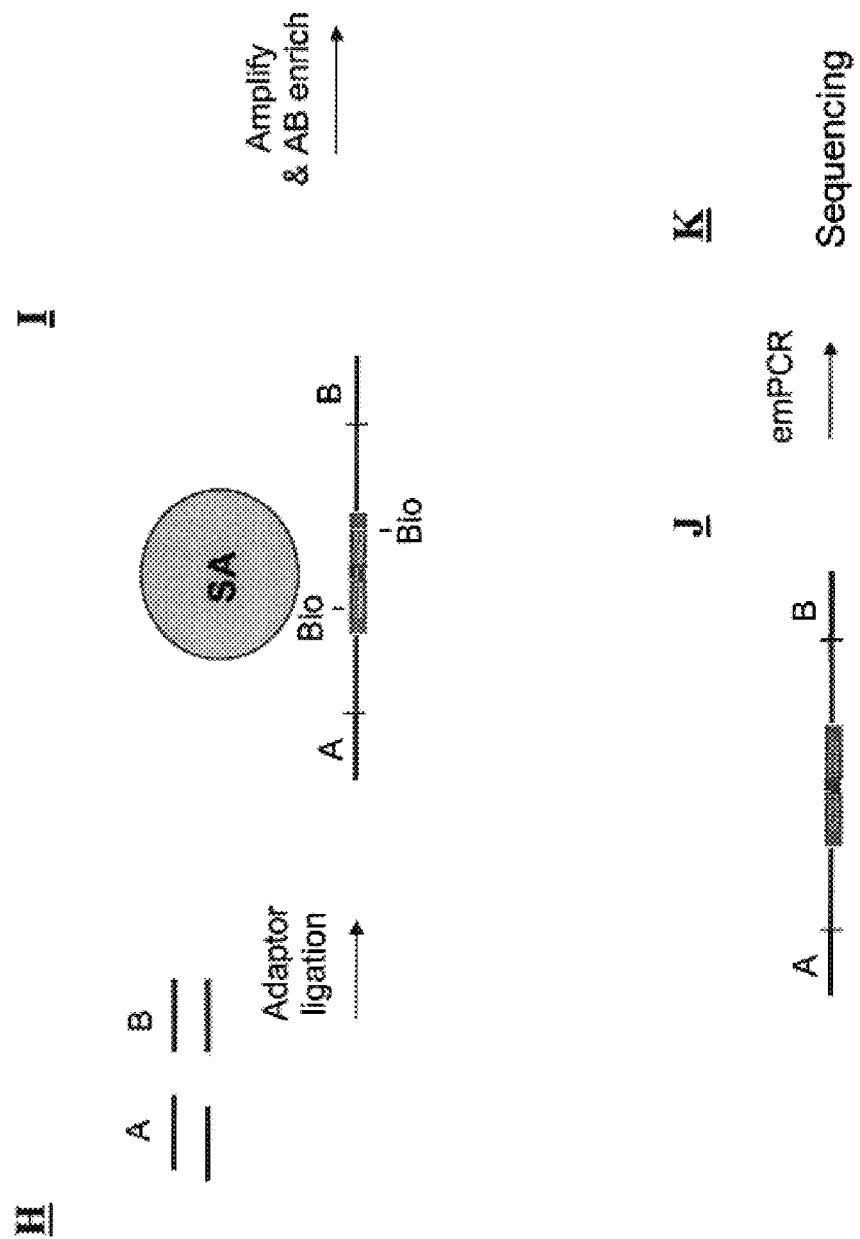
Figure 8 H-K

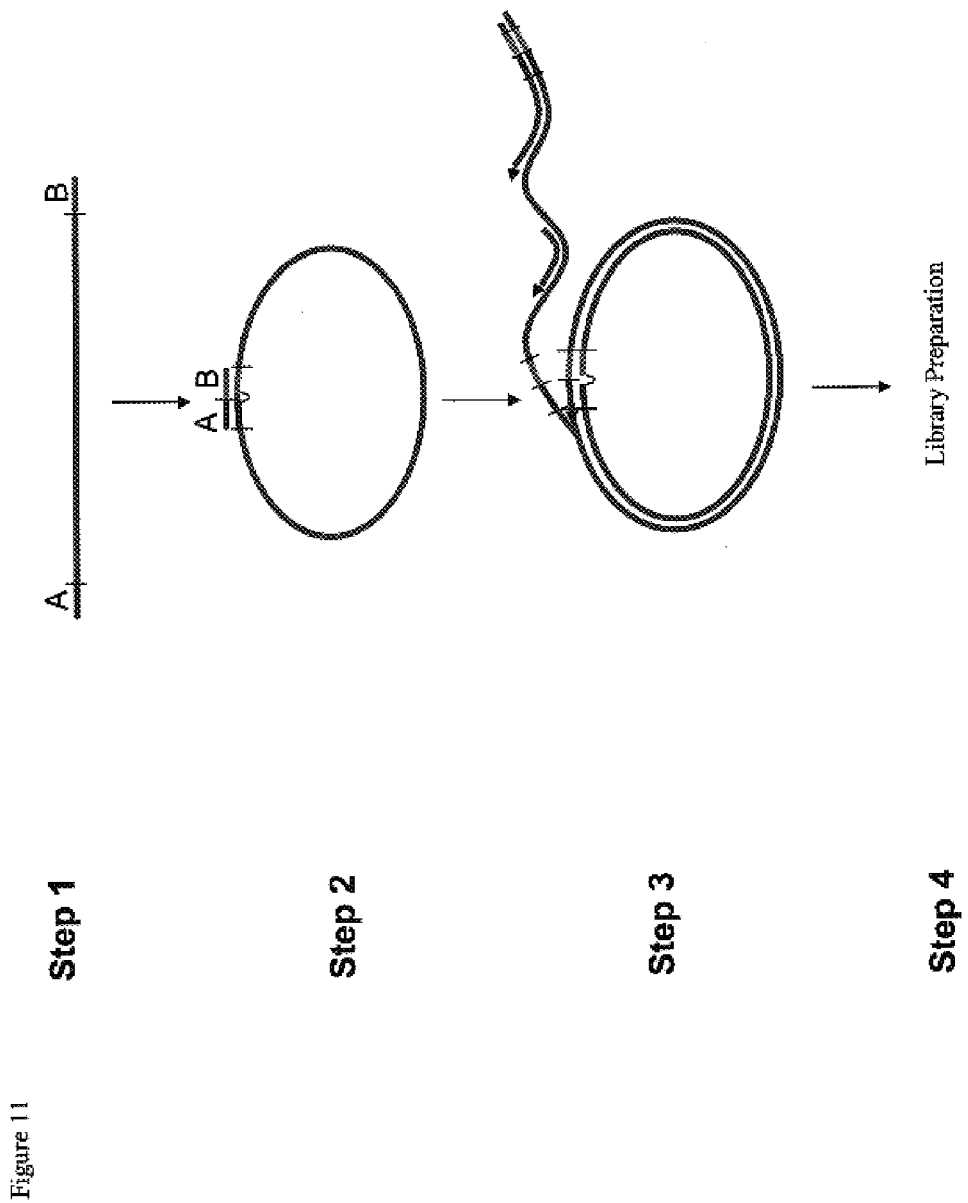

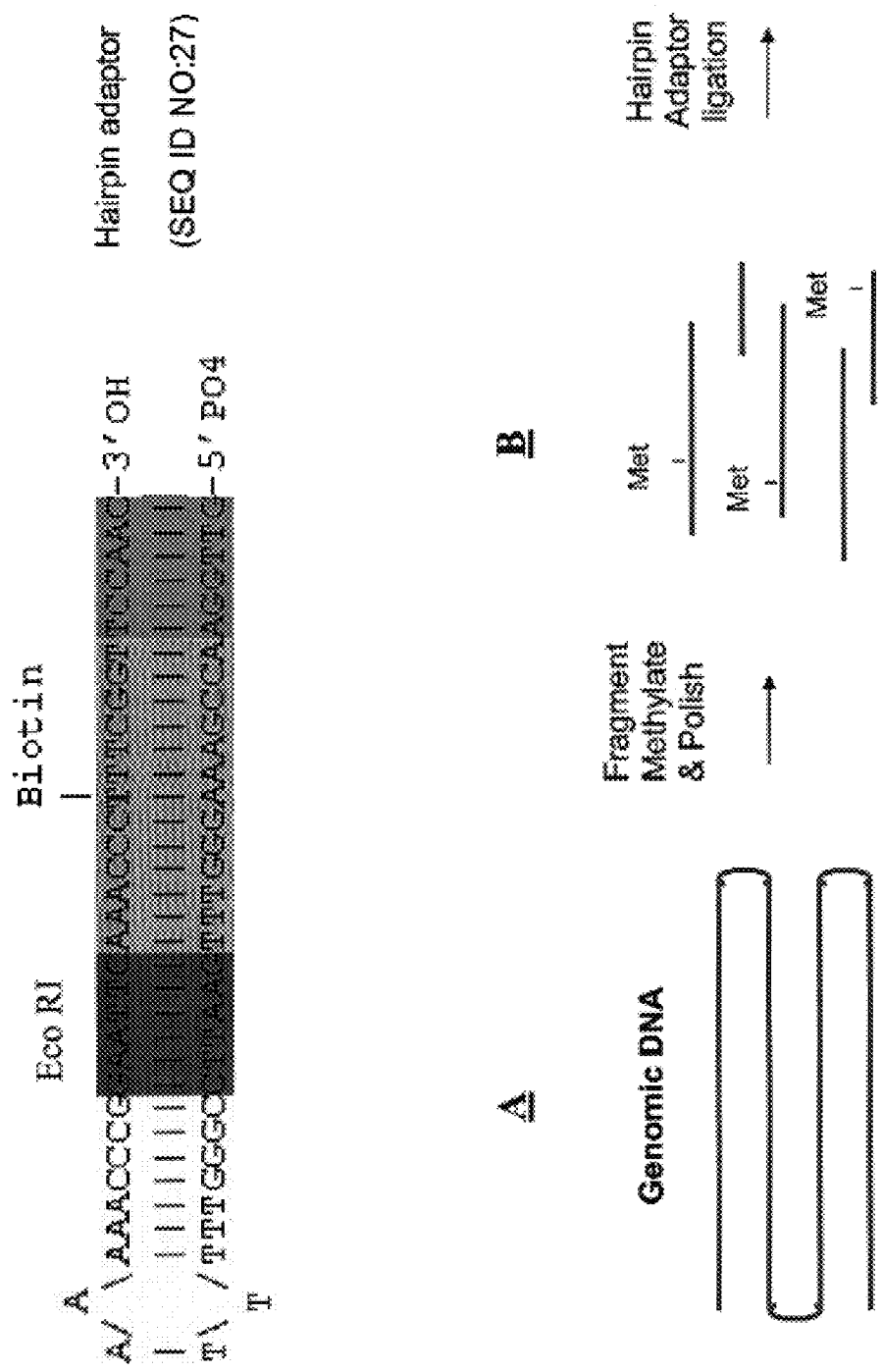
Figure 12 A, B

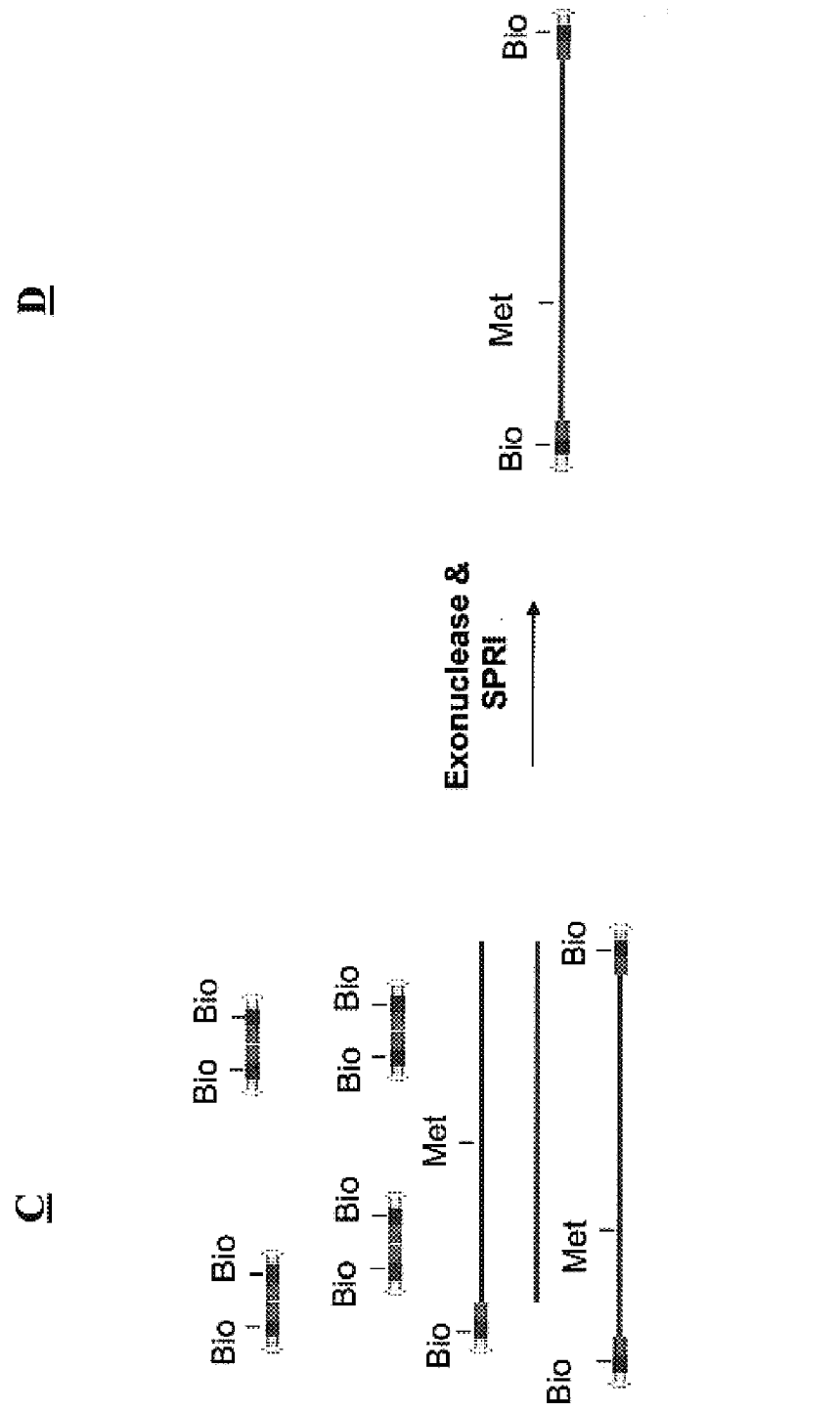
Figure 12 C, D

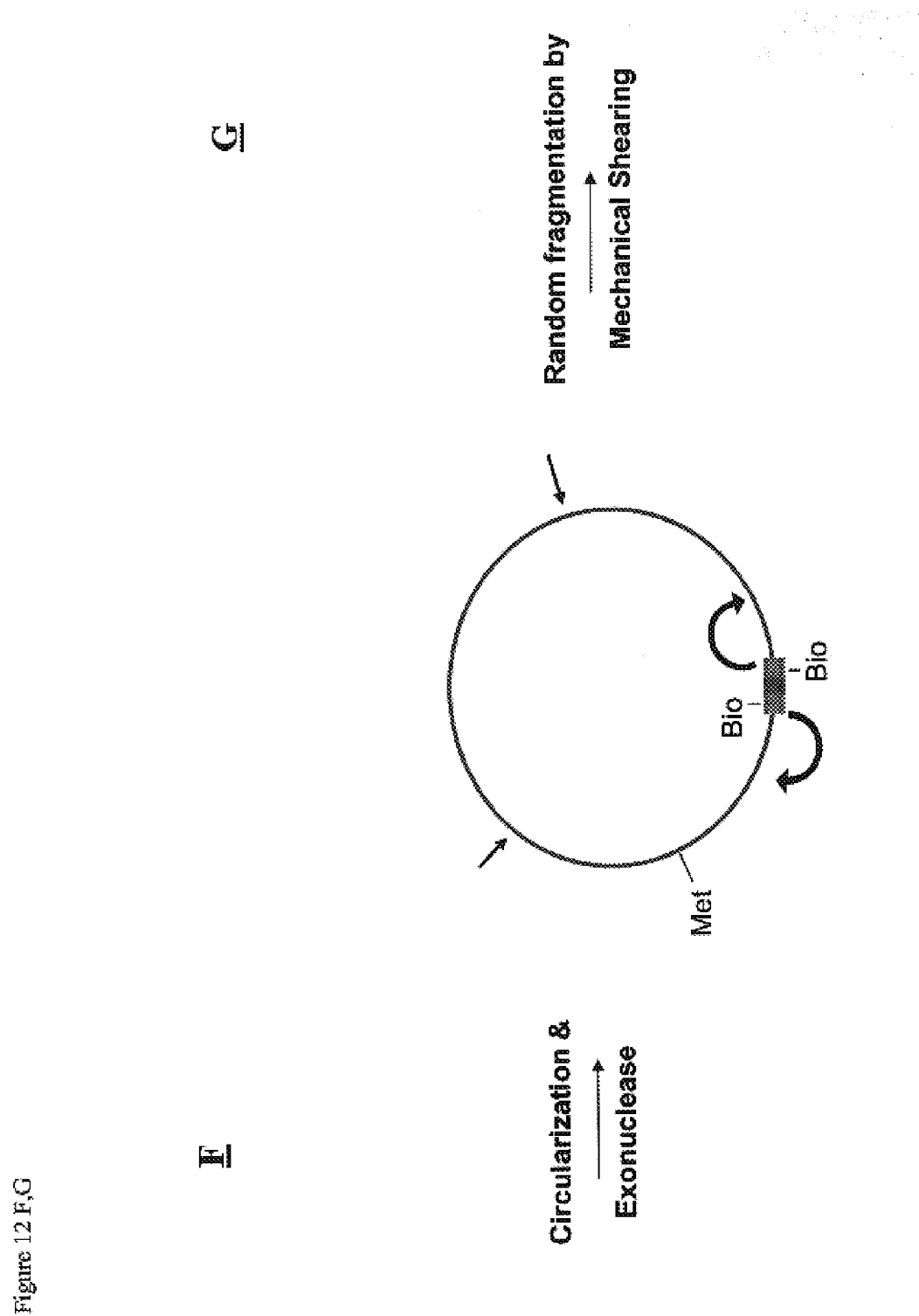
Figure 12 F,G

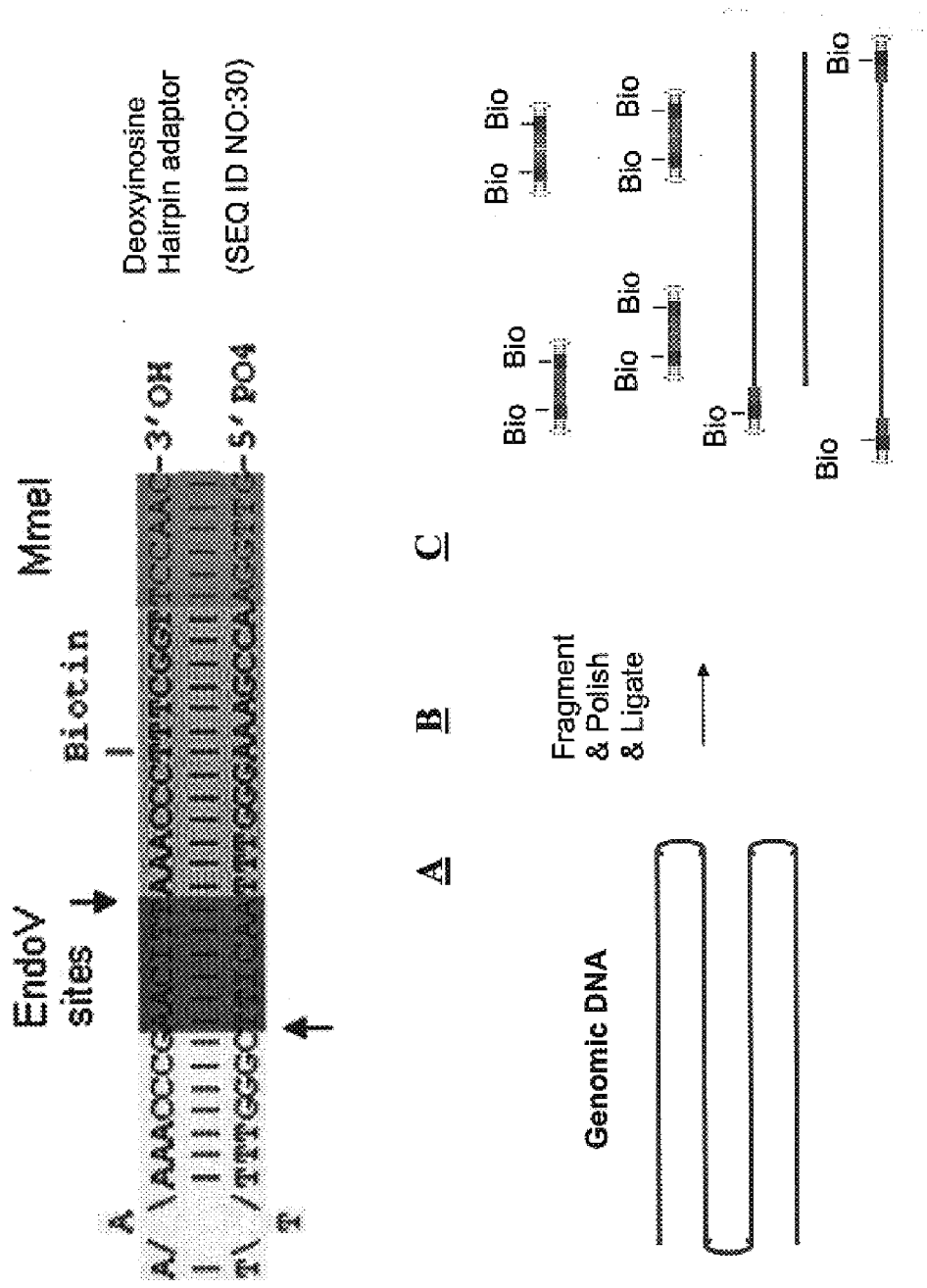
Figure 15 A-C

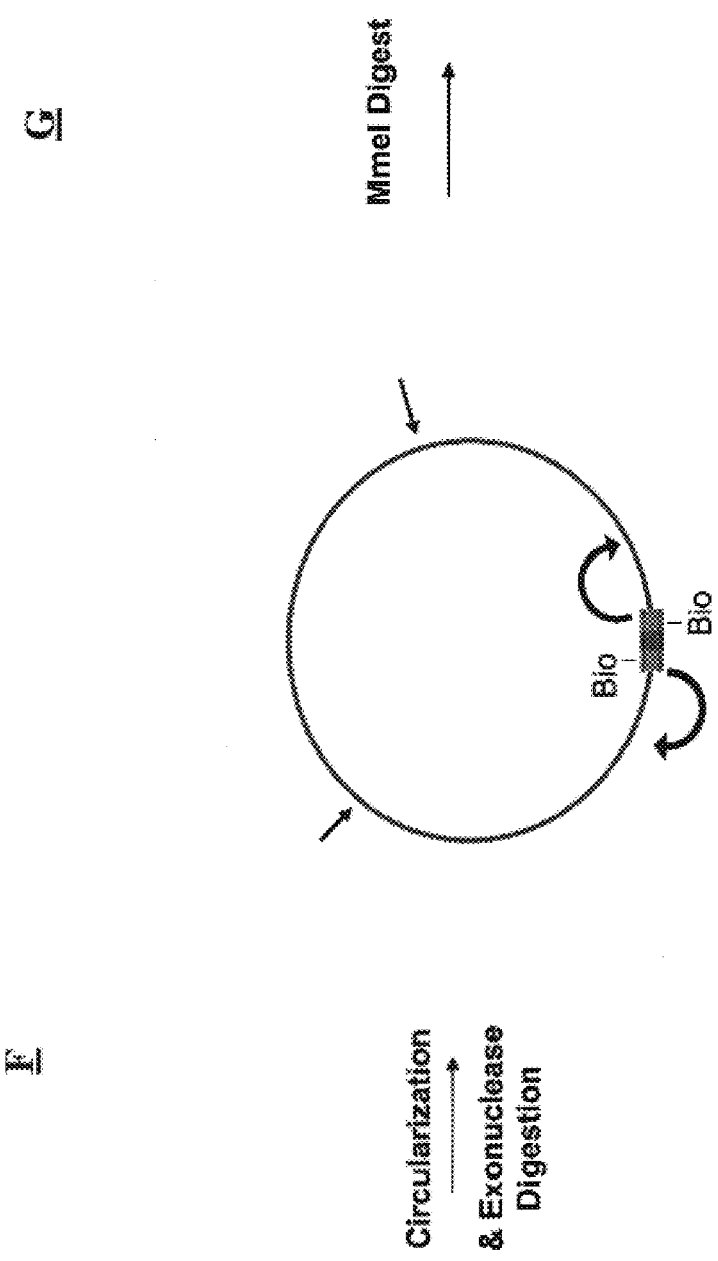
Figure 15 F, G

Hairpin Adaptor:

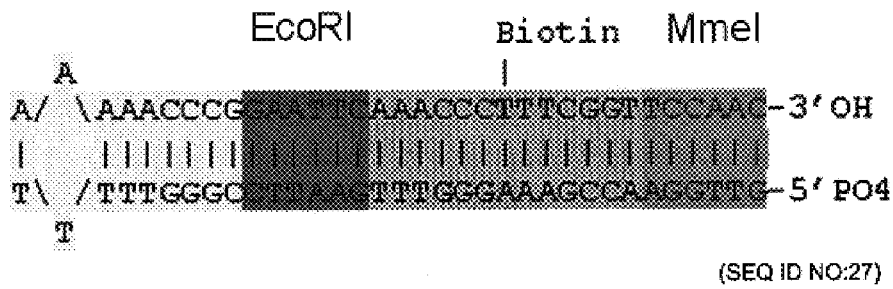

(SEQ ID NO:27)

PO4-5'-GTTGGAACCGAAAGGGTTTGAATTCCGGGTTTTTAAAAACCCGGAATTCAAAC

CC-iBiodT-TTCGGTTCCAAC-3'-OH (SEQ ID NO:27)

B

Paired end adaptor oligonucleotide components, and PCR primers:
(Note: the 5' ends of the polynucleotide sequences listed are *not* phosphorylated)

| Oligonucleotide Name | Nucleotide sequence (5' -> 3') | SEQ ID NO |
|---|---|---|
| A top | GCCTCCCTCGCGCCATCAGNN | 45 |
| A bottom | CTGATGGCGCGAGGG | 46 |
| B top | GCCTTGCCAGCCCGCTCAGNN | 47 |
| B bottom | CTGAGCGGGCTGGCA | 48 |
| F-PCR | Bio-GCCTCCCTCGCGCCA | 49 |
| R-PCR | GCCTTGCCAGCCCGC | 50 | paired end adaptor A:

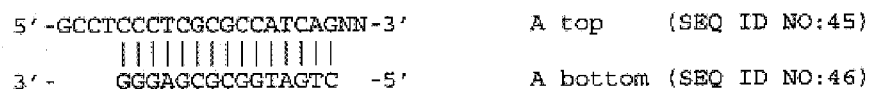

A top    (SEQ ID NO:45)
A bottom (SEQ ID NO:46)

paired end adaptor B:

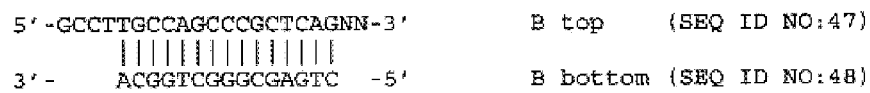

B top    (SEQ ID NO:47)
B bottom (SEQ ID NO:48)

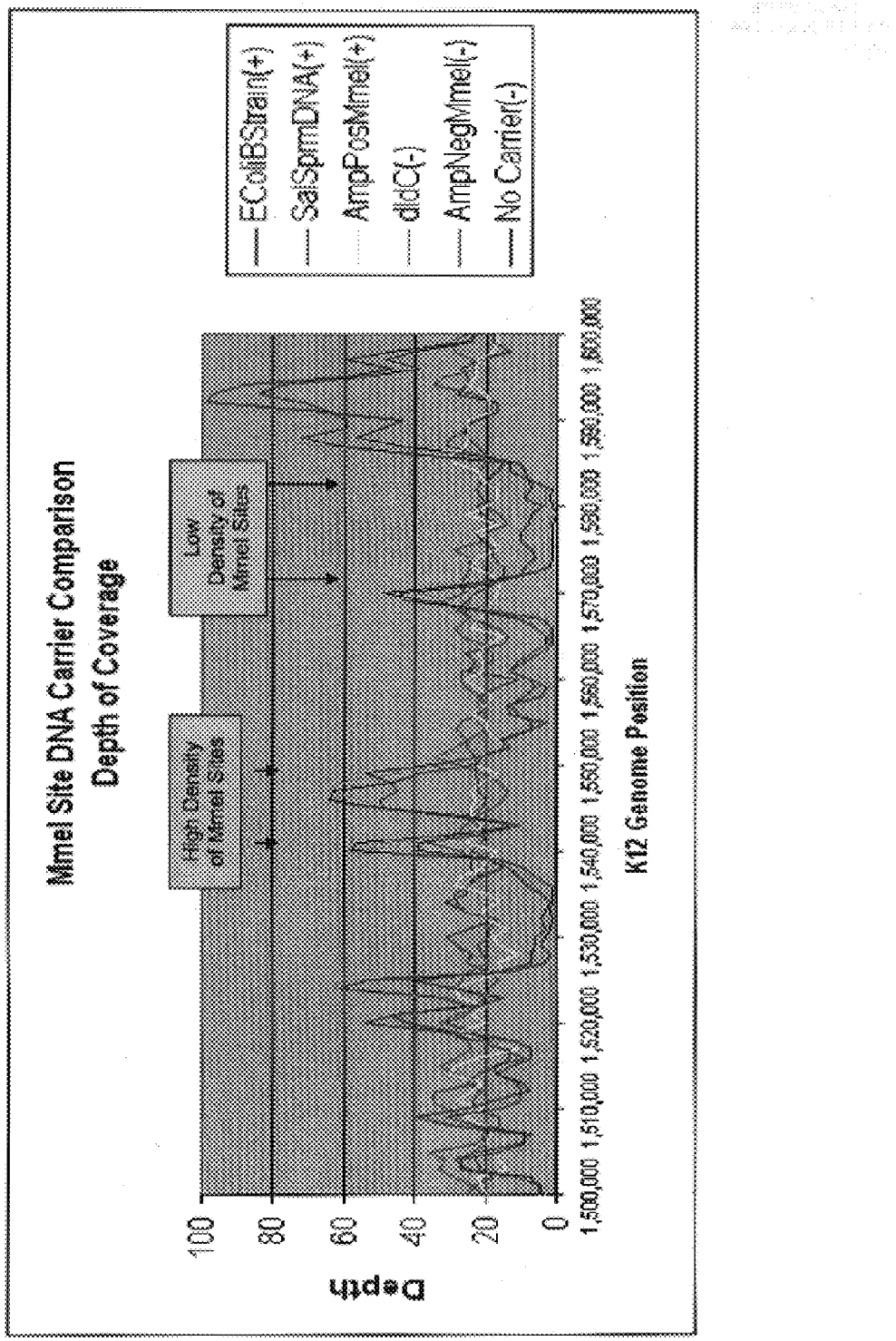

```
                             SEQUENCE LISTING

<160> NUMBER OF SEQ ID NOS: 56

<210> SEQ ID NO 1
<211> LENGTH: 96
<212> TYPE: DNA
<213> ORGANISM: Homo sapiens

<400> SEQUENCE: 1
ctgagacacg caacagggga taggcaaggc acacagggga tagggcggcc gcccatctca      60
tccctgcgtg tcccatctgt tccctccctg tctcag                               96

<210> SEQ ID NO 2
<211> LENGTH: 38
<212> TYPE: DNA
<213> ORGANISM: Homo sapiens

<400> SEQUENCE: 2
ctgagacacg caacagggga taggcaaggc acacaggg                              38

<210> SEQ ID NO 3
<211> LENGTH: 37
<212> TYPE: DNA
<213> ORGANISM: Homo sapiens

<400> SEQUENCE: 3
taggcaaggc acacagggga tagggcggcc gcccatc                               37

<210> SEQ ID NO 4
<211> LENGTH: 37
<212> TYPE: DNA
<213> ORGANISM: Homo sapiens

<400> SEQUENCE: 4
atagggcggc cgcccatctc atccctgcgt gtcccat                               37

<210> SEQ ID NO 5
<211> LENGTH: 38
<212> TYPE: DNA
<213> ORGANISM: Homo sapiens

<400> SEQUENCE: 5
catccctgcg tgtcccatct gttccctccc tgtctcag                              38
```

<210> SEQ ID NO 6
<211> LENGTH: 108
<212> TYPE: DNA
<213> ORGANISM: Homo sapiens

<400> SEQUENCE: 6
gttccactga gacacgcaac aggggatagg caaggcacac aggggatagg gcggccgccc    60
atctcatccc tgcgtgtccc atctgttccc tccctgtctc agtccgac                108

<210> SEQ ID NO 7
<211> LENGTH: 42
<212> TYPE: DNA
<213> ORGANISM: Homo sapiens

<400> SEQUENCE: 7
ctgagcgggc tggcaaggcg gccgcctccc tcgcgccatc ag                       42

<210> SEQ ID NO 8
<211> LENGTH: 54
<212> TYPE: DNA
<213> ORGANISM: Homo sapiens

<400> SEQUENCE: 8
gttccactga gcgggctggc aaggcggccg cctccctcgc gccatcagtc cgac          54

<210> SEQ ID NO 9
<211> LENGTH: 56
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Wherein n may be a, c, g or t
<220> FEATURE:
<221> NAME/KEY: misc_feature
<222> LOCATION: (2)..(2)
<223> OTHER INFORMATION: Wherein n may be a, c, g or t
<220> FEATURE:
<221> NAME/KEY: misc_feature
<222> LOCATION: (3)..(3)
<223> OTHER INFORMATION: Wherein n may be a, c, g or t
<220> FEATURE:
<221> NAME/KEY: misc_feature
<222> LOCATION: (4)..(4)
<223> OTHER INFORMATION: Wherein n may be a, c, g or t
<220> FEATURE:
<221> NAME/KEY: misc_feature
<222> LOCATION: (5)..(5)
<223> OTHER INFORMATION: Wherein n may be a, c, g or t
<220> FEATURE:
<221> NAME/KEY: misc_feature
<222> LOCATION: (6)..(6)
<223> OTHER INFORMATION: Wherein n may be a, c, g or t
<220> FEATURE:
<221> NAME/KEY: misc_feature
<222> LOCATION: (51)..(51)
<223> OTHER INFORMATION: Wherein n may be a, c, g or t
<220> FEATURE:
<221> NAME/KEY: misc_feature
<222> LOCATION: (52)..(52)
<223> OTHER INFORMATION: Wherein n may be a, c, g or t
<220> FEATURE:
<221> NAME/KEY: misc_feature
<222> LOCATION: (53)..(53)
<223> OTHER INFORMATION: Wherein n may be a, c, g or t
<220> FEATURE:
<221> NAME/KEY: misc_feature
<222> LOCATION: (54)..(54)
<223> OTHER INFORMATION: Wherein n may be a, c, g or t
<220> FEATURE:

<221> NAME/KEY: misc_feature
<222> LOCATION: (55)..(55)
<223> OTHER INFORMATION: Wherein n may be a, c, g or t
<220> FEATURE:
<221> NAME/KEY: misc_feature
<222> LOCATION: (56)..(56)
<223> OTHER INFORMATION: Wherein n may be a, c, g or t

<400> SEQUENCE: 9
nnnnnngaat tcctagtacg acaccagtcg atcggatcac atcgaagctt nnnnnn        56

<210> SEQ ID NO 10
<211> LENGTH: 56
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Wherein n may be a, c, g or t
<220> FEATURE:
<221> NAME/KEY: misc_feature
<222> LOCATION: (2)..(2)
<223> OTHER INFORMATION: Wherein n may be a, c, g or t
<220> FEATURE:
<221> NAME/KEY: misc_feature
<222> LOCATION: (3)..(3)
<223> OTHER INFORMATION: Wherein n may be a, c, g or t
<220> FEATURE:
<221> NAME/KEY: misc_feature
<222> LOCATION: (4)..(4)
<223> OTHER INFORMATION: Wherein n may be a, c, g or t
<220> FEATURE:
<221> NAME/KEY: misc_feature
<222> LOCATION: (5)..(5)
<223> OTHER INFORMATION: Wherein n may be a, c, g or t
<220> FEATURE:
<221> NAME/KEY: misc_feature
<222> LOCATION: (6)..(6)
<223> OTHER INFORMATION: Wherein n may be a, c, g or t
<220> FEATURE:
<221> NAME/KEY: misc_feature
<222> LOCATION: (51)..(51)
<223> OTHER INFORMATION: Wherein n may be a, c, g or t
<220> FEATURE:
<221> NAME/KEY: misc_feature
<222> LOCATION: (52)..(52)
<223> OTHER INFORMATION: Wherein n may be a, c, g or t
<220> FEATURE:
<221> NAME/KEY: misc_feature
<222> LOCATION: (53)..(53)
<223> OTHER INFORMATION: Wherein n may be a, c, g or t
<220> FEATURE:
<221> NAME/KEY: misc_feature
<222> LOCATION: (54)..(54)
<223> OTHER INFORMATION: Wherein n may be a, c, g or t
<220> FEATURE:
<221> NAME/KEY: misc_feature
<222> LOCATION: (55)..(55)
<223> OTHER INFORMATION: Wherein n may be a, c, g or t
<220> FEATURE:
<221> NAME/KEY: misc_feature
<222> LOCATION: (56)..(56)
<223> OTHER INFORMATION: Wherein n may be a, c, g or t

<400> SEQUENCE: 10
nnnnnnaagc ttcgatgtga tccgatcgac tggtgtcgta ctaggaattc nnnnnn        56

<210> SEQ ID NO 11
<211> LENGTH: 38
<212> TYPE: DNA
<213> ORGANISM: Homo sapiens

<400> SEQUENCE: 11
aattcctagt acgacaccag tcgatcggat cacatcga        38

<210> SEQ ID NO 12
<211> LENGTH: 38
<212> TYPE: DNA
<213> ORGANISM: Homo sapiens

<400> SEQUENCE: 12
agcttcgatg tgatccgatc gactggtgtc gtactagg                    38

<210> SEQ ID NO 13
<211> LENGTH: 33
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t

<400> SEQUENCE: 13
ataacttcgt atacctnagc tatacgaagt tat                         33

<210> SEQ ID NO 14
<211> LENGTH: 37
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n may be a, c, g or t

<400> SEQUENCE: 14
aattataact tcgtatagct naggtatacg aagttat                     37

<210> SEQ ID NO 15
<211> LENGTH: 37
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n may be a, c, g or t

<400> SEQUENCE: 15
agctataact tcgtatagct naggtatacg aagttat                     37

<210> SEQ ID NO 16
<211> LENGTH: 33
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t

<400> SEQUENCE: 16
ataacttcgt atacctnagc tatacgaagt tat                         33

<210> SEQ ID NO 17
<211> LENGTH: 108
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t
<220> FEATURE:
<221> NAME/KEY: misc_feature
<222> LOCATION: (92)..(92)

<223> OTHER INFORMATION: Wherein n may be a, c, g or t

<400> SEQUENCE: 17
ataacttcgt ataccthagc tatacgaagt tataattcct agtacgacac cagtcgatcg    60
gatcacatcg aagctataac ttcgtatagc thaggtatac gaagttat              108

<210> SEQ ID NO 18
<211> LENGTH: 108
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t
<220> FEATURE:
<221> NAME/KEY: misc_feature
<222> LOCATION: (92)..(92)
<223> OTHER INFORMATION: Wherein n may be a, c, g or t

<400> SEQUENCE: 18
ataacttcgt ataccthagc tatacgaagt tatagcttcg atgtgatccg atcgactggt    60
gtcgtactag gaattataac ttcgtatagc thaggtatac gaagttat              108

<210> SEQ ID NO 19
<211> LENGTH: 56
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Wherein n may be a, c, g or t
<220> FEATURE:
<221> NAME/KEY: misc_feature
<222> LOCATION: (2)..(2)
<223> OTHER INFORMATION: Wherein n may be a, c, g or t
<220> FEATURE:
<221> NAME/KEY: misc_feature
<222> LOCATION: (3)..(3)
<223> OTHER INFORMATION: Wherein n may be a, c, g or t
<220> FEATURE:
<221> NAME/KEY: misc_feature
<222> LOCATION: (4)..(4)
<223> OTHER INFORMATION: Wherein n may be a, c, g or t
<220> FEATURE:
<221> NAME/KEY: misc_feature
<222> LOCATION: (5)..(5)
<223> OTHER INFORMATION: Wherein n may be a, c, g or t
<220> FEATURE:
<221> NAME/KEY: misc_feature
<222> LOCATION: (6)..(6)
<223> OTHER INFORMATION: Wherein n may be a, c, g or t
<220> FEATURE:
<221> NAME/KEY: misc_feature
<222> LOCATION: (51)..(51)
<223> OTHER INFORMATION: Wherein n may be a, c, g or t
<220> FEATURE:
<221> NAME/KEY: misc_feature
<222> LOCATION: (52)..(52)
<223> OTHER INFORMATION: Wherein n may be a, c, g or t
<220> FEATURE:
<221> NAME/KEY: misc_feature
<222> LOCATION: (53)..(53)
<223> OTHER INFORMATION: Wherein n may be a, c, g or t
<220> FEATURE:
<221> NAME/KEY: misc_feature
<222> LOCATION: (54)..(54)
<223> OTHER INFORMATION: Wherein n may be a, c, g or t
<220> FEATURE:
<221> NAME/KEY: misc_feature
<222> LOCATION: (55)..(55)
<223> OTHER INFORMATION: Wherein n may be a, c, g or t
<220> FEATURE:
<221> NAME/KEY: misc_feature
<222> LOCATION: (56)..(56)
<223> OTHER INFORMATION: Wherein n may be a, c, g or t

<400> SEQUENCE: 19
nnnnnngaat tcctagtacg acaccagtcg atcggatcac atcggaattc nnnnnn    56

<210> SEQ ID NO 20
<211> LENGTH: 56
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Wherein n may be a, c, g or t
<220> FEATURE:
<221> NAME/KEY: misc_feature
<222> LOCATION: (2)..(2)
<223> OTHER INFORMATION: Wherein n may be a, c, g or t
<220> FEATURE:
<221> NAME/KEY: misc_feature
<222> LOCATION: (3)..(3)
<223> OTHER INFORMATION: Wherein n may be a, c, g or t
<220> FEATURE:
<221> NAME/KEY: misc_feature
<222> LOCATION: (4)..(4)
<223> OTHER INFORMATION: Wherein n may be a, c, g or t
<220> FEATURE:
<221> NAME/KEY: misc_feature
<222> LOCATION: (5)..(5)
<223> OTHER INFORMATION: Wherein n may be a, c, g or t
<220> FEATURE:
<221> NAME/KEY: misc_feature
<222> LOCATION: (6)..(6)
<223> OTHER INFORMATION: Wherein n may be a, c, g or t
<220> FEATURE:
<221> NAME/KEY: misc_feature
<222> LOCATION: (51)..(51)
<223> OTHER INFORMATION: Wherein n may be a, c, g or t
<220> FEATURE:
<221> NAME/KEY: misc_feature
<222> LOCATION: (52)..(52)
<223> OTHER INFORMATION: Wherein n may be a, c, g or t
<220> FEATURE:
<221> NAME/KEY: misc_feature
<222> LOCATION: (53)..(53)
<223> OTHER INFORMATION: Wherein n may be a, c, g or t
<220> FEATURE:
<221> NAME/KEY: misc_feature
<222> LOCATION: (54)..(54)
<223> OTHER INFORMATION: Wherein n may be a, c, g or t
<220> FEATURE:
<221> NAME/KEY: misc_feature
<222> LOCATION: (55)..(55)
<223> OTHER INFORMATION: Wherein n may be a, c, g or t
<220> FEATURE:
<221> NAME/KEY: misc_feature
<222> LOCATION: (56)..(56)
<223> OTHER INFORMATION: Wherein n may be a, c, g or t

<400> SEQUENCE: 20
nnnnnngaat tccgatgtga tccgatcgac tggtgtcgta ctaggaattc nnnnnn    56

<210> SEQ ID NO 21
<211> LENGTH: 38
<212> TYPE: DNA
<213> ORGANISM: Homo sapiens

<400> SEQUENCE: 21
aattcctagt acgacaccag tcgatcggat cacatcgg    38

<210> SEQ ID NO 22
<211> LENGTH: 38
<212> TYPE: DNA

<213> ORGANISM: Homo sapiens

<400> SEQUENCE: 22
aattccgatg tgatccgatc gactggtgtc gtactagg                            38

<210> SEQ ID NO 23
<211> LENGTH: 33
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t

<400> SEQUENCE: 23
ataacttcgt atacctnagc tatacgaagt tat                                 33

<210> SEQ ID NO 24
<211> LENGTH: 37
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n may be a, c, g or t

<400> SEQUENCE: 24
aattataact tcgtatagct naggtatacg aagttat                             37

<210> SEQ ID NO 25
<211> LENGTH: 108
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t
<220> FEATURE:
<221> NAME/KEY: misc_feature
<222> LOCATION: (92)..(92)
<223> OTHER INFORMATION: Wherein n may be a, c, g or t

<400> SEQUENCE: 25
ataacttcgt atacctnagc tatacgaagt tataattcct agtacgacac cagtcgatcg    60
gatcacatcg gaattataac ttcgtatagc tnaggtatac gaagttat                108

<210> SEQ ID NO 26
<211> LENGTH: 108
<212> TYPE: DNA
<213> ORGANISM: Homo sapiens
<220> FEATURE:
<221> NAME/KEY: misc_feature
<222> LOCATION: (17)..(17)
<223> OTHER INFORMATION: Wherein n may be a, c, g or t
<220> FEATURE:
<221> NAME/KEY: misc_feature
<222> LOCATION: (92)..(92)
<223> OTHER INFORMATION: Wherein n may be a, c, g or t

<400> SEQUENCE: 26
ataacttcgt atacctnagc tatacgaagt tataattccg atgtgatccg atcgactggt    60
gtcgtactag gaattataac ttcgtatagc tnaggtatac gaagttat                108

<210> SEQ ID NO 27
<211> LENGTH: 68
<212> TYPE: DNA
<213> ORGANISM: Homo sapiens

```
<220> FEATURE:
<221> NAME/KEY: misc_feature
<222> LOCATION: (56)..(56)
<223> OTHER INFORMATION: Wherein n is biotinylated thymine

<400> SEQUENCE: 27
gttggaaccg aaagggtttg aattccgggt ttttaaaaac ccggaattca aacccnttcg      60
gttccaac                                                              68

<210> SEQ ID NO 28
<211> LENGTH: 24
<212> TYPE: DNA
<213> ORGANISM: Homo sapiens
<220> FEATURE:
<221> NAME/KEY: misc_feature
<222> LOCATION: (12)..(12)
<223> OTHER INFORMATION: Wherein n is biotinylated thymine

<400> SEQUENCE: 28
aattcaaacc cnttcggttc caac                                            24

<210> SEQ ID NO 29
<211> LENGTH: 20
<212> TYPE: DNA
<213> ORGANISM: Homo sapiens

<400> SEQUENCE: 29
gttggaaccg aaagggtttg                                                 20

<210> SEQ ID NO 30
<211> LENGTH: 68
<212> TYPE: DNA
<213> ORGANISM: Homo sapiens
<220> FEATURE:
<221> NAME/KEY: misc_feature
<222> LOCATION: (23)..(23)
<223> OTHER INFORMATION: Wherein n is inosine
<220> FEATURE:
<221> NAME/KEY: misc_feature
<222> LOCATION: (47)..(47)
<223> OTHER INFORMATION: Wherein n is inosine

<400> SEQUENCE: 30
gttggaaccg aaagggttta acnttcgggt ttttaaaaac ccgaacntta aacccttttcg    60 gttccaac                                                              68

<210> SEQ ID NO 31
<211> LENGTH: 19
<212> TYPE: DNA
<213> ORGANISM: Homo sapiens

<400> SEQUENCE: 31 aaacccttttc ggttccaac                                                 19

<210> SEQ ID NO 32
<211> LENGTH: 25
<212> TYPE: DNA
<213> ORGANISM: Homo sapiens
<220> FEATURE:
<221> NAME/KEY: misc_feature
<222> LOCATION: (23)..(23)
<223> OTHER INFORMATION: Wherein n is inosine

<400> SEQUENCE: 32
gttggaaccg aaagggttta acntt                                           25
```

```
<210> SEQ ID NO 33
<211> LENGTH: 68
<212> TYPE: DNA
<213> ORGANISM: Homo sapiens
<220> FEATURE:
<221> NAME/KEY: misc_feature
<222> LOCATION: (23)..(23)
<223> OTHER INFORMATION: Wherein n is inosine
<220> FEATURE:
<221> NAME/KEY: misc_feature
<222> LOCATION: (47)..(47)
<223> OTHER INFORMATION: Wherein n is inosine

<400> SEQUENCE: 33
gttggaaccg aaagggtttg gcnttcgggt ttttaaaaac ccgaacncca aaccctttcg      60
gttccaac                                                              68

<210> SEQ ID NO 34
<211> LENGTH: 19
<212> TYPE: DNA
<213> ORGANISM: Homo sapiens

<400> SEQUENCE: 34
aaaccctttc ggttccaac                                                  19

<210> SEQ ID NO 35
<211> LENGTH: 25
<212> TYPE: DNA
<213> ORGANISM: Homo sapiens
<220> FEATURE:
<221> NAME/KEY: misc_feature
<222> LOCATION: (23)..(23)
<223> OTHER INFORMATION: Wherein n is inosine

<400> SEQUENCE: 35
gttggaaccg aaagggtttg gcntt                                           25

<210> SEQ ID NO 36
<211> LENGTH: 68
<212> TYPE: DNA
<213> ORGANISM: Homo sapiens
<220> FEATURE:
<221> NAME/KEY: misc_feature
<222> LOCATION: (15)..(15)
<223> OTHER INFORMATION: Wherein n is inosine
<220> FEATURE:
<221> NAME/KEY: misc_feature
<222> LOCATION: (43)..(43)
<223> OTHER INFORMATION: Wherein n is inosine

<400> SEQUENCE: 36
gttggaaccg aaagngtttc gaattcgggt ttttaaaaac ccnaattcga aaccctttcg      60
gttccaac                                                              68

<210> SEQ ID NO 37
<211> LENGTH: 23
<212> TYPE: DNA
<213> ORGANISM: Homo sapiens

<400> SEQUENCE: 37
ttcgaaaccc tttcggttcc aac                                             23

<210> SEQ ID NO 38
<211> LENGTH: 17
<212> TYPE: DNA
<213> ORGANISM: Homo sapiens
```

```
<220> FEATURE:
<221> NAME/KEY: misc_feature
<222> LOCATION: (15)..(15)
<223> OTHER INFORMATION: Wherein n is inosine

<400> SEQUENCE: 38
gttggaaccg aaagngt                                                   17

<210> SEQ ID NO 39
<211> LENGTH: 68
<212> TYPE: DNA
<213> ORGANISM: Homo sapiens
<220> FEATURE:
<221> NAME/KEY: misc_feature
<222> LOCATION: (15)..(15)
<223> OTHER INFORMATION: Wherein n is inosine
<220> FEATURE:
<221> NAME/KEY: misc_feature
<222> LOCATION: (43)..(43)
<223> OTHER INFORMATION: Wherein n is inosine

<400> SEQUENCE: 39
gttggaaccg aaagngtttc gttttcgggt ttttaaaaac ccnaaaacga aacccttcg     60 gttccaac                                                             68

<210> SEQ ID NO 40
<211> LENGTH: 23
<212> TYPE: DNA
<213> ORGANISM: Homo sapiens

<400> SEQUENCE: 40
aacgaaaccc tttcggttcc aac                                            23

<210> SEQ ID NO 41
<211> LENGTH: 17
<212> TYPE: DNA
<213> ORGANISM: Homo sapiens
<220> FEATURE:
<221> NAME/KEY: misc_feature
<222> LOCATION: (15)..(15)
<223> OTHER INFORMATION: Wherein n is inosine

<400> SEQUENCE: 41
gttggaaccg aaagngt                                                   17

<210> SEQ ID NO 42
<211> LENGTH: 68
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n is inosine
<220> FEATURE:
<221> NAME/KEY: misc_feature
<222> LOCATION: (43)..(43)
<223> OTHER INFORMATION: Wherein n is inosine

<400> SEQUENCE: 42
gttggaaccg aaagggttta naattcgggt ttttaaaaac ccnaattcta aacccttcg     60 gttccaac                                                             68

<210> SEQ ID NO 43
<211> LENGTH: 23
<212> TYPE: DNA
<213> ORGANISM: Homo sapiens
```

```
<400> SEQUENCE: 43
ttctaaaccc tttcggttcc aac                                          23

<210> SEQ ID NO 44
<211> LENGTH: 23
<212> TYPE: DNA
<213> ORGANISM: Homo sapiens
<220> FEATURE:
<221> NAME/KEY: misc_feature
<222> LOCATION: (21)..(21)
<223> OTHER INFORMATION: Wherein n is inosine

<400> SEQUENCE: 44
gttggaaccg aagggttta naa                                           23

<210> SEQ ID NO 45
<211> LENGTH: 21
<212> TYPE: DNA
<213> ORGANISM: Homo sapiens
<220> FEATURE:
<221> NAME/KEY: misc_feature
<222> LOCATION: (20)..(20)
<223> OTHER INFORMATION: Wherein n is inosine
<220> FEATURE:
<221> NAME/KEY: misc_feature
<222> LOCATION: (21)..(21)
<223> OTHER INFORMATION: Wherein n may be a, c, g or t

<400> SEQUENCE: 45
gcctccctcg cgccatcagn n                                            21

<210> SEQ ID NO 46
<211> LENGTH: 15
<212> TYPE: DNA
<213> ORGANISM: Homo sapiens

<400> SEQUENCE: 46
ctgatggcgc gaggg                                                   15

<210> SEQ ID NO 47
<211> LENGTH: 21
<212> TYPE: DNA
<213> ORGANISM: Homo sapiens
<220> FEATURE:
<221> NAME/KEY: misc_feature
<222> LOCATION: (20)..(20)
<223> OTHER INFORMATION: Wherein n may be a, c, g or t
<220> FEATURE:
<221> NAME/KEY: misc_feature
<222> LOCATION: (21)..(21)
<223> OTHER INFORMATION: Wherein n may be a, c, g or t

<400> SEQUENCE: 47
gccttgccag cccgctcagn n                                            21

<210> SEQ ID NO 48
<211> LENGTH: 15
<212> TYPE: DNA
<213> ORGANISM: Homo sapiens

<400> SEQUENCE: 48
ctgagcgggc tggca                                                   15

<210> SEQ ID NO 49
<211> LENGTH: 15
<212> TYPE: DNA
<213> ORGANISM: Homo sapiens
```

```
<220> FEATURE:
<221> NAME/KEY: misc_feature
<222> LOCATION: (1)..(1)
<223> OTHER INFORMATION: Wherein n is biotinylated guanine

<400> SEQUENCE: 49
ncctccctcg cgcca                                                          15

<210> SEQ ID NO 50
<211> LENGTH: 15
<212> TYPE: DNA
<213> ORGANISM: Homo sapiens

<400> SEQUENCE: 50
gccttgccag cccgc                                                          15

<210> SEQ ID NO 51
<211> LENGTH: 21
<212> TYPE: DNA
<213> ORGANISM: Homo sapiens
<220> FEATURE:
<221> NAME/KEY: misc_feature
<222> LOCATION: (20)..(20)
<223> OTHER INFORMATION: Wherein n may be a, c, g or t
<220> FEATURE:
<221> NAME/KEY: misc_feature
<222> LOCATION: (21)..(21)
<223> OTHER INFORMATION: Wherein n may be a, c, g or t

<400> SEQUENCE: 51
ccgcccagca tcgcctcagn n                                                   21

<210> SEQ ID NO 52
<211> LENGTH: 15
<212> TYPE: DNA
<213> ORGANISM: Homo sapiens

<400> SEQUENCE: 52
ctgaggcgat gctgg                                                          15

<210> SEQ ID NO 53
<211> LENGTH: 21
<212> TYPE: DNA
<213> ORGANISM: Homo sapiens
<220> FEATURE:
<221> NAME/KEY: misc_feature
<222> LOCATION: (20)..(20)
<223> OTHER INFORMATION: Wherein n may be a, c, g or t
<220> FEATURE:
<221> NAME/KEY: misc_feature
<222> LOCATION: (21)..(21)
<223> OTHER INFORMATION: Wherein n may be a, c, g or t

<400> SEQUENCE: 53
ccgcccgagc accgctcagn n                                                   21

<210> SEQ ID NO 54
<211> LENGTH: 15
<212> TYPE: DNA
<213> ORGANISM: Homo sapiens

<400> SEQUENCE: 54
ctgagcggtg ctcgg                                                          15

<210> SEQ ID NO 55
<211> LENGTH: 15
<212> TYPE: DNA
```

-continued

```
<213> ORGANISM: Homo sapiens
<220> FEATURE:
<221> NAME/KEY: misc_feature
<222> LOCATION: (1)..(1)
<223> OTHER INFORMATION: Wherein n is biotinylated cytosine

<400> SEQUENCE: 55
ncgcccagca tcgcc                                                   15

<210> SEQ ID NO 56
<211> LENGTH: 15
<212> TYPE: DNA
<213> ORGANISM: Homo sapiens

<400> SEQUENCE: 56
ccgcccgagc accgc                                                   15
```

PAIRED END SEQUENCING

CROSS-REFERENCE TO RELATED APPLICATIONS

This application claims priority from U.S. Provisional Patent Application Ser. Nos. 60/688,042, filed Jun. 6, 2005, 60/717,964, filed Sep. 16, 2005, and 60/771,818, filed Feb. 8, 2006, the contents of which are incorporated herein by reference.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

GOVERNMENT INTERESTS

This invention was made with U.S. Government support under grant number R01 HG003562 awarded by NIH. The U.S. Government may have certain rights in this invention.

FIELD OF THE INVENTION

The present invention is related to the field of nucleic acid sequencing, genomic sequencing, and the assembly of the sequencing results into a contiguous sequence.

BACKGROUND OF THE INVENTION

One approach to sequencing a large target nucleic acid, such as a human genome, is the use of shotgun sequencing. In shotgun sequencing, the target nucleic acid is fragmented or subcloned to produce a series of overlapping nucleic acid fragments and determining the sequence of these fragments. Based on the overlap and the knowledge of the sequence of each fragment, the complete sequence of a target nucleic acid can be constructed.

One disadvantage of the shotgun approach to sequencing is that assembly may be difficult if the target nucleic acid sequence comprise numerous small repeats (tandem or inverted repeats). The inability to assemble a genomic sequence in repeat regions leads to gaps in the assembled sequence. Thus, following initial assembly of a nucleic acid sequence, gaps in sequence coverage would need to be filled and uncertainties in assembly would need to be resolved.

One method of resolving these gaps is to use larger clones or fragments for sequencing because these larger fragments would be long enough to span the repeat regions. However, the sequencing of large fragments of nucleic acid is more difficult and time consuming in current sequencing apparatus.

Another approach to spanning a gap in the sequence is to determine the sequence of both ends of a large fragment. In contrast to single sequence reads of one end of a shotgun sequencing fragment, a pair of sequence reads from both ends have known spacing and orientation. The use of relatively long fragments also aids in the assembly of sequences containing interspersed repetitive elements. This type of approach (Smith, M. W. et al., Nature Genetics 7: 40-47 (1994) is known in the art as paired end sequencing. The present invention includes novel methods, systems and compositions useful for paired-end sequencing approaches and other nucleic acid technologies.

BRIEF SUMMARY OF THE INVENTION

One embodiment of the invention is directed to a method for obtaining a DNA construct comprising two end regions of a target nucleic acid which can be a large segment from the genome of an organism. The method comprises the following steps:

(a) fragmenting a large nucleic acid molecule to produce a target nucleic acid;

(b) ligating a capture element to the target nucleic acid to form a first circular nucleic acid molecule;

(c) digesting the first circular nucleic acid with a restriction endonuclease which cuts the target nucleic acid but which does not cut the capture element to produce a linear nucleic acid which comprise two ends of the target nucleic acid separated by the capture element;

(d) ligating the linear nucleic acid with a separator element to form a second circular nucleic acid;

(e) converting the second circular nucleic acid to a circular single strand nucleic acid;

(f) annealing a first oligonucleotide to the circular single stranded nucleic acid and amplifying the circular single stranded nucleic acid by rolling circle amplification to produce a single stranded rolling circle amplification product;

(g) annealing a second oligonucleotide to the single stranded rolling circle amplification product to form multiple double stranded regions in the single stranded rolling amplification product; and (h) digesting the single stranded rolling circle amplification product into small fragments with a restriction endonuclease which cleaves the multiple double stranded regions to produce the DNA construct comprising two end regions of a target nucleic acid.

Another embodiment of the invention is directed to a second method for obtaining a DNA construct comprising two end regions of a target nucleic acid. The method comprise the following steps:

(a) fragmenting a large nucleic acid molecule to produce a target nucleic acid;

(b) ligating an adaptor to each end of the target nucleic acid;

(c) ligating a signature tag to the target nucleic acid to form a circular nucleic acid molecule;

(d) digesting the circular nucleic acid with a restriction endonuclease which cuts the target nucleic acid but which does not cut the adaptor or the signature tag to produce the DNA construct comprising two end region of a target nucleic acid.

The methods of the invention may be performed simultaneously on a plurality of target DNA fragments to produce a library of DNA constructs which contain the ends from a large fragment of DNA. One advantage of the invention is that a library may be constructed in vitro without the use of prokaryotic or eukaryotic host cells.

These and other embodiments are disclosed or are obvious from and encompassed by the following Detailed Description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following Detailed Description, given by way of example, but not intended to limit the invention to specific embodiments described, may be understood in conjunction with the accompanying Figures, incorporated herein by reference, in which:

FIG. 3 depicts the sequence and design of capture fragments. The identities of the sequences are as follows:

| | |
|---|---|
| Paired-end capture fragment product | SEQ ID NO:1 |
| Oligo 1 | SEQ ID NO:2 |
| Oligo 2 | SEQ ID NO:3 |
| Oligo 3 | SEQ ID NO:4 |
| Oligo 4 | SEQ ID NO:5 |
| Paired-end capture fragment product (type IIS, MmeI) | SEQ ID NO:6 |
| Short adaptor paired end capture fragment | SEQ ID NO:7 |
| Short adaptor paired end capture fragment (type IIS, MmeI) | SEQ ID NO:8 |

Figure 4:
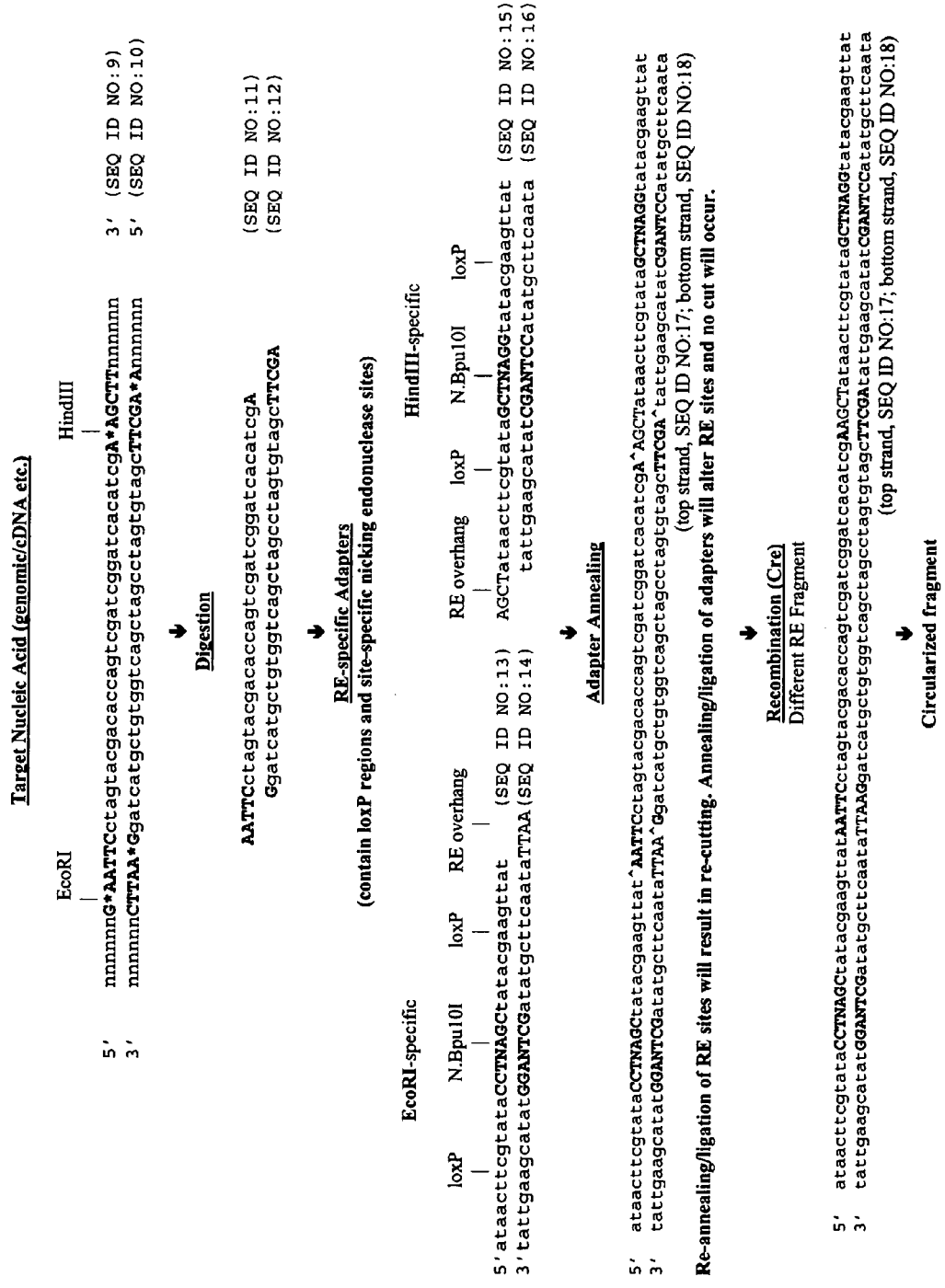

FIG. 4 depicts one embodiment of a RE fragment.

Figure 5:
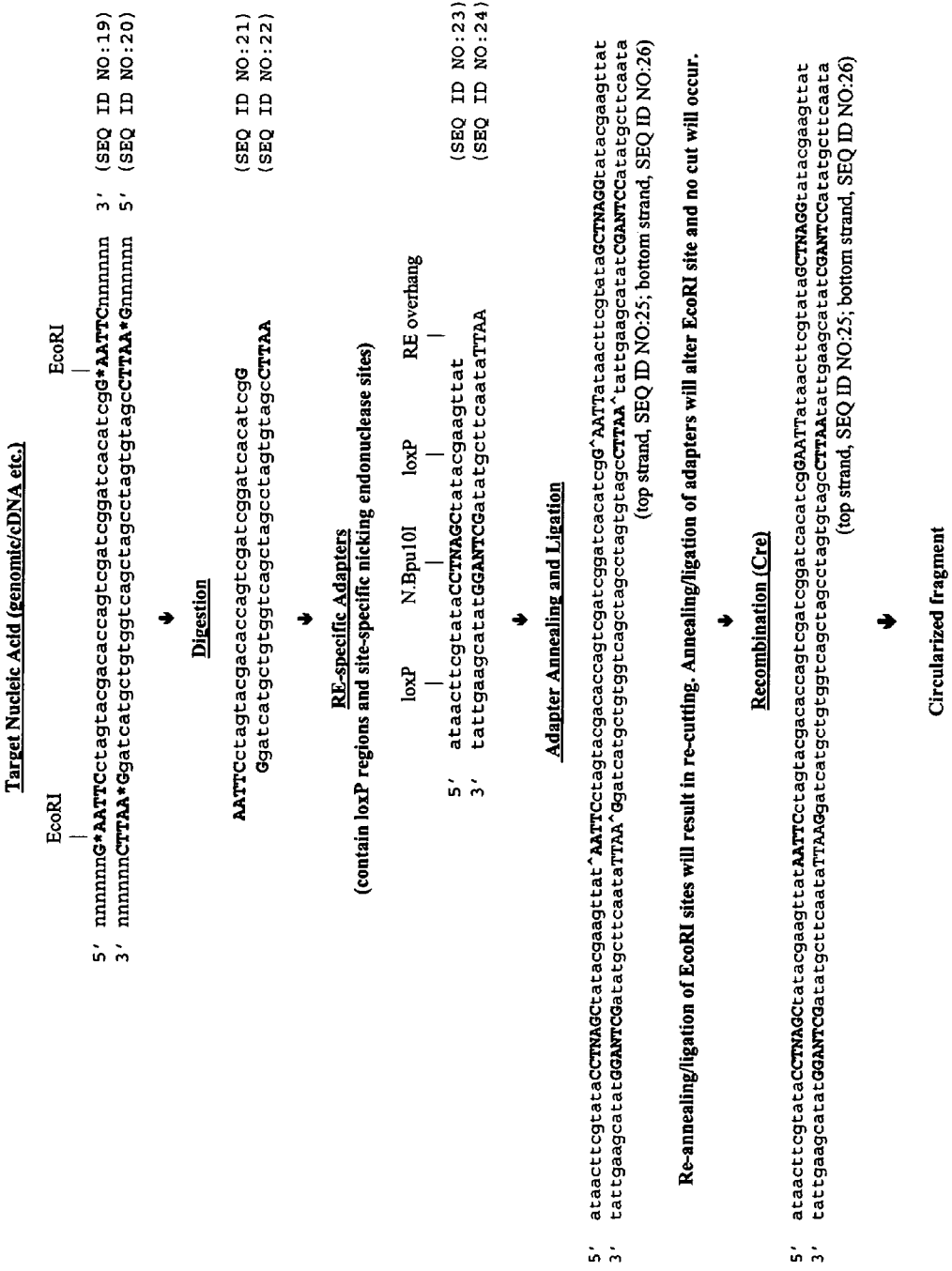

FIG. 5 depicts another embodiment of a RE fragment.

Figure 6:
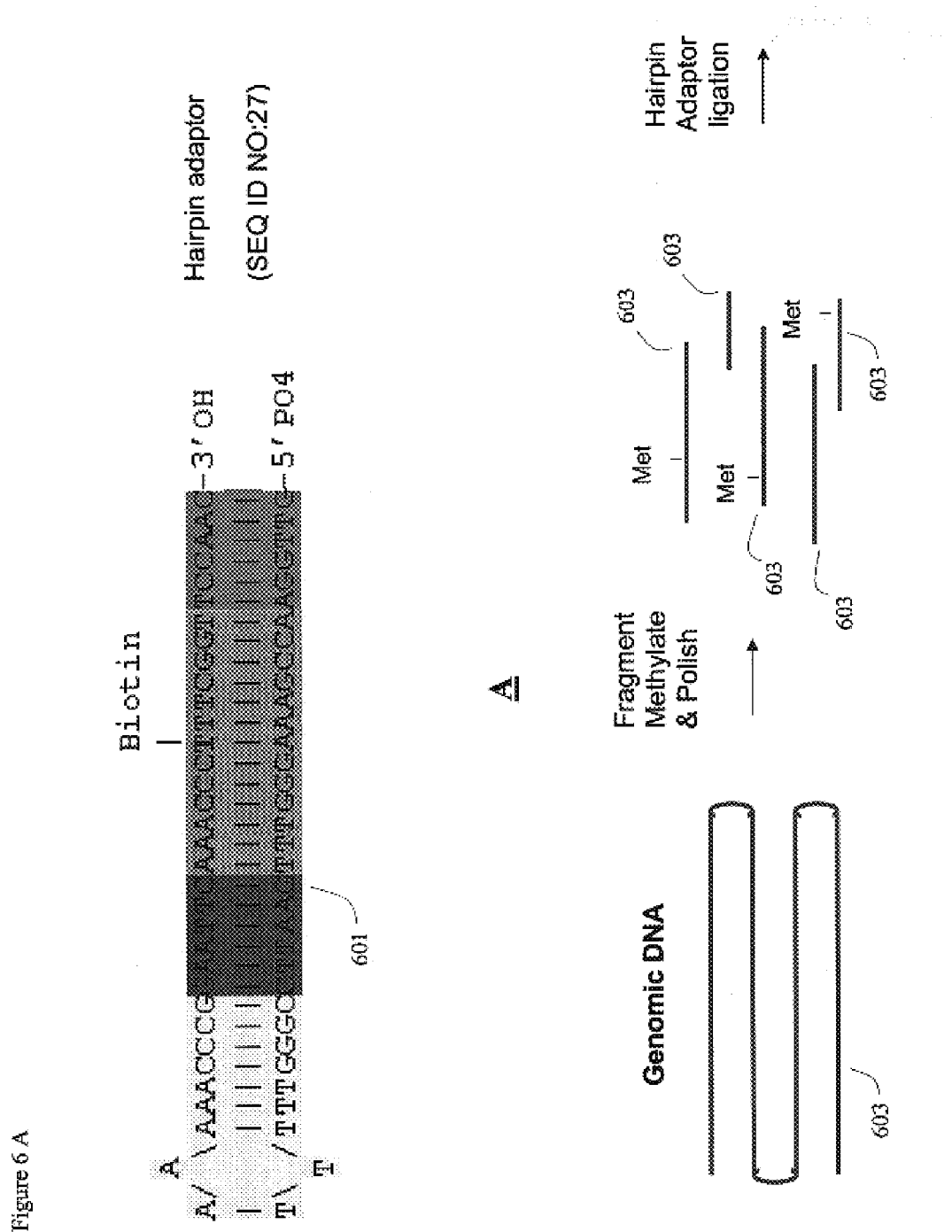
Figure 6:
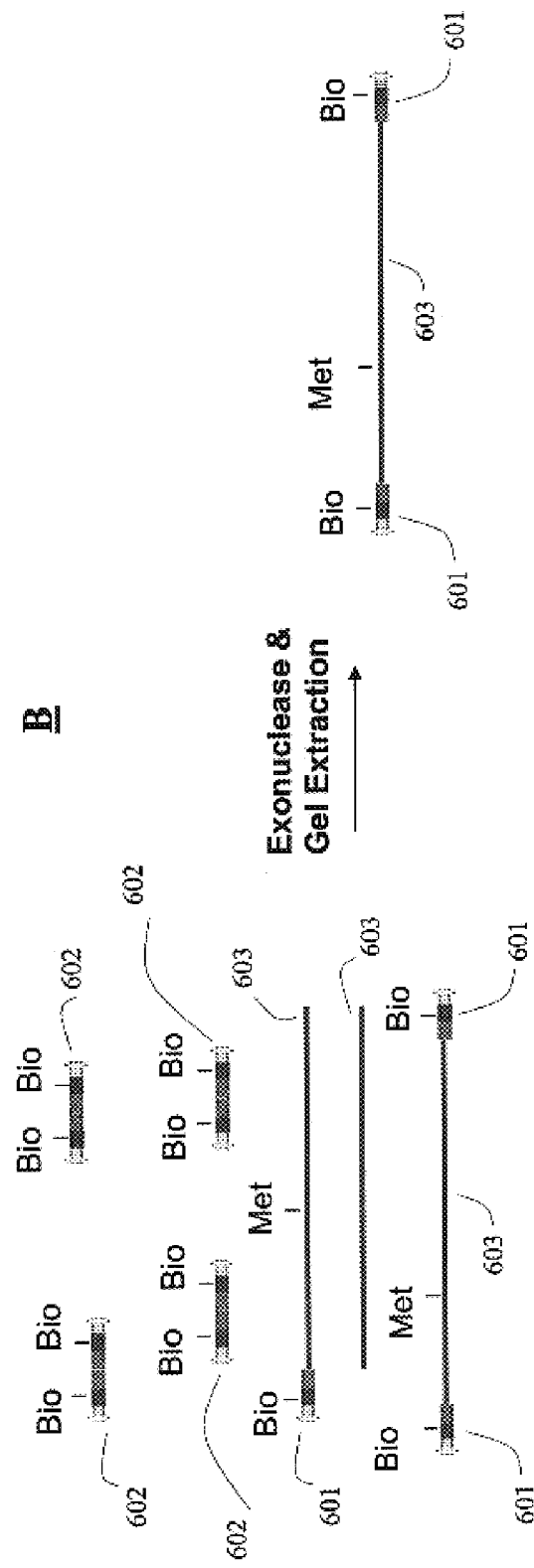
Figure 6:
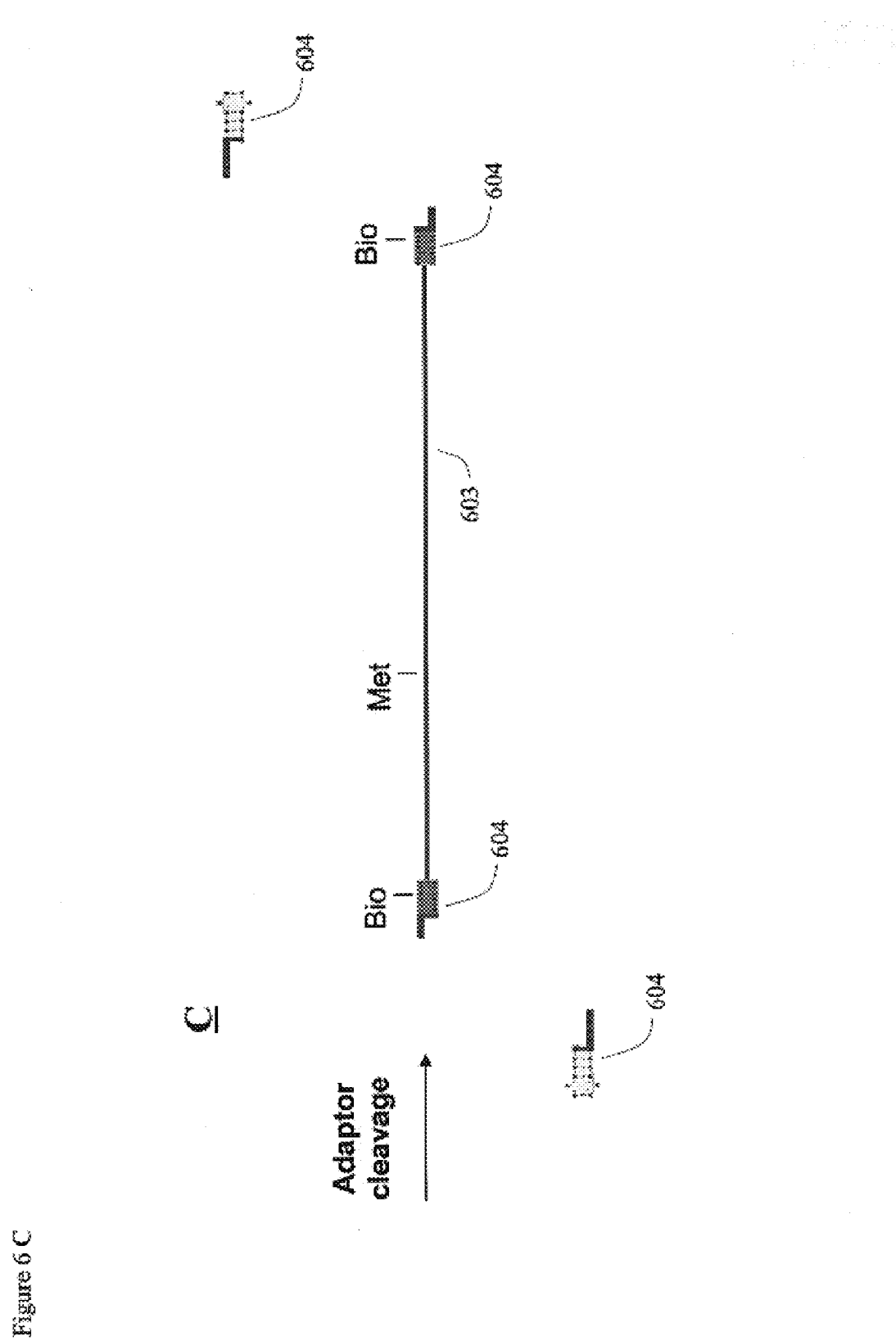
Figure 6:
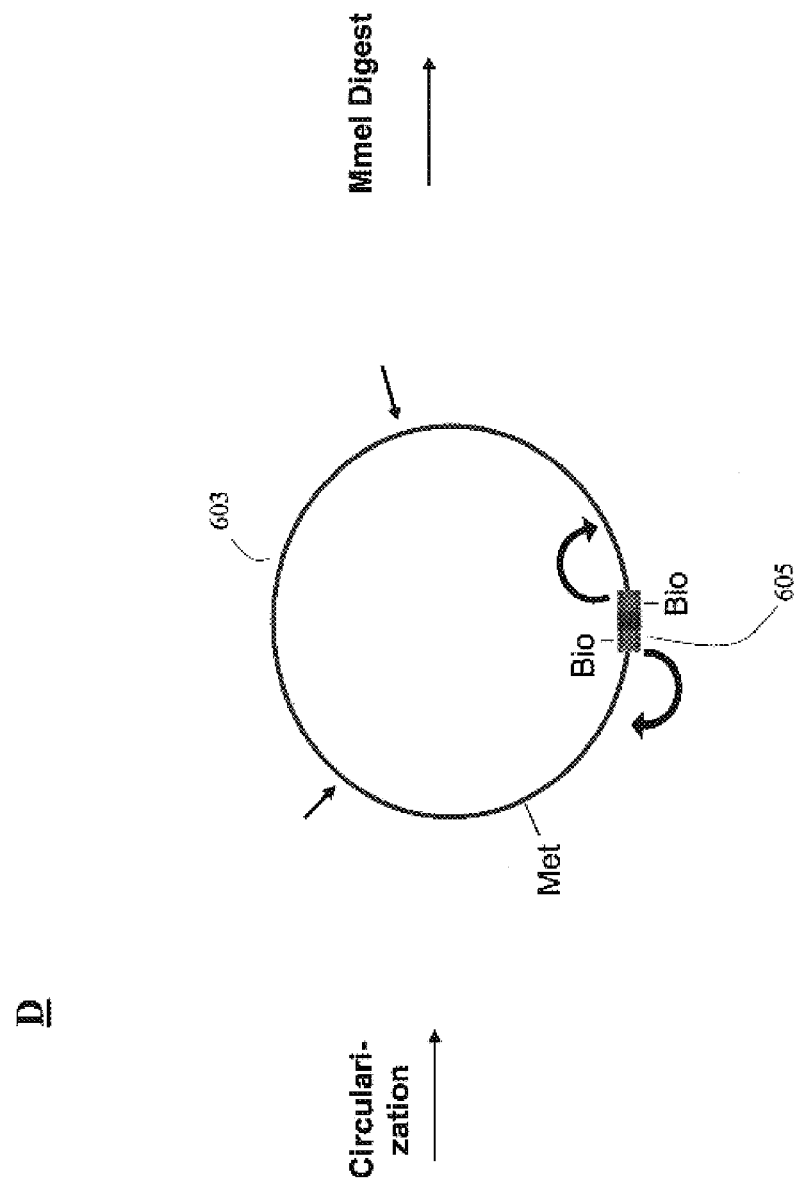
Figure 6:
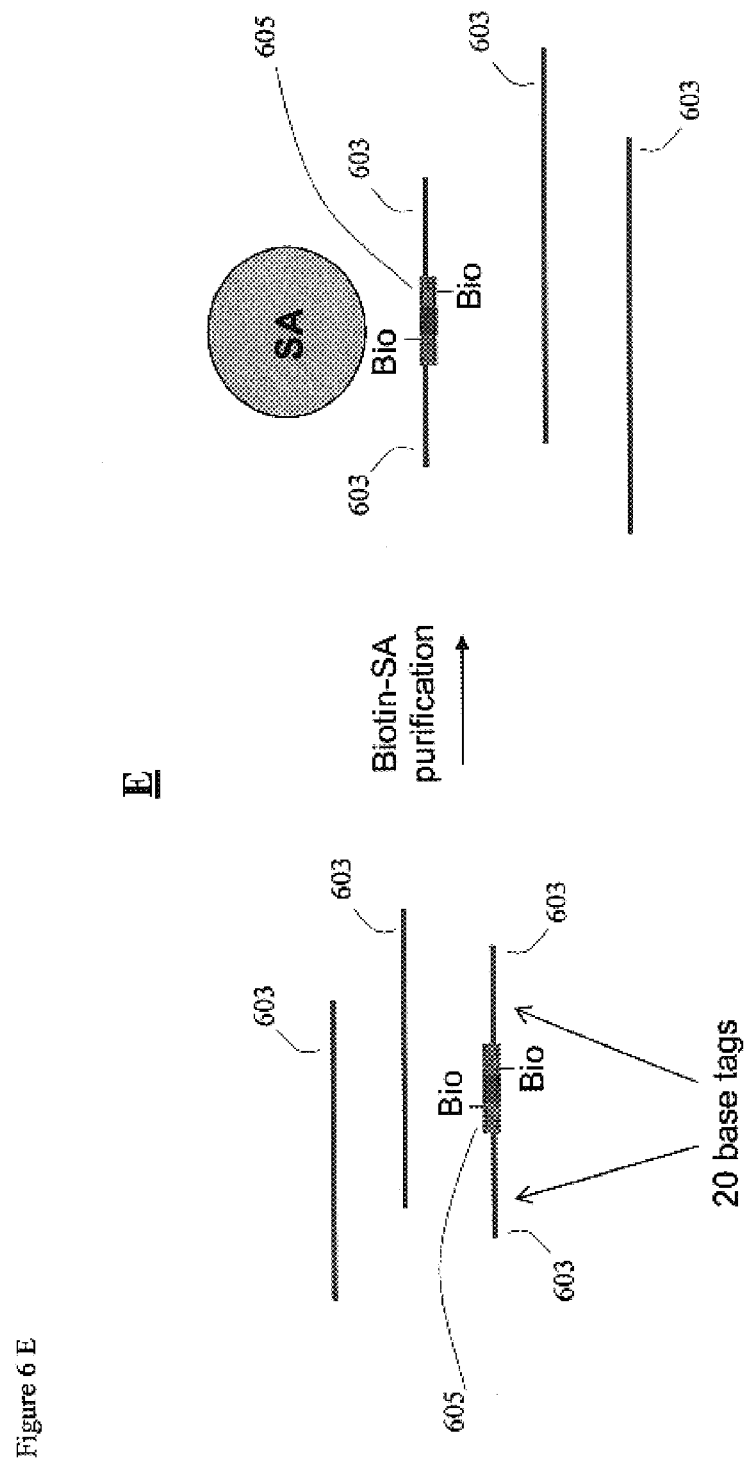
Figure 6:
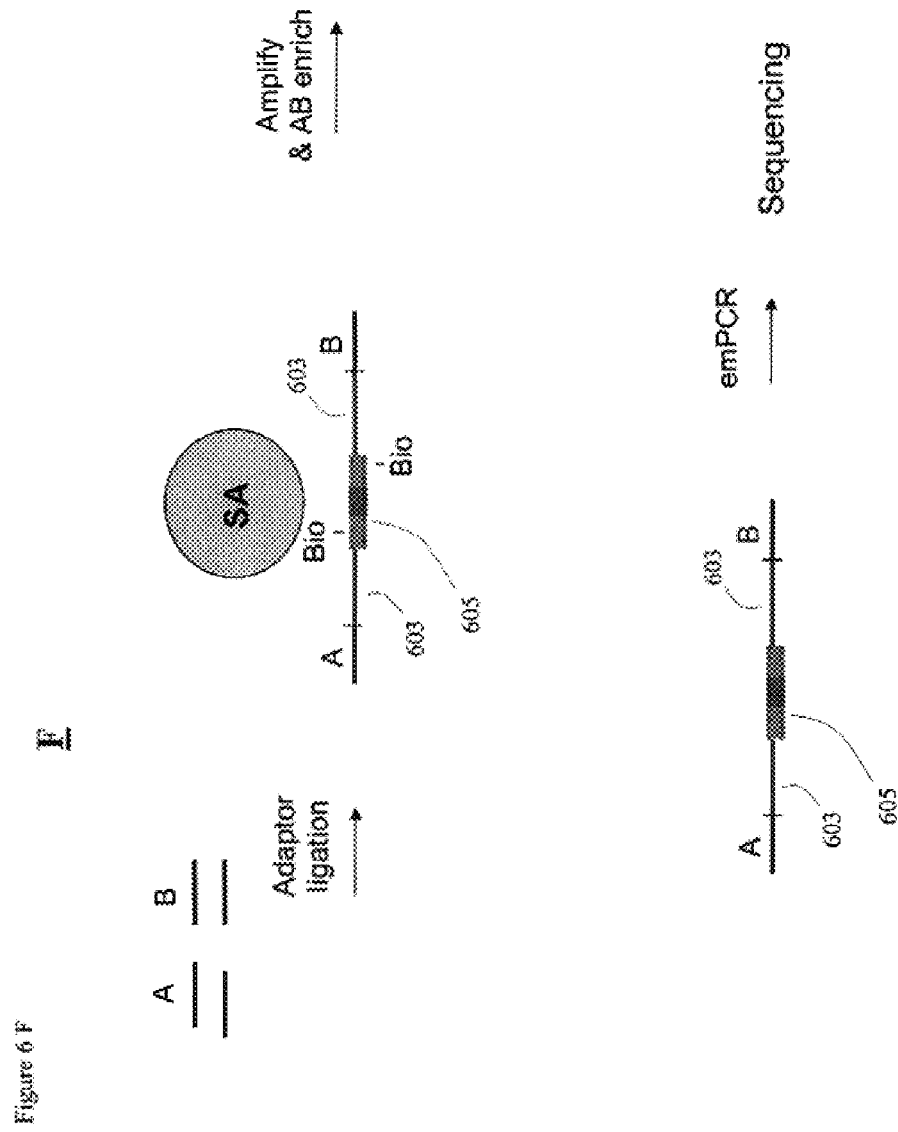

FIG. 6 depicts a paired end read approach using a hairpin adaptor. The hairpin adaptor has the following sequence:

(SEQ ID NO:27)

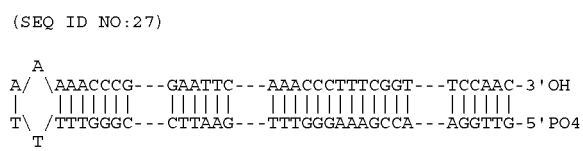

The hairpin adaptor is one continuous nucleic acid sequence, which is depicted as separated into 4 regions above. The four regions are, from left to right, the hairpin region, restriction endonuclease recognition site, a biotinylated region, and a type IIS restriction endonuclease recognition site. "601" denotes the hairpin adaptor. "603" denotes genomic DNA. Met denotes methylated DNA. "602" denotes hairpin adaptor dimers. "604" denotes hairpin adaptor cleaved by restriction endonuclease. "605" denotes two hairpin adaptors cleaved by restriction endonuclease and religated. SA denotes streptavidin bead. Bio denotes biotin (e.g., biotinylated DNA).

FIG. 7 depicts improvements to a paired end procedure.

Figure 8:
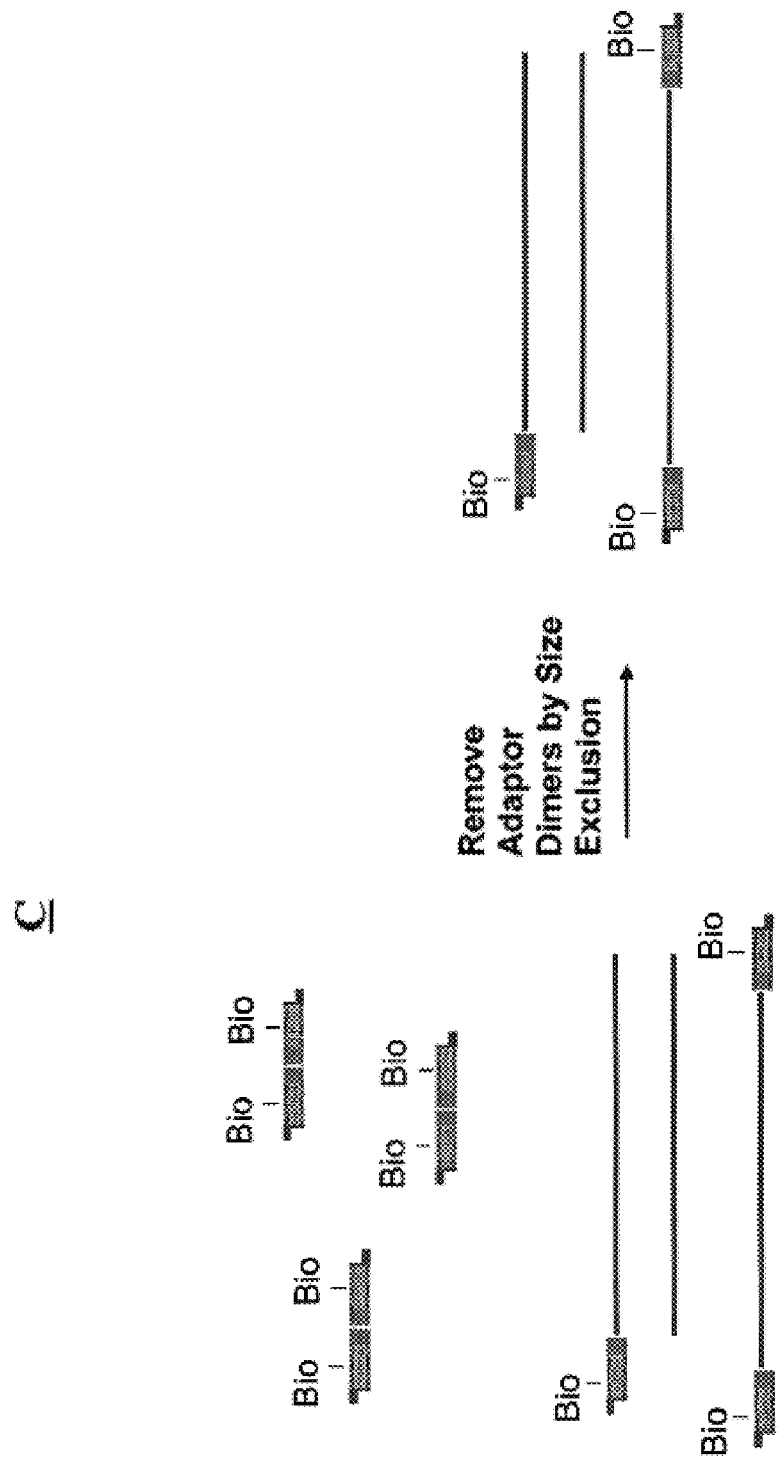
Figure 8:
Figure 8:
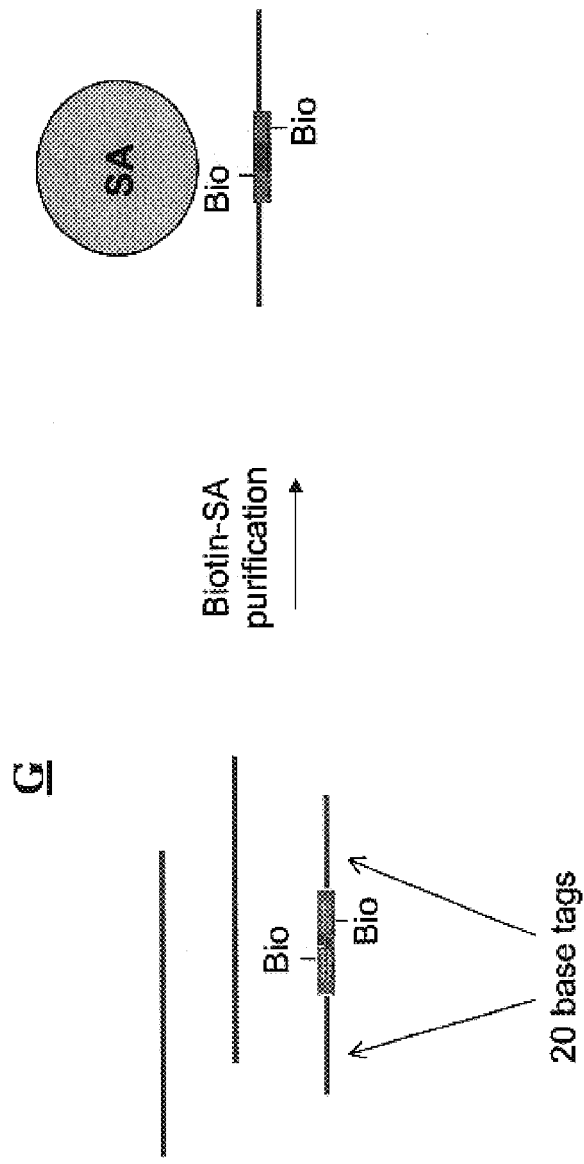

FIG. 8 depicts a paired-end read approach with overhang adaptor.

Figure 9:
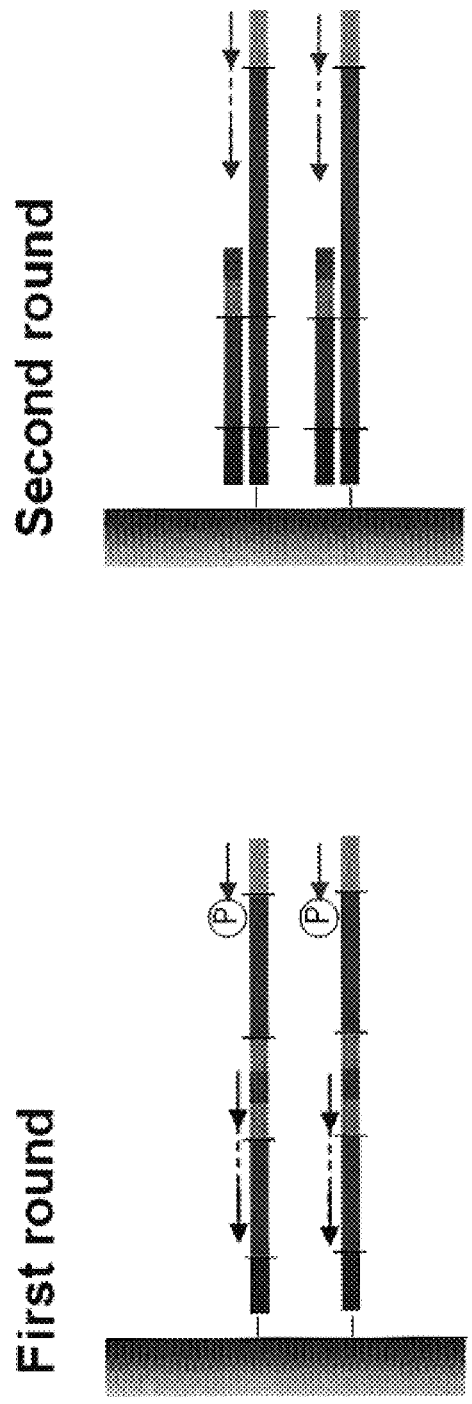

FIG. 9 depicts "tag primed" double-ended sequencing, which is one method for sequencing the products of the invention.

Figure 10:
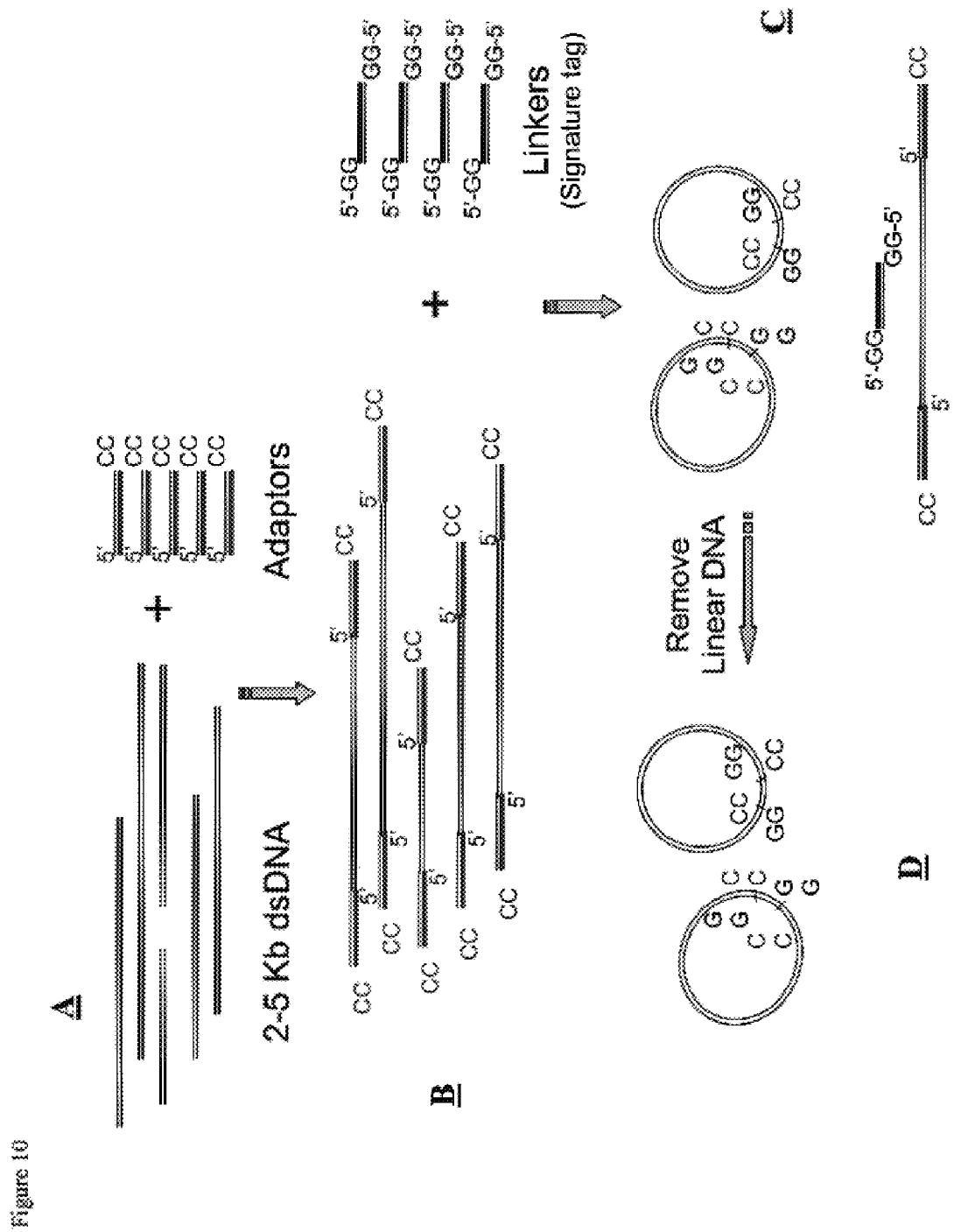

FIG. 10 depicts adaptor linked circularization.

FIG. 11 depicts ssDNA based circularization.

Figure 12:
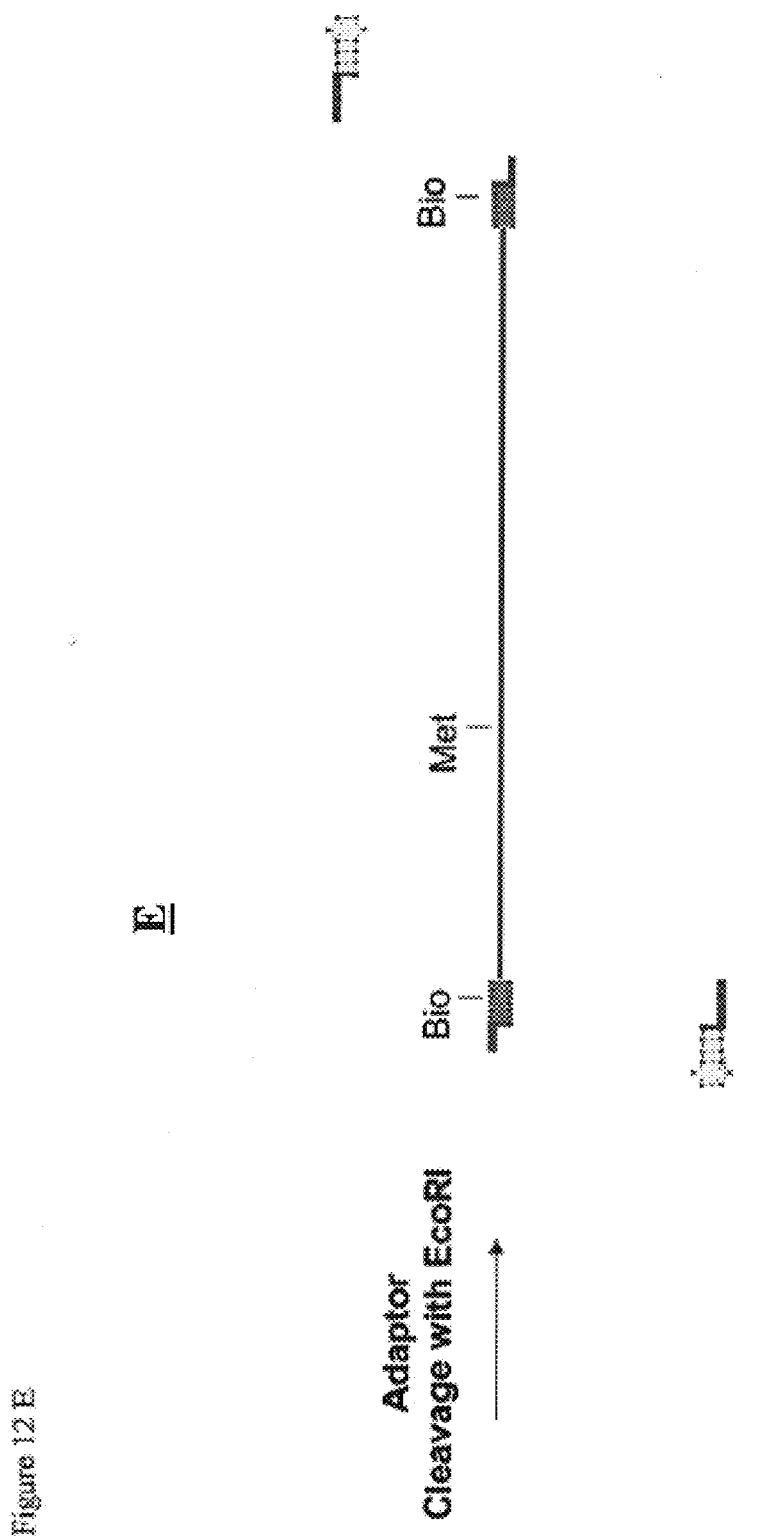
Figure 12:
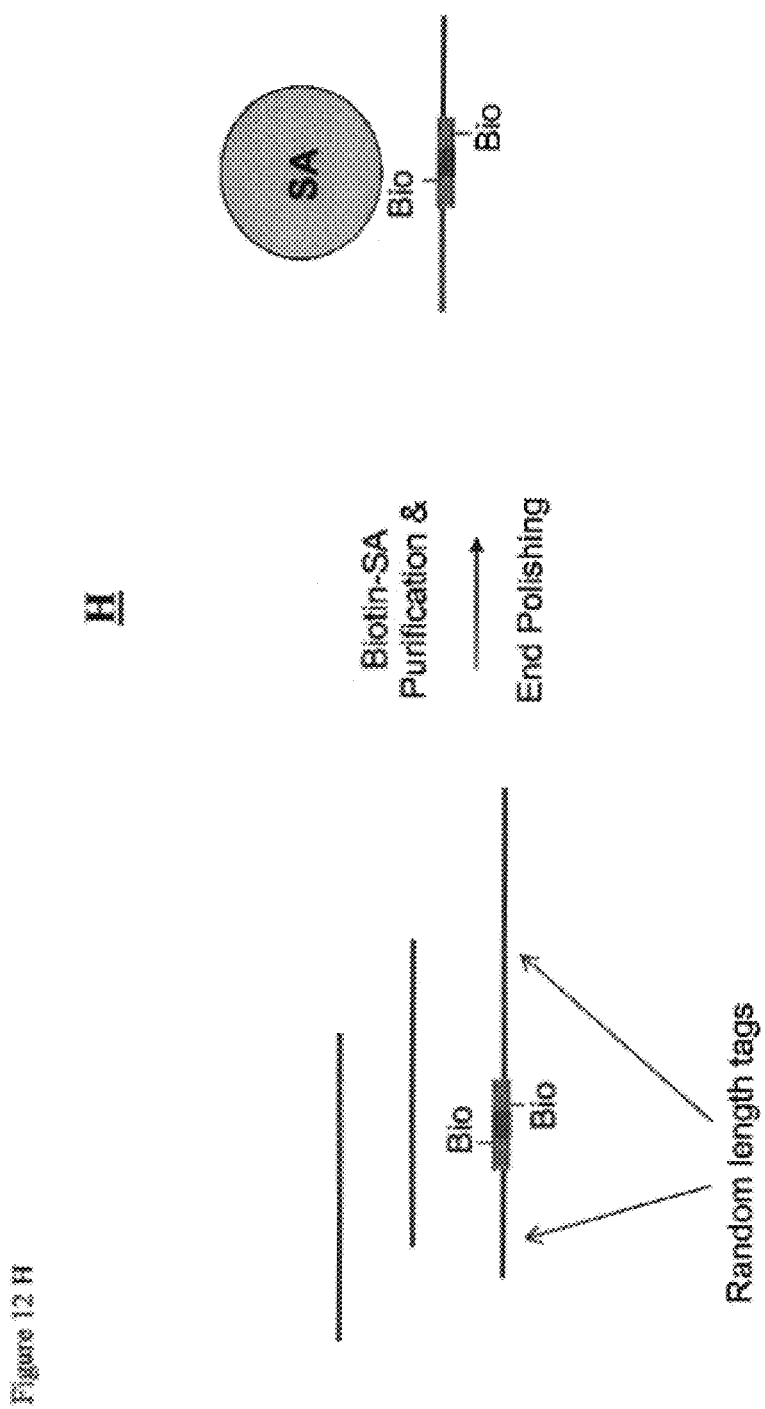
Figure 12:
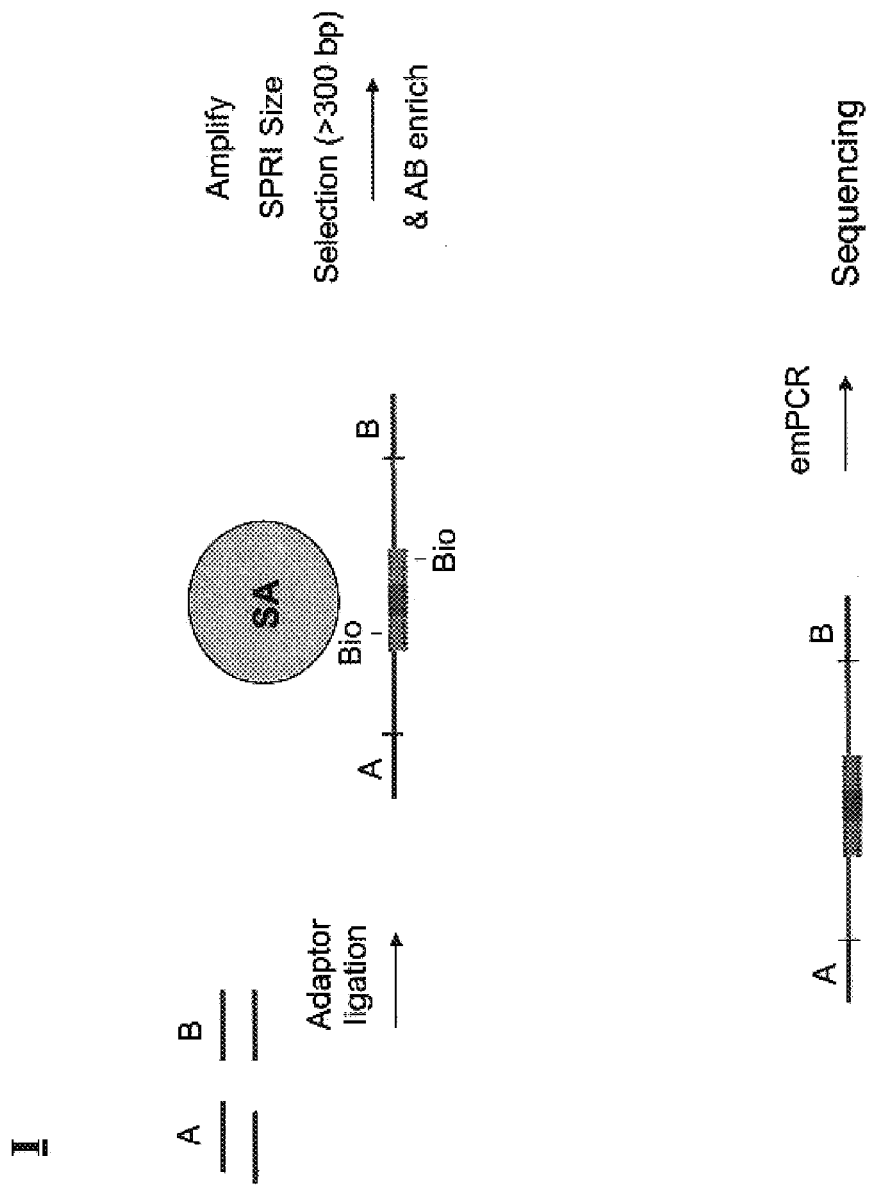

FIG. 12 depicts a schematic representation of another embodiment of the paired-end sequencing strategy—Paired-Reads PET Random Fragmentation. SPRI refers to solid-phase reversible immobilization.

Figure 13:
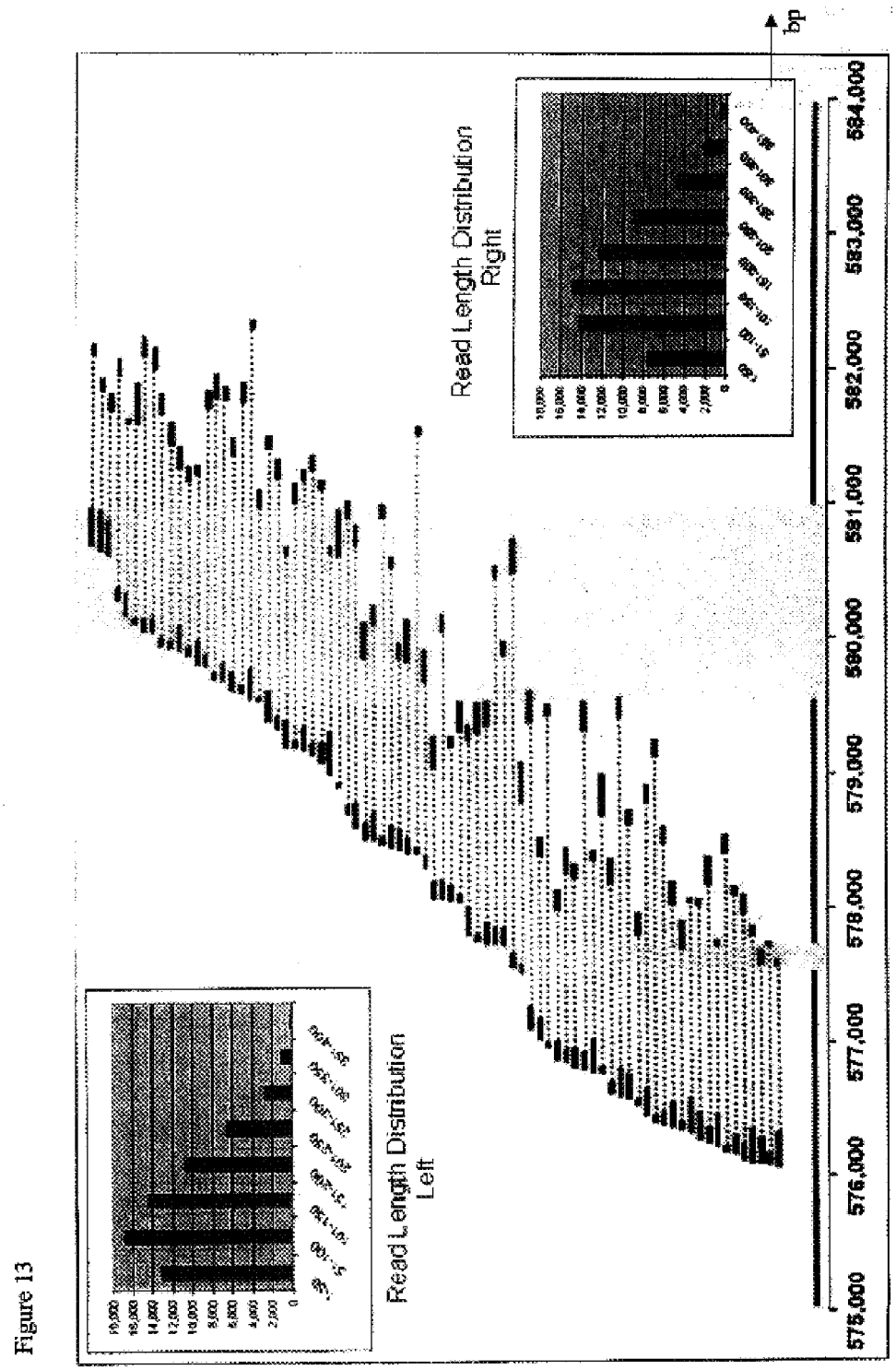

FIG. 13 depicts Paired-Reads PET Random Fragmentation sequencing data from sequencing E. Coli K12.

Figure 14:
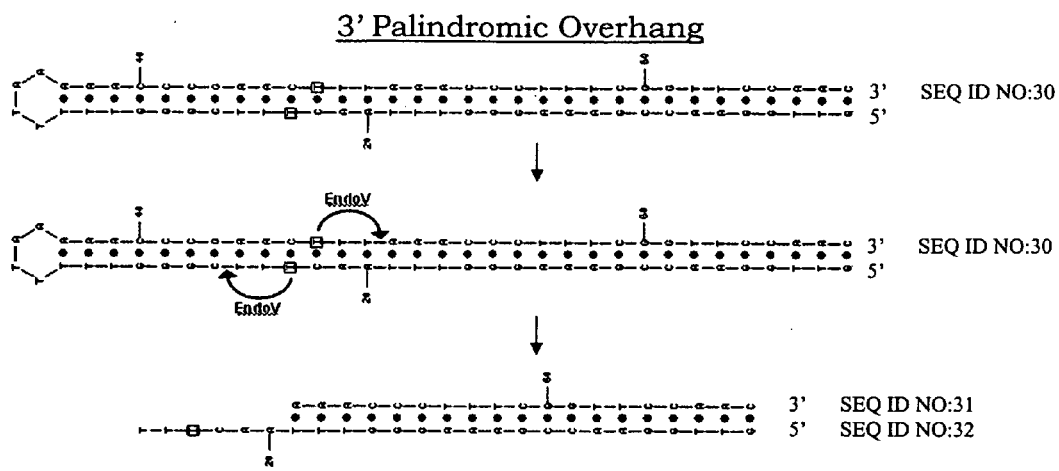
Figure 14:
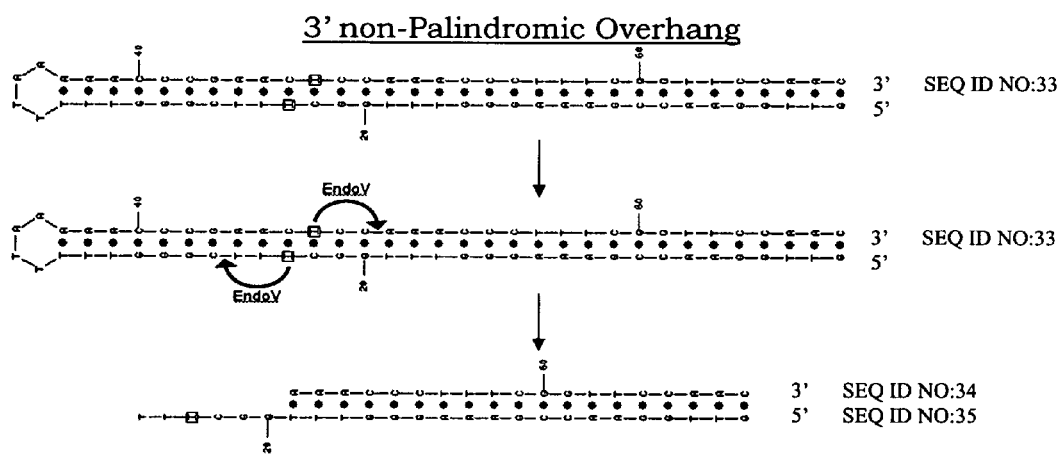
Figure 14:
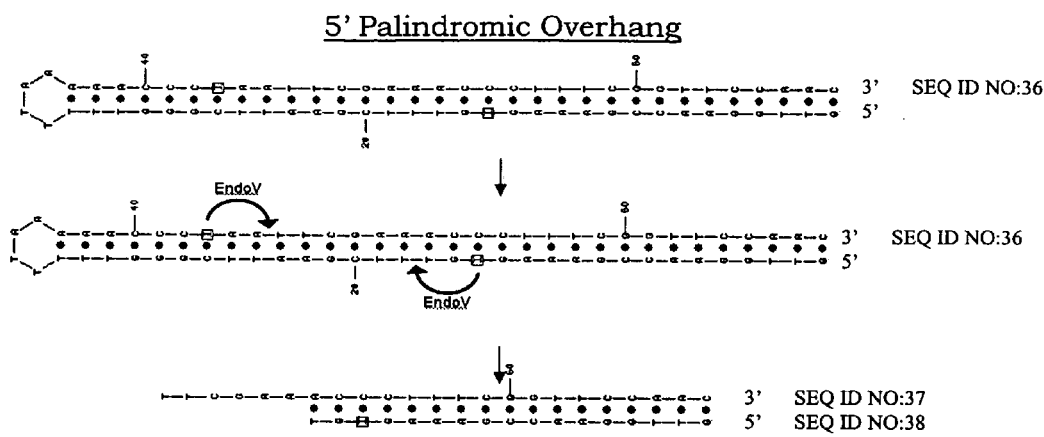
Figure 14:
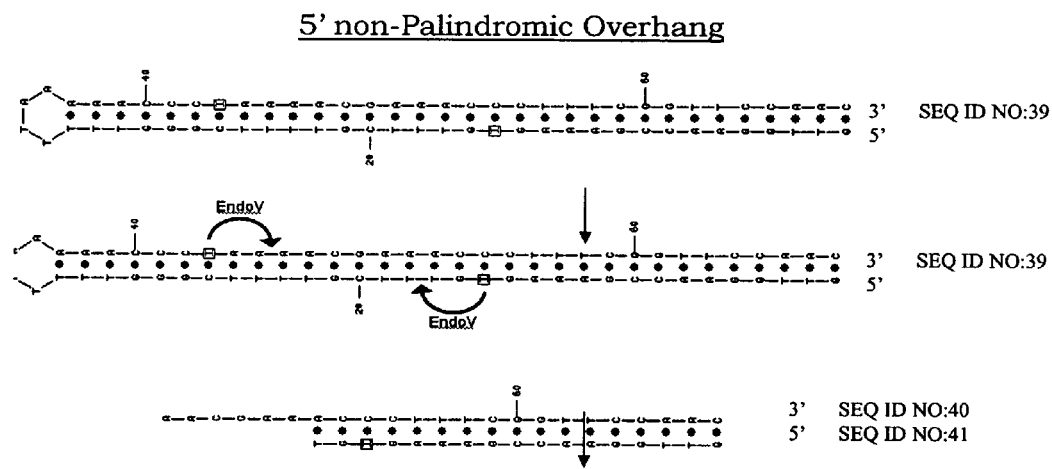
Figure 14:
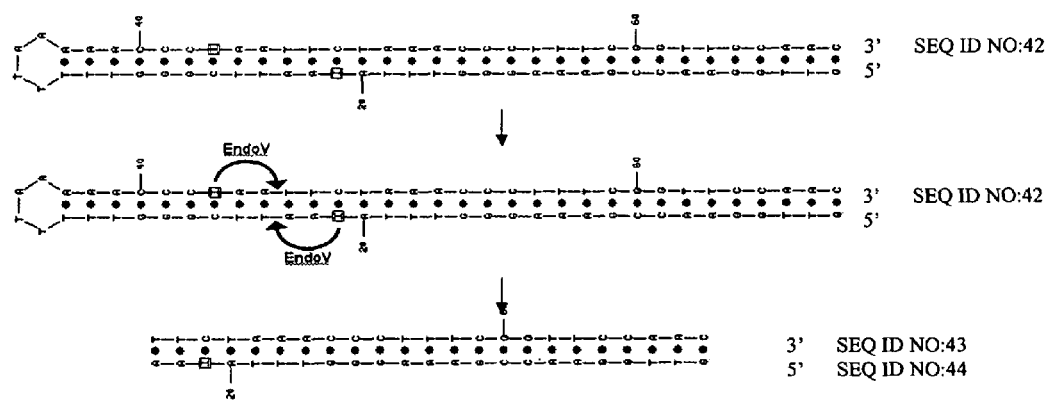

FIG. 14 depicts various methods of double stranded DNA cleavage by E. coli Endonuclease V. The boxed nucleotides "I" represent deoxyinosine.

FIG. 14 A depicts a method in which the nucleotide sequence of the double-stranded DNA directs double-stranded cleavage by E. coli Endonuclease V in a manner which results in a 3' single-stranded palindromic overhang. Note that 3' single-stranded overhangs contain a Deoxyinosine residue.

FIG. 14 B depicts a method in which the nucleotide sequence of the double-stranded DNA directs double-stranded cleavage by E. coli Endonuclease V in a manner which results in a 3' single-stranded non-palindromic overhang. Note that 3' single-stranded overhangs contain a Deoxyinosine residue.

FIG. 14 C depicts a method in which the nucleotide sequence of the double-stranded DNA directs double-stranded cleavage by E. coli Endonuclease V in a manner which results in a 5' single-stranded palindromic overhang. Note that 5' single-stranded overhangs do not contain a Deoxyinosine residue.

FIG. 14 D depicts a method in which the nucleotide sequence of the double-stranded DNA directs double-stranded cleavage by E. coli Endonuclease V in a manner which results in a 5' single-stranded non-palindromic overhang. Note that 5' single-stranded overhangs do not contain a Deoxyinosine residue.

FIG. 14 E depicts a method in which the nucleotide sequence of the double-stranded DNA directs double-stranded cleavage by E. coli Endonuclease V in a manner which results in a blunt end.

Figure 15:
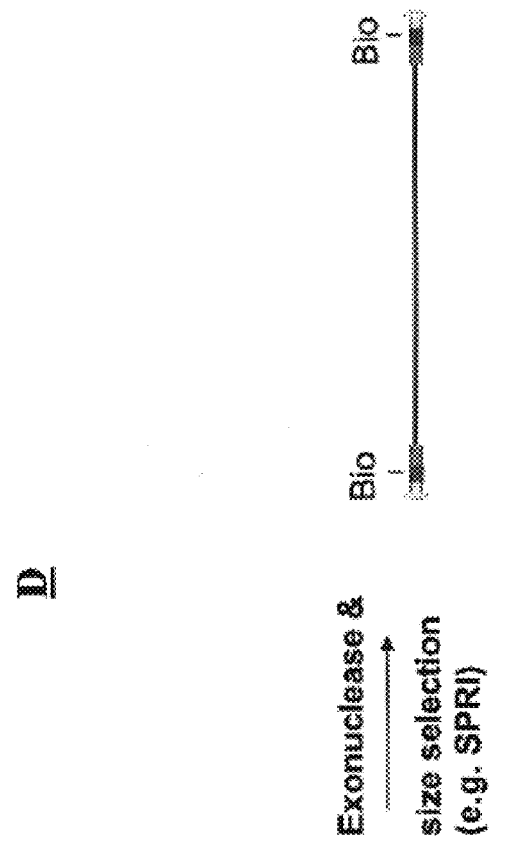
Figure 15:
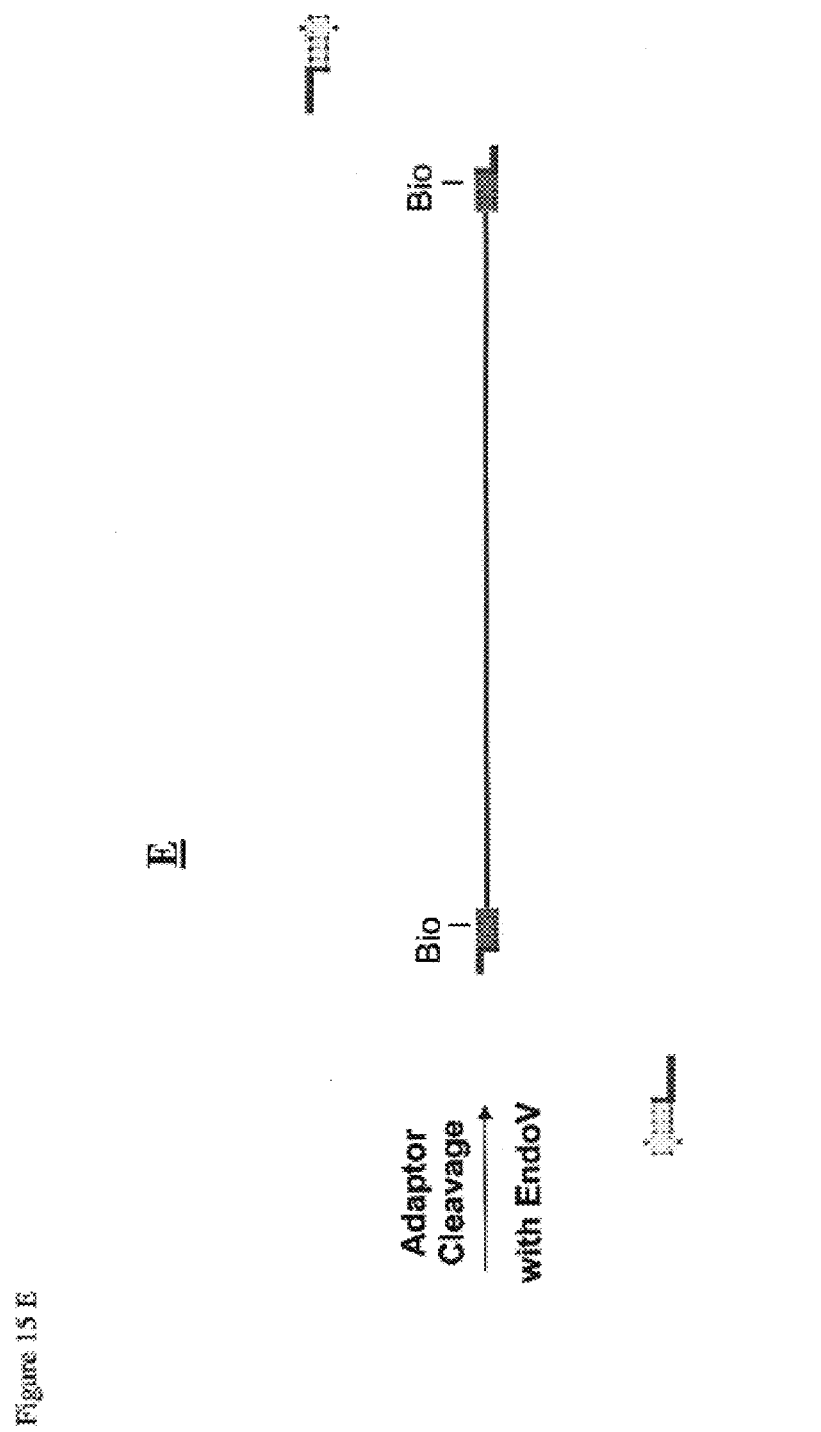
Figure 15:
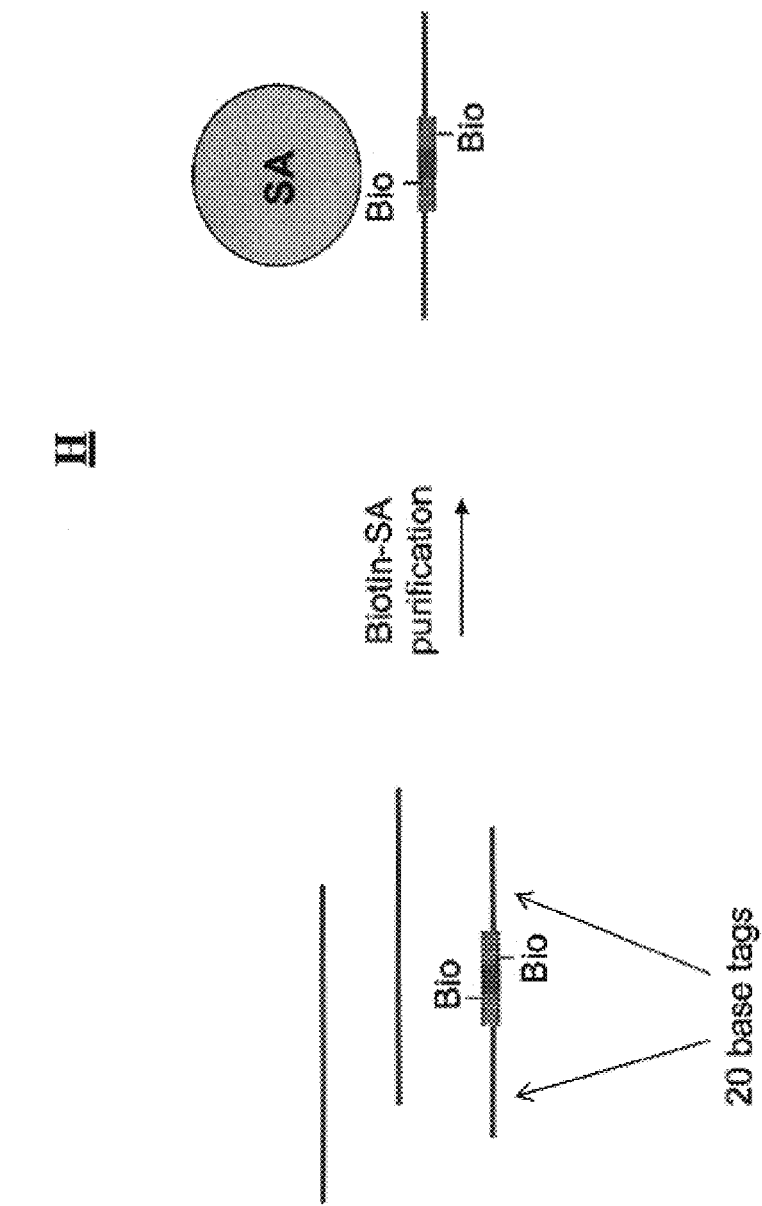
Figure 15:
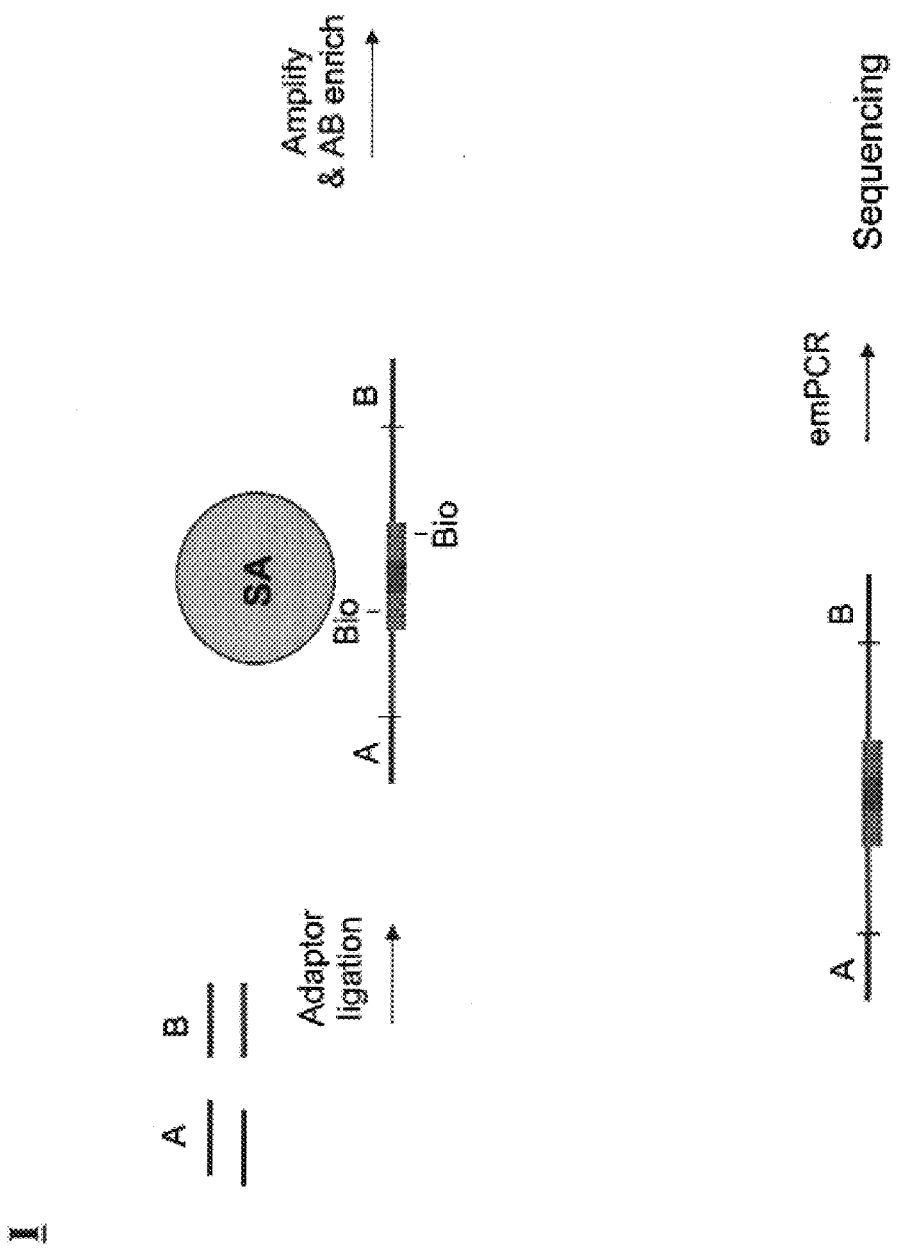

FIG. 15 depicts a schematic representation of another embodiment of the paired-end sequencing strategy with double-stranded cleavage by E. coli Endonuclease V of a hairpin adaptor containing Deoxyinosines on opposing strands (Deoxyinosine Hairpin Adaptor).

Figure 16:
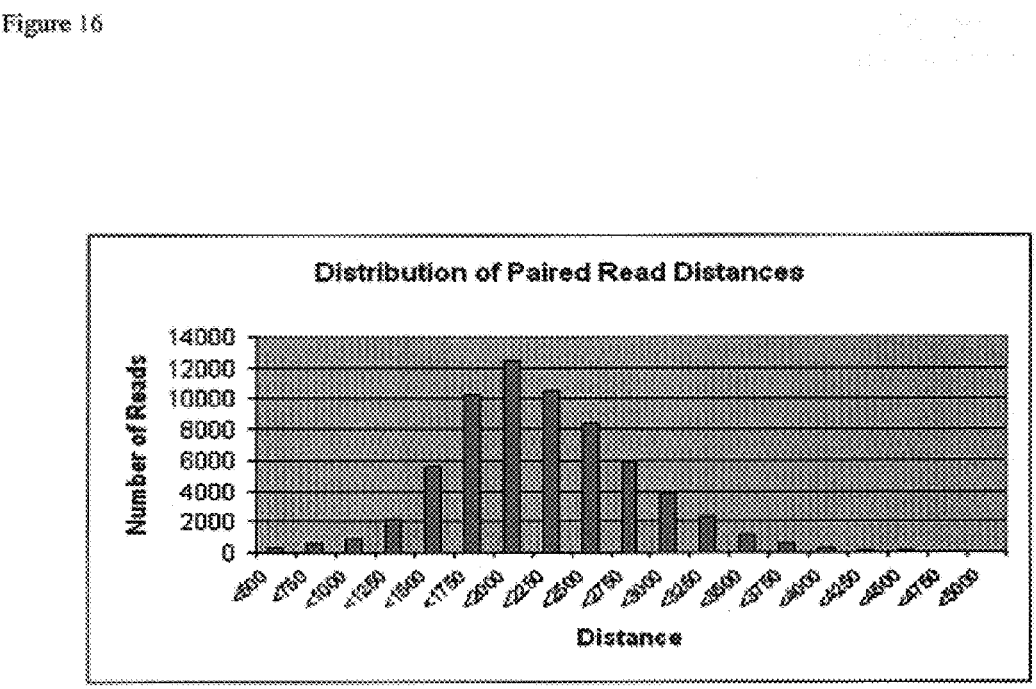

FIG. 16 depicts the distribution of Paired-Read distances obtained from sequencing of E. coli K12 genomic DNA using the Deoxyinosine Hairpin Adaptor method depicted in FIG. 15.

Figure 17:
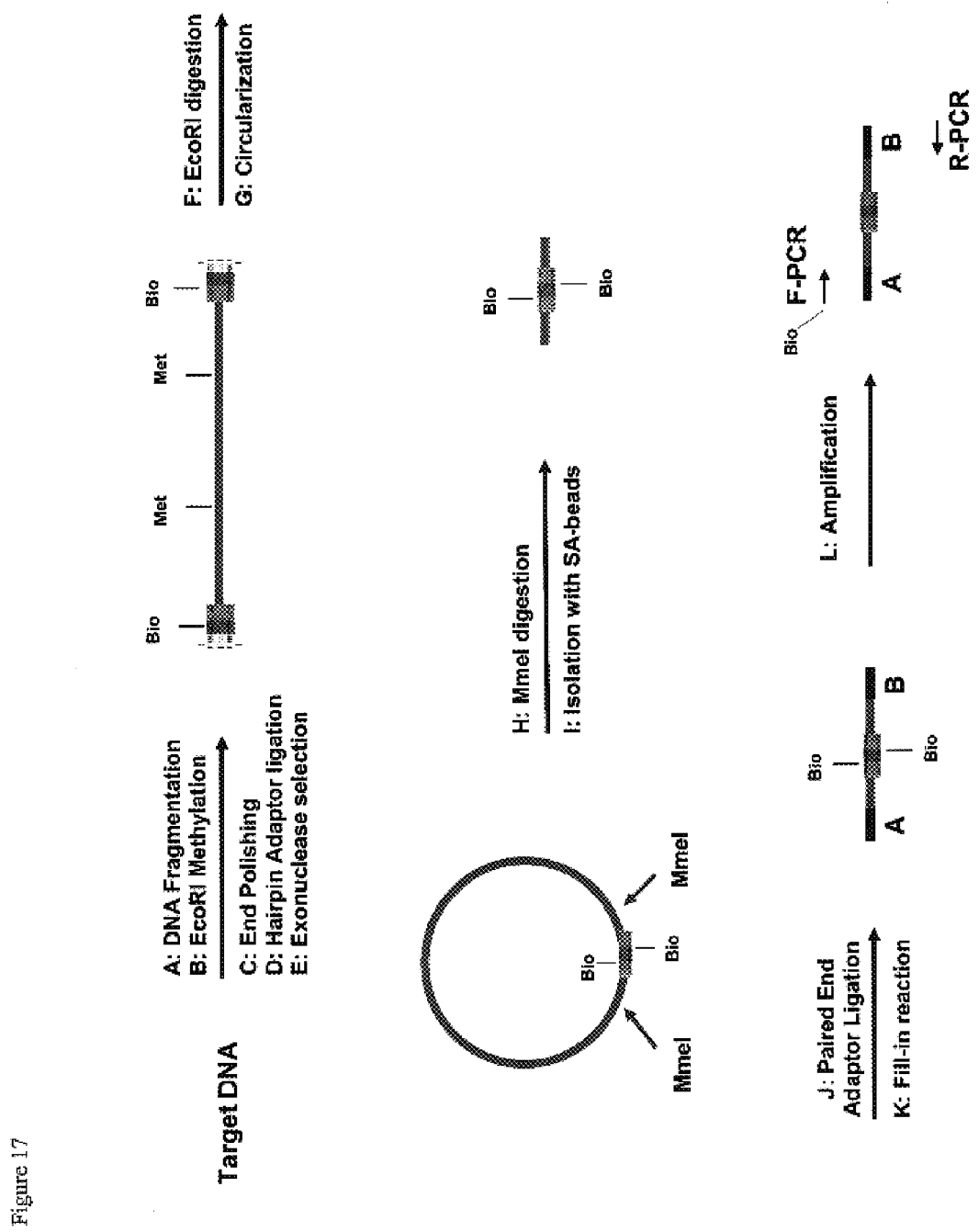

FIG. 17 depicts a schematic representation of another embodiment of the paired end sequencing methods of the invention. Nucleotide sequences of the hairpin adaptor, the paired end adaptors ("A" and "B") and the PCR primer "F-PCR" and "R-PCR" are shown in FIG. 18. Each of the paired end adaptors has double-stranded and single-stranded portions as shown in FIG. 18. "Bio" denotes biotin. "Met" denotes a methylated base. "SA-beads" denotes streptavidin-coated microparticles. "EcoRI" and "MmeI" denote recognition sites for the restriction endonucleases EcoRI and MmeI, respectively.

FIG. 18 depicts the nucleotide sequences and modifications of the adaptor and primeroligonucleotides shown in FIG. 17. FIG. 18 A depicts the hairpin adaptor sequence. "iBiodT" denotes internal biotin-labeled deoxythymine.

"Bio" denotes biotin. "EcoRI" and "MmeI" denote recognition sites for the restriction endonucleases EcoRI and MmeI, respectively.

FIG. 18 B depicts the paired end adaptor and PCR primer nucleotide sequences. Each of the paired end adaptors ("A" and "B") is produced by annealing of two single stranded oligonucleotides, "A top" and "A bottom", "B top" and "B bottom". The 5' ends of the polynucleotide sequences shown in FIG. 18 B are not phosphorylated.

Figure 19:
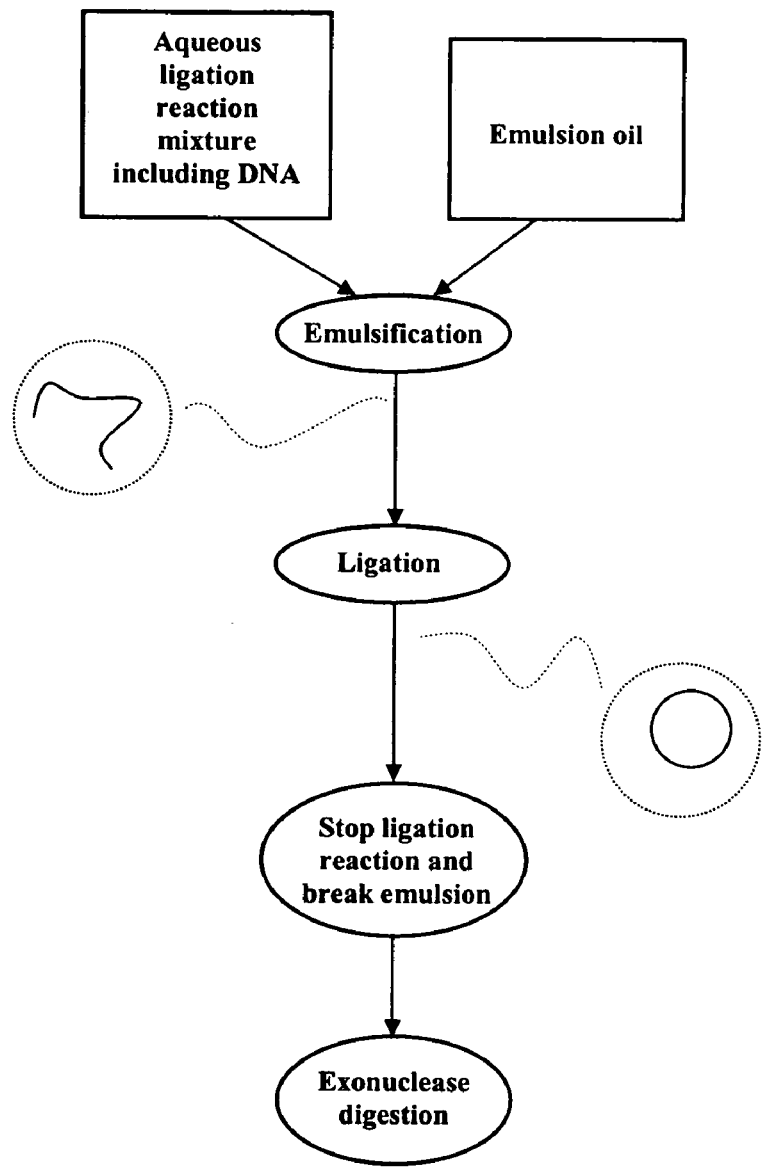

FIG. 19 depicts a schematic representation of one embodiment of a method for polynucleotide ligation in water-in-oil emulsion.

FIG. 20 depicts a graph of the depth of coverage of E. coli K12 genomic DNA achieved by paired end sequencing data obtained with or without MmeI-site containing carrier DNA.

DETAILED DESCRIPTION OF THE INVENTION

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The invention is directed to a fast and cost effective method for isolating and sequencing both ends of a large fragment of nucleic acid. The method is fast and amenable to automation and allows the sequencing and linkage of large fragments of DNA.

Paired end sequencing holds a number of important advantages compared to conventional clone-by-clone shotgun sequencing, and is in fact complementary to it. Foremost among these advantages is the ability to quickly produce a scaffolding of a large genome even when the genome is interspersed with repetitive elements. The method of the invention can be used to produce a library of DNA fragments wherein the fragments contain the ends from a larger fragment of DNA.

First Method

In one embodiment, paired-end sequencing may be performed in the following steps:

Step 1A

The starting material may be any nucleic acid including, for example, genomic DNA, cDNA, RNA, PCR products, episomes and the like. While the methods of the invention are especially effective for long stretches of nucleic acid starting material, the invention is also applicable to small nucleic acids such as a cosmid, plasmid, small PCR products, mitochondrial DNA etc.

The DNA may be from any source. For example, the DNA may be from the genome of an organism whose DNA sequence is unknown, or not completely known. As another example, the DNA may be from the genome of an organism whose DNA sequence is known. Sequencing the DNA of a known genome allows researchers to gather data on genomic polymorphisms and to correlate genotype with disease.

The nucleic acid starting material may be of a known size or known range of sizes. For example, the starting material may be a cDNA library or a genomic library where the average insert size and distribution is known.

Alternatively, the nucleic acid starting material may be fragmented (FIG. 1A) by any one of a number of commonly used methods including nebulization, sonication, HydroShear, ultrasonic fragmentation, enzymatic cleavage (e.g., DNase treatment, including limited DNase treatment, RNase treatment (including limited RNase treatment), and digestion with restriction endonucleases), prefragmented library (such as in a cDNA library), and chemical (e.g., NaOH) induced fragmentation, heat induced fragmentation, and transposon mediated mutation—which can introduce cleavage sites such as restriction endonuclease cleavage sites throughout a DNA sample. See, Goryshin I. Y. and Reznikoff W. S., J Biol Chem. 1998 Mar. 27; 273(13):7367-74; Reznikoff W. S. et al., Methods Mol Biol. 2004; 260:83-96; Oscar R. et al., Journal of Bacteriology, April 2001, p. 2384-2388, Vol. 183, No. 7; Pelicic, V. et al., Journal of Bacteriology, October 2000, p. 5391-5398, Vol. 182.

Some fragmentation methods, such as nebulization, can produce a population of target DNA fragments which differ in size by a factor of only 2. Other fractionation methods, such as restriction enzyme digestion produce a wider range of sizes. Still other methods, such as HydroShearing, may be favored if large nucleic acid fragments are desired. In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes. Additional methods for preparing nucleic acid starting materials may be found in International Patent Application No. WO04/070007, which is hereby incorporated by reference in its entirety.

Depending on the fragmentation method employed, the DNA ends may require polishing. That is, the double stranded DNA ends may need to be treated to make them blunt ended and suitable for ligation. This step will vary in an art known manner depending on the fragmentation method. For example, mechanical sheared DNA can be polished using Bal31 to cleave the sequence overhangs and a polymerase such as klenow, T4 polymerase, and dNTPs may be used to fill in to produce blunt ends.

Step 1B

When the sizes of the fragments are more varied than desired, the nucleic acid fragments may be size fractionated to reduce this size variation.

Size fractionation is an optional step that may be performed by a number of art known methodologies. Methods for size fractionation include gel methods such as pulse gel electrophoresis, and sedimentation through a sucrose gradient or a cesium chloride gradient, and size exclusion chromatography (gel permeation chromatography). The choice of selected size range will be based on the length of the region to be spanned by paired-end sequencing.

Figure 1K:
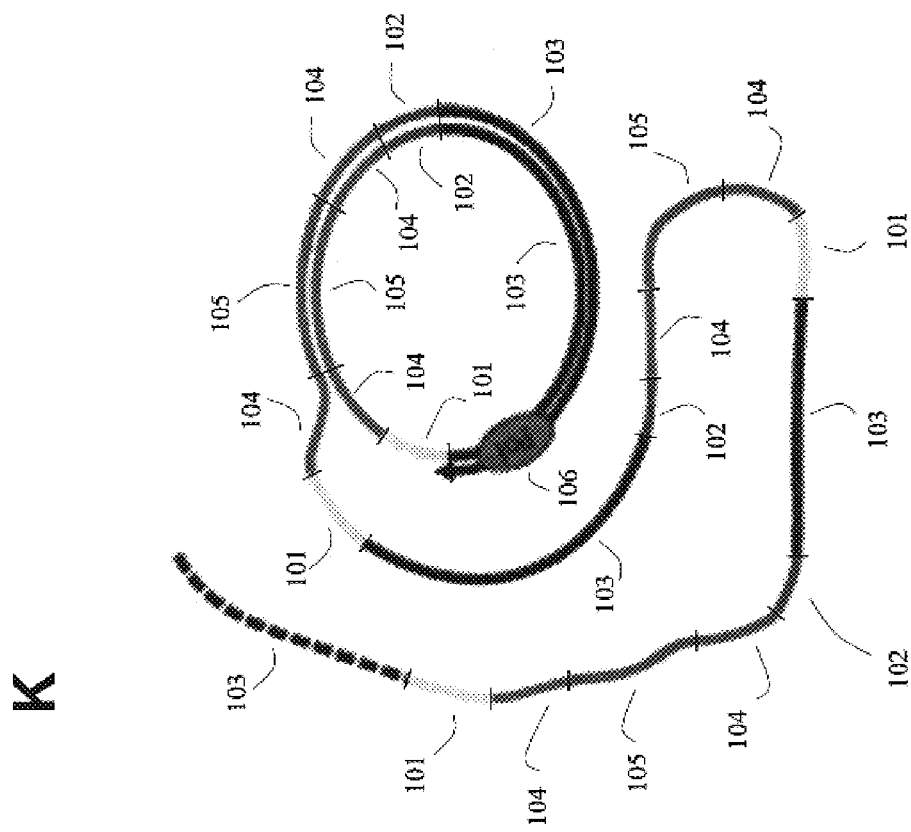
FIG. 1 depicts a schematic representation of one embodiment of the paired-end sequencing strategy. The numeric labels indicate the origin of the nucleic acids. "101" denotes one flanking region of the capture element, shown for example, on the left side of FIG. 3A. "102" denotes a second flanking region of the capture element, shown for example, on the right side of FIG. 3A. "103" denotes the capture element. "104" denotes fragmented (and optionally size fractionated) starting nucleic acid. "105" denotes a separator element. "106" denotes polymerase.

One preferred technique for size fractionation is gel electrophoresis (See FIG. 1B). In a preferred embodiment, size fractionated DNA fragment has a size distribution, which is within 25% of each other. For example, a 5 Kb size fraction would comprise fragments which are 5 Kb+/−1 kb (i.e., 4 Kb to 6 Kb) and a 50 Kb size fraction would comprise fragments which are 50 Kb+/−10 kb (i.e., 40 Kb to 60 Kb).

Step 1C

In this step, a "capture element" is prepared. A capture element is a linear double stranded nucleic acid—which may have single stranded ends or double stranded ends used for ligating the nucleic acid fragment from the previous step. A "capture element" may be propagated as a circular nucleic acid (e.g., a plasmid as depicted in FIG. 1C) which contains forward and reverse adaptor ends (depicted in FIG. 1C as a thick region of the circle). This circular plasmid may be cleaved before the capture element is used. These adaptor ends contain nucleic acid sequences that can serve as hybridization sites for potential PCR primers and sequencing primers in subsequent steps.

Between the two adaptor ends the capture element may comprise additional elements such as restriction endonuclease recognition and/or cleavage sites, antibiotic resistance markers, prokaryotic or eukaryotic origins of replication or a combination of these elements. Examples of such antibiotic resistance markers include, without limitation, genes imparting resistance to ampicillin, tetracycline, neomycin, kanamycin, streptomycin, bleomycin, zeocin, chloramphenicol, among others. Prokaryotic origins of replication can include, among others, OriC and OriV. Eukaryotic origins of replication can include autonomously replicating sequences (ARS), but are not limited to these sequences. In addition, the capture element may contain restriction endonuclease recognition and/or cleavage sites (e.g., unique and rare sites are preferred) that can be used to digest subsequent nucleic acid products (step L) into small amplifiable (by PCR) fragments. Capture elements can also comprise markers or tags, such as biotin, for easy purification or enrichment of the nucleic acid for paired-end sequencing.

Step 1D

The capture element is linearized using known techniques such as restriction endonuclease digestion (blunt or sticky ends can be used for different fragment preparation; see below and FIG. 1 D). To prevent concatemer formation (i.e., the ligation of multiple capture elements to each other) the capture element can be dephosphorylated or modified with topoisomerase for TA cloning.

Step 1E

The capture element is ligated to the fragment (or size fractionated fragment) of step A or B to form a circular nucleic acid comprising one capture element and one fragment of the target DNA (FIG. 1 E). The capture element and the target DNA are joined by well-known methodologies such as ligation by DNA ligase or by topoisomerase cloning strategies.

Step 1F

The result of the previous step yields a collection of capture elements ligated to a DNA fragment which can be of considerable size. The present step is used to delete a large internal region of the target DNA fragment to yield a cloned insert of a size that can be more amenable for automated DNA sequencing (FIG. 1 F).

In this step, the captured genomic DNA (i.e., the circular nucleic acid produced by step E) is digested with one or more restriction endonucleases which may have one or more cleavage sites within the genomic DNA. In general, any restriction endonuclease may be used for "internal cleavage" as long as the restriction endonuclease does not cut within the capture element. Internal cleavage refers to the cleavage that is internal to the target DNA and which does not cut the capture element. Internal cleavage restriction enzymes may be selected by designing the capture element so that it does not contain the cleavage sites of selected restriction endonucleases. Restriction endonucleases and their use are well known in the art and can readily be applied to the present method. In addition, a combination of multiple restriction enzymes, each restricted to internal cleavage, may be employed to further reduce the size of the target DNA fragment.

In a preferred embodiment, the genomic DNA is cut by one or more of these restriction endonucleases to within 50 to 150 bases of the capture element.

Step 1G

In this step, a "separator element" which is a double stranded nucleic acid of known sequence is ligated between the ends of the digested genomic material of the previous step to form a circular nucleic acid (FIG. 1 G). This "separator element" serves two purposes. First, the separator element can comprise a priming site for rolling circle amplification of the minicircles (see below, step I). Second, since the sequence of the separator element is known, it can act as an identifier that marks the ends of the paired genomic ends (to enable trimming and easy software analysis of the linked ends). That is, during subsequent sequencing of the genomic fragment, the sequence of the separator element would signal that the entire genomic fragment has been sequenced. Such separator elements can also comprise additional elements such as restriction endonuclease recognition and/or cleavage sites, antibiotic resistance markers, prokaryotic or eukaryotic origins of replication or a combination of these elements. The optional presence of such elements as antibiotic resistance markers and origins of replication notwithstanding, one of the advantages of the methods of the present invention is that said methods do not require the use of host cells (e.g. *E. coli*) for the cloning, amplification or other manipulations of nucleic acids. The separator element can also be biotinylated or otherwise tagged with a marker or a tag for easy purification or enrichment of the nucleic acid for paired-end sequencing.

Step 1H

The circular nucleic acid (i.e., minicircle) produced from the last step is rendered single-stranded to result in a single stranded nucleic acid. This is done using standard DNA denaturing techniques by changing salt, temperature or pH of the solution. Other DNA denaturing techniques are known to one of skill in the art. After denaturing, the DNA circles from the same minicircle may still be linked but this does not affect the methods of the invention (FIG. 1 H).

Step 1I

A primer is annealed to the separator element which comprises sequence that can anneal to the primer. This separator sequence thus acts as initiator for rolling circle amplification (FIG. 1 I).

Step 1J

The sample is amplified by rolling circle amplification to generate long single-stranded products (FIG. 1 J). One advantage of this rolling circle amplification step is that elements without a separator element will not amplify and elements that are not closed circles will amplify poorly.

Step 1K

One or more capping oligos are annealed to single-stranded restriction sites that flank the forward and reverse adaptor (rendering them double stranded in these regions) (FIG. 1 L). The capping oligos may be complementary to at least part of the capture element, to at least part of the adaptor regions, or both.

Step 1L

The capped single-stranded DNA is cut at the capped sites into small fragments (FIG. 1 M). These small fragments which have ends of known sequence and can be easily amplified using conventional amplification techniques such as PCR.

Second Method

In a second embodiment, paired-end sequencing may be performed in the following steps:

Step 2A—Fragmentation of Sample DNA

The fragmentation of target nucleic acid and size fractionation is the same as for the previous embodiment.

Step 2B—Methylation and End Polishing.

If desired, the fragmented target nucleic acid may be methylated by any methylase. Preferred methylase would be those that influence restriction endonuclease digestion. Methylases may be used in at least two different strategies. In one preferred embodiment, methylases enable cleavage by restriction endonucleases that cleave only at a methylated restriction site. In another preferred embodiment, methylases prevent cleavage by restriction endonucleases that only cleave unmethylated DNA.

The step of end polishing is the same as described in the first method.

Step 2C—Ligation of Tag Adaptors

In this step an adaptor is ligated to the ends of the target nucleic acid fragments (FIG. 2, I.) to produce a fragment with an adaptor at both ends. The adaptors may be of any size but a size of 10 to 30 bases is preferred, and a size of 12 to 15 bases is more preferred. To prevent the formation of concatemers of adaptors and/or target nucleic acid fragments, the adaptors may comprise a blunt end and an incompatible sticky end (i.e., an end with a 5' overhang or 3' overhang). After the adaptors are ligated to the DNA fragment and ligase has been removed, the sticky ends may be filled in with polymerase and dNTPs.

The adaptors of this section may be a capture fragment. Examples of capture fragments are shown in FIGS. 4 and 5.

To prevent concatemer formation, the adaptors may be hairpin adaptors (FIG. 6A). The use of hairpin adaptors (e.g., FIG. 6) prevents concatemer formation because hairpin adaptors cannot form any multimers greater than a dimer. Another method for preventing concatemers is to use adaptors where the 5' end of one or both strands is not phosphorylated.

Other adaptors that may be used include non-phosphorylated adaptors which have the advantage of using fewer processing steps but which also requires a phosphorylation step using a kinase.

As discussed elsewhere in this disclosure, the adaptors may be methylated, or biotinylated or both.

Step 2D—Exonuclease Digestion and Gel Purification

DNA fragments which are ligated to two hairpin adaptors may be purified using exonucleases. This exonuclease purification takes advantage of the fact that a double stranded DNA, ligated to a hairpin adaptor on both ends, is a DNA molecule without an exposed 5' or 3' end. Other DNAs in the ligation mixture, such as a double stranded DNA fragment ligated to only one hairpin adaptor, an unligated DNA fragment and unligated adaptors are susceptible to exonucleases (FIG. 6 B). Thus, exposure of the ligation mixture to an exonuclease will remove most DNA except for DNA fragments ligated to two hairpin adaptors and hairpin adaptor dimers. Since the hairpin adaptor dimers are significantly smaller that the DNA fragments, they can be removed using known techniques such as a size fractionation column (e.g., spin column) or agarose or acrylamide gel electrophoresis, or one of the other polynucleotide size discriminating methods known in the art and/or discussed elsewhere in this disclosure.

In one embodiment, the adaptors may be biotinylated to facilitate isolation/enrichment of tag carrying fragments.

In another embodiment, fragments containing the adaptor may be purified by annealing a capture oligonucleotide, complementary to the tag sequence, to the fragments.

Step 2E—Preparation of Fragments for Circularization

Following the addition of adaptors to both ends of the target nucleic acid fragment, the fragment is circularized.

To prepare the target nucleic acid for self circularization, cleavage in the adaptor regions may be desirable for a number of reasons. For example, if hairpin adaptors are used, the DNA fragment will not self circularize because there are no free 5' or 3' ends. As another example, if the adaptors leave the DNA fragment with blunt ends, cleavage would allow the adaptors to have 5' or 3' overhangs and these overhangs (so called "sticky ends") greatly facilitate ligation efficiency. Furthermore, digestion in the adaptor region would allow selection of DNA fragments with two adaptors, one ligated at each end. This is because the adaptors can be designed such that cleavage with a restriction endonuclease would leave compatible sticky ends. After cleavage in the adaptor region, DNA fragments with only one adaptor (an undesirable species) would have one sticky end and one blunt end and would have difficulty in self circularization. Thus, only DNA fragments with adaptors at both ends would be circularized.

Limiting cleavage to the adaptors may be accomplished with a number of methods. In one method, the adaptors are methylated and is ligated to unmethylated DNA. Then the construct is digested with a restriction endonuclease which only cleave methylated DNA. Since only the adaptors are methylated, only the adaptors will be cleaved.

In another method, the DNA fragments may be methylated and the adaptors are not methylated. Cleavage with a restriction endonuclease which only recognize and cleave unmethylated DNA will limit cleavage to the adaptors. This may be accomplished by using starting DNA which is already methylated, or by in vitro methylation.

It is understood that in some circumstances, digestion of the adaptors is not required. For example, if the fragment from the previous steps comprises blunt ends only, then digestion of the adaptors may be optional.

It is also understood that the DNA fragments may be treated to facilitate ligation/circularization. For example, if the adaptors are blocked, or do not contain a 5' phosphate, the blocking group may be removed or the phosphates may be added to make the fragment ready for ligation.

Step 2F Ligation of Ends to Form Circularized Fragment.

A number of methods may be used for circularization.

In one embodiment, ligase is added to the reaction mixture with the appropriate ligase buffer and the DNA fragments are allowed to recircularize.

In one embodiment, ligations are performed at dilute DNA concentrations to promote self ligation and to discourage the formation of concatemers.

In another embodiment, ligations are performed in water-in-oil emulsions, wherein the aqueous droplets contain approximately one fragment to be circularized, as described elsewhere in this disclosure.

Figure 2:
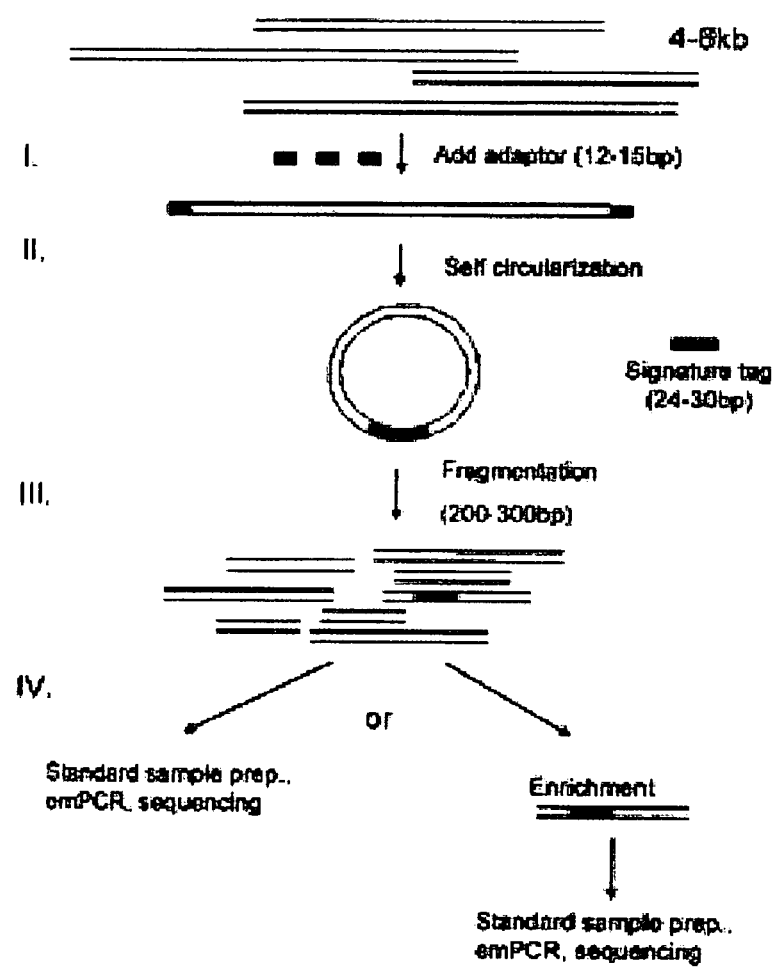
FIG. 2 depicts a schematic representation of a second embodiment of the paired-end sequencing strategy.

In one embodiment, a signature tag is ligated to the target nucleic acid fragment and the fragment is self circularized (see FIG. 2). The signature tag is a double stranded nucleic acid sequence of between 24 to 30 basepairs. This "signature tag" is similar to the "separator element" of the previous embodiment in that it can act as an identifier that marks the ends of the paired genomic ends (to enable trimming and easy software analysis of the linked ends). During subsequent sequencing of the genomic fragment, the sequence of the signature tag signals the boundary between the two ends of the target nucleic acid sequence.

Step 2G

Following the addition of the signature tag and self-circularization, the target nucleic acid fragment is further digested or fragmented. Fragmentation may be performed using any fragmentation procedure listed in this disclosure. See, for example, Step 1A above. Alternatively, one or more restriction endonucleases may be used to digest the target DNA to produce fragments.

In one preferred embodiment, a nebulizer is used to fragment the nucleic acids until the average fragment size is about 200 to 300 bps. As shown in FIG. 2, some of these fragments would contain a signature tag while other fragments would not contain a signature tag.

At this point, the nucleic acid fragments may be sequenced using standard techniques. Methods for sequencing nucleic acid fragments are known. One preferred method of sequencing is described in International Patent Application No. WO 05/003375 filed Jan. 28, 2004.

Step 2H

In an optional step, fragments containing the signature tag may be enriched from fragments without signature tags. One method for enrichment involves the use of biotinylated signature tags in the sample preparation step. After fragmentation, fragments that contain the signature tag would be biotinylated and may be purified using a streptavidin column or streptavidin beads in solution.

Following enrichment, the nucleic acid fragments may be sequenced using standard techniques including automated techniques such as those described in International Patent Application No. WO 05/003375, filed Jan. 28, 2004.

Third Method

Paired end sequencing may be performed by a third method.

Steps 3A to 3E.

In this method, step A to step E may be performed as described in the second method (i.e., as steps 2A to 2E). Furthermore, in the third method each adaptor comprises a type IIS restriction endonuclease site which can direct DNA cleavage about 15 to 25 bps away from the restriction endonuclease recognition site. It is known that different type IIS restriction endonucleases cut at various distances from the endonuclease recognition site and the use of different type IIS restriction endonucleases to adjust this distance is contemplated.

Step 3F Ligation of Ends to Form Circularized Fragment.

Step 3F may be performed according to the second method (step 2F) with the exception that a signature tag is not used (See FIG. 6D).

Optional Enrichment Step

In any of the methods of the invention, an exonuclease may be used following ligation to remove non-circularized fragments and to reduce the presence of concatemerized fragments. Since a properly recircularized DNA fragment has no exposed 5' or 3' ends, it is resistant to exonuclease digestion. Further, a concatemer, being larger, would have a higher chance of having exposed 5' or 3' ends due to nicks. Exonuclease treatment would also remove these concatemers with nicks.

Optional Rolling Circle Amplification

The circularized DNA may be amplified by rolling circle amplification. Briefly, an oligonucleotide may be used to hybridize to one strand of the recircularized DNA. This oligonucleotide primer is extended with a polymerase. Since the template is a circle, the polymerase will generate a single stranded concatemer having multiple repeats of the target DNA. This single stranded concatemer may be made double stranded by hybridizing a second primer to it and elongating from this second primer. For example, this second primer may be complementary to the adaptor sequence of this single stranded concatemer). The resulting double stranded concatemer may be used directly for the next step.

Step 3G Digestion/Fragmentation of DNA.

In this step, the circularized nucleic acid or the concatemerized nucleic acid from rolling circle amplification is digested with a Type IIS restriction endonuclease (FIG. 6 D). As stated for step 3A, each adaptor contains at least one type IIS restriction endonuclease cleavage site. A type IIS restriction endonuclease will recognize the type IIS restriction endonuclease cleavage site on the adaptor and cleave the nucleic acid about 10 to 20 basepairs away. Examples of type IIS restriction endonuclease include MmeI (about 20 bp), EcoP15I (25 bp) or BpmI (14 bp).

This step will produce short fragments (10 to 100 bp) of DNA comprising two ends of a larger DNA fragment, with an adaptor region between the two ends (FIG. 6E). An alternative method for producing the same structure is to randomly fragment the circularized nucleic acid using any of a number of DNA fragmenting methods as described in elsewhere in this disclosure (e.g., as described in step 1A). This would allow fragments of any size (100 bp, 150 bp, 200 bp, 250 bp, 300 bp or more) to be made.

With either method, other DNA fragments without an adaptor region in the middle are also produced (FIG. 6E). However, since the adaptor region is biotinylated, DNA comprising adaptor regions may be selectively purified using a solid support with an affinity for biotin such as, for example, streptavidin beads, avidin beads, BCCP beads and the like.

Step 3H. Sequencing

The products of any of the methods of the invention may be sequenced manually or by automated sequence techniques. Manual sequencing by such methods as Sanger sequencing or Maxam-Gilbert sequencing is well known. Automated sequencing may be performed, for example, by using the automated sequencing method as the 454 Sequencing™ developed by 454 Life Sciences Corporation (Branford, Conn.) which is also described in application WO/05003375 filed Jan. 28, 2004 and in copending US patent applications U.S. Ser. No. 10/767,779 filed Jan. 28, 2004, U.S. Ser. No. 60/476,602, filed Jun. 6, 2003; U.S. Ser. No. 60/476,504, filed Jun. 6, 2003; U.S. Ser. No. 60/443,471, filed Jan. 29, 2003; U.S. Ser. No. 60/476,313, filed Jun. 6, 2003; U.S. Ser. No. 60/476,592, filed Jun. 6, 2003; U.S. Ser. No. 60/465,071, filed Apr. 23, 2003; and U.S. Ser. No. 60/497,985; filed Aug. 25, 2003.

Briefly, in an automated sequencing procedure such as the sequencing procedure developed by 454 Life Sciences Corp., one sequencing adaptor (sequencing adaptor A) may be ligated to one end of the DNA fragment and a second sequencing adaptor (sequencing adaptor B) may be ligated to a second end of the DNA fragment. Following ligation, the DNA fragment may be purified away from any unligated sequencing adaptors by binding the biotin to a solid support. The isolated nucleic acid fragments may be placed in individual reaction chambers and further amplified by PCR using primers specific for sequencing adaptor A and sequencing adaptor B. By attaching a biotin moiety to either A or B adaptor single stranded DNA which preferentially consists of the A-B fragments can be isolated. This amplified nucleic acid may be sequenced using sequencing primers specific for sequencing adaptor A, sequencing adaptor B or a sequencing primer specific for the adaptor (e.g., hairpin adaptor) located in between the two ends.

Once a plurality of these fragments, comprising the ends of a larger DNA fragment, are prepared, they can be sequenced and the paired-end sequence information can be assembled to generate a partial or complete sequence map of a genome.

Fourth Method

Paired end sequencing may be performed using a variation of the above described method called Paired-Reads PET Random Fragmentation as outlined in FIG. 12. Results from an experiment according to this fourth method are depicted in FIG. 13.

Steps 4A to 4E

In this method, steps A to step D may be performed as described in the second method or third method (i.e., as steps 2A to 2D or steps 3A to 3D). As an alternative, step 4D may be performed using SPRI (solid-phase reversible immobilization) to purify exonuclease treated fragments. For example, the nucleic acid fragments in FIG. 12 are ligated to biotinylated primers and can be purified for example using streptavidin, avidin, reduced affinity streptavidin or reduced affinity avidin coated beads.

Step 4E may be performed as described in step 2E or step 3E.

Step 4F may be performed as described in step 3F. Briefly, the linear DNA fragment generated in the last step may be circularized using any known method of circularization as described above for steps 2F or step 3F.

In addition, an optional enrichment step, as described in Step 3F above, may be performed to enrich for circular nucleic acids. Briefly, nucleic acids that are not circularized may be removed by anexonuclease which degrade nucleic acids with free ends. Covalently closed circular nucleic acids do not have free ends and are resistant to exonuclease attack. Because of this, treatment with an exonuclease would enrich for circular nucleic acid while removing linear nucleic acids.

Step 4G

Following self circularization, fragmentation may be performed using any fragmentation procedure listed in this disclosure. One preferred method is to fragment the circular nucleic acids using mechanical shearing. Mechanical shearing may be performed for example, by vortexing, by forcing nucleic acid in solution through a small orfice, or other similar procedure described elsewhere in this disclosure. One advantage of mechanical shearing is that nucleic acids of different lengths may be produced (See nucleic acid after step G in FIG. 12).

DNA fragments without an adaptor region in the middle are also produced. See. FIG. 12. However, since the adaptor region is biotinylated, DNA comprising adaptor regions may be selectively purified using a solid or semi-solid support with an affinity for biotin such as, for example, streptavidin beads, avidin beads, BCCP beads and the like.

Step 4H

The product of method 4 may be sequenced using any manual or automatic method available. Such methods are described in detail in Step 3H above.

Paired-Read PET Random Fragmentation, as described above and outlined in FIG. 12 offers a number of advantages. First, method 4 allows a higher confidence in assembly because mechanical shearing can result in longer fragments which, in turn, allows longer reads. Longer reads allow assembly of a target sequence with higher confidence. Second, longer fragments made possible by mechanical shearing results in paired end reads that span a longer region of nucleic acid. By spanning a longer region of nucleic acid, method 4 facilitates gap closures and also has a higher possibly of spanning regions of nucleic acid which are difficult to analyze. These difficult regions may be, for example, repeat regions or regions of high GC content. In this way, method 4 provides the advantages of improved gap closure performance. Third, method 4, because of its ability to provide gap closure, may be used exclusively to sequence complete genomes as each individual end can be use to build assemblies.

An example of the advantages of method 4 may be seen in FIG. 13. FIG. 13 depicts *E. Coli* K12 genomic DNA sequenced using Method 4. As can be seen, significantly longer read length distributions, from less than 50 to about 400, are possible using this method. Further, fragment lengths of about 3 kb can be produced and their ends sequenced. This shows that method 4 provides superior gap closure performance compared to the other methods.

Fifth Method

Paired end sequencing may be performed using a variation of the above described methods as outlined in FIG. 15.

In this method, the adaptor can be designed as a Deoxyinosine Hairpin Adaptor which incorporates deoxyinosine nucleotides (herein also referred to as Inosines) on opposite strands of the double-stranded region of the hairpin. *E. coli* Endonuclease V (EndoV) introduces a single-stranded cut (nick) between the $2^{nd}$ and $3^{rd}$ nucleotide 3' from an inosine nucleotide. (Yao M and Kow Y W, J Biol Chem. 1995, 270 (48):28609-16; Yao M and Kow Y W, J Biol Chem. 1994, 269(50):31390-6; Yao M et al., Ann N Y Acad Sci. 1994, 726:315-6; Yao M et al., J Biol Chem. 1994, 269(23):16260-8).

As illustrated in FIG. 14, the relative placement of the Inosines in the hairpin adaptor determines whether a 3' single stranded overhang (FIG. 14 A and FIG. 14 B), a 5'single stranded overhang (FIG. 14 C and FIG. 14 D), or a blunt end (no overhang) (FIG. 14 E), will be generated upon EndoV cleavage of both strands. The sequence of the hairpin adaptor can also be designed to produce a non-palindromic (FIGS. 14 A and B) or palindromic (FIGS. 14 A and C) single stranded overhang upon EndoV cleavage. It is well known in the art that deoxyinosine will pair with any of the four bases, A, G, C and T, as well as with itself (Watkins and SantaLucia, 2005, Nucleic Acids Res. 33(19):6258-67). Furthermore, the adaptor may contain a Type IIS restriction endonuclease recognition site (such as MmeI) as discussed elsewhere in this disclosure.

Step 5A (FIG. 15 Step A)

In this method, step A may be performed substantially as described for Step 1A. The target DNA can be fragmented by any of the physical or biochemical methods known in the art, as described above. Optionally, the resulting fragments may be size-fractionated by any of the size-fractionation methods described elsewhere in this disclosure.

Steps 5B and 5C (FIG. 15 Steps B+C)

The ends of the target DNA may be polished by any of the polishing methods described herein, and can be ligated to Deoxyinosine Hairpin Adaptors described above to form adaptor tagged target DNA.

Step 5D (FIG. 15 Step D)

The ligation reaction may be treated with one or more exonucleases (as discussed elsewhere herein) and size fractionated by any of the methods described herein to enrich the desired reaction products.

Step 5E (FIG. 15 Step E)

The adaptor tagged target nucleic acids are cleaved with EndoV. Conditions for the cleavage reaction may be any of the conditions described by Yao et al (Yao M and Kow Y W, J Biol Chem. 1995, 270(48):28609-16; Yao M and Kow Y W, J Biol Chem. 1994, 269(50):31390-6; Yao M et al., Ann N Y Acad Sci. 1994, 726:315-6; and Yao M et al., J Biol Chem. 1994, 269(23):16260-8). The skilled artisan will appreciate that similar conditions can also be used.

Step 5F-H (FIG. 15 Step F-H)

In this fifth method, steps F to H may be performed as described in the second, third, or fourth method (i.e. as steps 2F to H or steps 3F to H or steps 4F to H).

The Deoxyinosine Hairpin Adaptors of the fifth method are advantageous because EndoV will only cleave in the presence of Inosine or certain sites of damage or base mispairing in DNA. Therefore, the target nucleic acid will not be cleaved by the EndoV treatment. Thus, as the EndoV sites are unique to the adaptors, the target DNA need not be protected by methylation as in some above described embodiments. The elimination of the methylation step saves time, and problems related to incomplete methylation of the target DNA are eliminated. Furthermore, the EndoV digestion is very rapid as compared to the EcoRI digestion, therefore shortening the time required to perform the method.

An example of paired read results obtained by the deoxyinosine hairpin adaptor approach is shown in FIG. 16. *E. coli* K12 genomic DNA was prepared and sequenced according to the fifth method (FIG. 15). The average distance between the paired reads was 2070 bp (standard deviation=594).

Sixth Method

In an additional embodiment, paired-end sequencing may be performed by methods comprising some or all of the following steps, as depicted in FIGS. 17 and 18.

Step 6A—Fragmentation of Target DNA (FIG. 17 A)

According to the sixth method, the polynucleotide molecules of the target DNA sample, such as genomic DNA, are fragmented into molecules longer than about 500 bases, longer than about 1000 bases, longer than about 2000 bases, longer than about 5000 bases, longer than about 10000 bases, longer than about 20,000 bases, longer than about 50,000 bases, longer than about 100,000 bases, longer than about 250,000 bases, longer than about 1 million bases, or longer than about 5 million bases. In preferred embodiments, the fragments range from about 1.5 to about 5 kb in length. The fragmentation can be accomplished by any of the physical and/or biochemical methods described elsewhere in this disclosure. In a preferred embodiment, the target DNA is randomly sheared by physical force, for example by use of a HydroShear® apparatus (Genomic Solutions). The sheared DNA may then be purified with regard to the desired fragment size. This optional size selection may be achieved through any of the size selection methods known in the art and disclosed herein, such as electrophoresis and/or liquid chromatography. In a preferred embodiment, the sheared DNA sample is selected for size by purification on SPRI® size exclusion beads (Agencourt; Hawkins, et. al., Nucleic Acids Res. 1995 (23): 4742-4743). For example, sequencing the ends (in pairs) of fragments of about 2-2.5 kb can allow for contig ordering in a typical bacterial genome sequencing experiment. Larger fragments may be advantageous for sequencing of the genomes of higher organisms, such as fungi, plants and animals.

Step 6B—Methylation of Certain Restriction Sites (FIG. 17 B)

As described below, after the ligation of adaptors to the target DNA fragments, the adaptors may be cut with one or more restriction enzymes in preparation for circularization. To prevent digestion of the target DNA with the chosen restriction enzyme(s), the target DNA is protected from digestion by modification with the corresponding methylase(s). In a preferred embodiment, the adaptors are hairpin adaptors, and carry an EcoRI restriction site (FIG. 18 A). Accordingly, in a preferred embodiment, the EcoRI restriction sites present in the sample DNA fragments are methylated using EcoRI Methylase to preserve their integrity when the EcoRI cohesive ends are generated out of the Hairpin Adaptors, before circularization by ligation.

Step 6C—Fragment End Polishing and Phosphorylation (FIG. 17 C)

Hydrodynamic shearing of DNA yields some fragments with frayed ends (single stranded overhangs). Blunt ends are preferable for the subsequent adaptor ligation. Thus, optionally, any frayed ends may be made blunt and ready for ligation by enzymatically either "filling-in" with a DNA polymerase and/or by "chewing-back" with an exonuclease (e.g. Mung Bean nuclease). Advantageously, some DNA polymerases also have an exonuclease activity. Optionally, subsequent to the blunting reaction, preferably the 5' ends of the fragments will be phosphorylated with a polynucleotide kinase. In a preferred embodiment, T4 DNA polymerase and T4 polynucleotide kinase (T4 PNK) is used for filling-in and phosphorylation, respectively. The T4 DNA polymerase is used to "fill-in" 3'-recessed ends (5'-overhangs) of DNA via its 5'→3' polymerase activity, while its single-stranded 3'→5' exonuclease activity removes 3'-overhang ends. The kinase activity of T4 PNK adds phosphate groups to 5'-hydroxyl termini.

Step 6 D—Hairpin Adaptor Ligation (FIG. 17 D and FIG. 18A)

According to the invention, double-stranded oligonucleotide adaptors are ligated to the ends of the target DNA fragments. In a preferred embodiment, the adaptors are hairpin adaptors (FIG. 18 A). One advantage of hairpin adaptors is that adaptor-adaptor ligation events will only lead to adaptor dimers, i.e. the formation of multimer adaptor concatemers is prevented. In addition, their hairpin structure will protect the sample fragments from the exonuclease digestion (Step 6 E) used to remove unligated fragments. One preferred hairpin adaptor design shown in FIG. 18 A contains EcoRI and MmeI restriction sites. The EcoRI may be used to create cohesive termini on the ends of each fragment (Step 6 F), allowing for their circularization (Step 6 G), MmeI is a Type IIs restriction enzyme which cuts DNA 20 bp away from its recognition site; it is used to cut into the ends of the circularized sample fragments, generating the Paired End tags to be sequenced. The skilled artisan will recognize that EcoRI may be replaced by any of a large number of other endonucleases, with concomitant changes in the nucleotide sequence of the adaptor oligonucleotide and use of the appropriate methylase for protection of the target DNA fragments. Likewise, MmeI may be replaced with other Type IIs restriction enzymes, as long as the chosen enzyme cuts at a sufficient distance from its restriction site to generate paired ends of sufficient length to allow downstream sequence assembly. In a preferred embodiment, the hairpin adaptors are biotinylated, for example at the site shown in FIG. 18A. Other biotinylation sites are also suitable and can be chosen by the skilled artisan. The biotin moiety allows for the optional selection of adaptor-containing paired end fragments, and an optional immobilization of the paired end library fragments (after MmeI digestion) during the ligation of the paired end adaptors, during the fill-in reaction (fragment repair), and during the paired end library amplification.

Step 6 E—Exonuclease Selection (FIG. 17 E)

Preferably, an exonuclease digestion follows the ligation of the Hairpin Adaptors, to remove any DNA that is not properly fitted with Hairpin Adaptors at both ends; and purification on SPRI size exclusion beads removes small unwanted molecular species, such as adaptor-adaptor dimers. The exonuclease digestion may be performed with one or more of various exonucleases well known in the art. Preferably, the digestion is accomplished with a combination of activities that together allow digestion of single stranded and double stranded DNA, both in the 3'→5' and 5'→3' directions. In a preferred embodiment, the exonuclease mixture contains E. coli Exonuclease I (3'→5' single strand exonuclease), Phage Lambda Exonuclease (5'→3' single and double strand exonuclease) and Phage T7 Exonuclease (5'→3' double strand exonuclease, can initiate at gaps and nicks).

Step 6 F—EcoRI Digestion (FIG. 17 F)

In a preferred embodiment, endonucleolytic cleavage by EcoRI is used to create cohesive termini on the ends of each fragment by cutting the hairpin adaptors (FIG. 18 A) and allowing for the fragments' circularization. Digestion with EcoRI will remove the hairpin structures at the ends of the fragments, leaving cohesive ends. The internal EcoRI sites present in the sample DNA are protected by the methylation done earlier in Step 6B.

Step 6 G—Circularization (FIG. 17 G)

The fragments are then circularized by intramolecular ligation of their cohesive EcoRI ends. The site of the ligation thus has the two partial Hairpin Adaptors (head to head, with a reconstituted EcoRI site; 44 bp total), flanked on either side by the ends of the sample fragment. Another exonuclease digestion is carried out to remove any non-circularized DNA.

Step 6 H—MmeI digestion (FIG. 17 H)

The circularized DNA fragments are then restricted with MmeI. This Type IIs restriction enzyme cuts approximately 20 bp away from its restriction site (leaving a 2 nt 3'-overhang, i.e. the cut is at 20/18 nt; the enzyme also generates some minority products with cuts ranging from 19 to 22 bp from the site). There are MmeI sites at the end of the Hairpin Adaptors (FIG. 18 A) that are ligated to the sample DNA fragments; restriction at these sites generates the Paired End DNA library fragments, each containing the ligated "double" Hairpin Adaptors (44 bp) and the two 20 bp ends of the sample fragment, for a total length of 84 bp.

Step 6 I—Isolation with Streptavidin Beads (FIG. 17 I)

Lacking a biotin tag, MmeI restriction fragments without the ligated "double" hairpin adaptor may optionally be eliminated in this step. The library of paired end fragments may be immobilized (and isolated from other MmeI restriction fragments) by binding of the biotin tag present in the hairpin adaptors to streptavidin or avidin beads.

Step 6 J—Paired End Adaptor Ligation (FIG. 17 J)

In this step, the ends of the paired end library fragments generated in Step 6 H and optionally purified in Step 6 I are ligated to double stranded adaptors, termed paired end library adaptors or paired end adaptors (FIG. 18 B). These paired end adaptors provide priming regions to support both amplification and nucleotide sequencing, and may also comprise a short (e.g. 4 nucleotides) "sequencing key" sequence useful for well finding on a 454 Sequencing™ System. The adaptors may have "degenerate" 2-base single stranded 3' overhangs. Degenerate means that the 2 overhanging bases are random, i.e. they may each be either G, A, T, or C. If an enzyme other than MmeI were used, the skilled artisan would be readily able to design paired end adaptors compatible with that other enzyme. The exemplary adaptors shown in FIG. 18 B are designed to strongly favor the directional ligation to the paired end library fragments with each Adaptor containing a degenerate 2 bp 3'-overhang at their 3' end which can solely ligate to the ends of the MmeI-generated paired end library fragments (provided the 5' ends of the adaptors are not phosphorylated, see below). Adaptors may be combined with the paired end library fragments in a ligation reaction that contains a large molar excess of adaptors (15:1 adaptor:fragment ratio), both to maximize utilization of the paired end library fragments and to minimize the potential of forming paired end library fragment concatemers. The adaptors themselves may be non-phosphorylated to minimize the formation of adaptor dimers, though as a consequence, the ligation products must be subsequently repaired by a fill-in reaction (Step 6 K)

Step 6 K—Fill-In Reaction (FIG. 6 K)

If the paired end adaptors ligated in Step 6 J are not phosphorylated, gaps will be present at their 3'-junctions with the paired end library DNA fragments. These two "gaps" or "nicks" may be repaired using a strand-displacing DNA polymerase, whereby the polymerase recognizes the nicks, displaces the nicked strands (to the free 3'-end of each Adaptor), and extends the strand in a manner that results in the repair of the nicks and in the formation of full-length dsDNA. In a preferred embodiment, Bst DNA polymerase (Large Fragment) is used. Other strand-displacing DNA polymerases known in the art are also suitable for this step, such as phi29 DNA Polymerase, DNA Polymerase I (Klenow Fragment), or Vent® DNA Polymerase.

Step 6 L—Amplification (FIG. 6 L)

Optionally, the "adapted" paired end DNA library may be amplified. Preferably, the amplification is performed by PCR, but other nucleic acid amplification methods known in the art and/or described herein may also be used. Preferably, the oligonucleotides F-PCR and R-PCR shown in FIG. 18B may be used as PCR primers.

The "adapted" paired end DNA library, whether amplified (as described in the above paragraph) or not, is then sequenced. Preferably, individual molecules from the library are sequenced. If the chosen DNA sequencing method requires a plurality of identical template molecules in each individual sequencing reaction, individual molecules from the library may be clonally amplified. Preferably, the clonal amplification is performed by bead emulsion PCR as described in International Patent Application Nos. WO 2005/003375, WO 2004/069849, WO 2005/073410, each incorporated herein by reference in toto.

It is to be understood that any combination of corresponding steps of the six methods described above are also contemplated and are included in the invention.

As can be seen from the disclosures above, there are similarities between methods 1, 2, 3, 4, 5 and 6. In particular, the analogous steps of methods 2, 3, 4, 5 and 6 are especially similar and may be combined and interchanged between the methods to produce equivalent or favorable results.

Now that the general methods of paired-end sequencing have been described, variations of the methods are described.

In one variation, the hairpin adaptors may be replaced with overhang adaptors (FIG. 8). The overhang adaptor may be biotinylated and may, for example, have the sequence of:

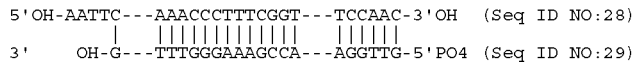

```
5'OH-AATTC---AAACCCTTTCGGT---TCCAAC-3'OH   (Seq ID NO:28)
     |    ||||||||||||    ||||||
3'    OH-G---TTTGGGAAAGCCA---AGGTTG-5'PO4  (Seq ID NO:29)
```

The six 3' terminal nucleotides of the upper strand (Seq ID NO:28), i.e., TCCAAC, in conjunction with the complementary nucleotides of the lower strand (Seq ID NO:29), form a recognition site for the Type II S restriction enzyme MmeI.

The variation is performed in a fashion similar to method 3. First genomic DNA (FIG. 8A) is fragmented and polished (FIG. 8B) and overhang adaptors are ligated to the ends of the fragments (FIG. 8C). Dimers of overhang adaptors may be removed by size fractionation chromatography (i.e., spin column) or charge based chromatography. Higher concatemers of the overhang adaptors cannot be formed because of the lack of a phosphate in the 5' overhang. After removal of the overhang primer dimers (FIG. 8D), the fragments are enabled for self ligation by treatment with kinase (FIG. 8E). Self ligation (i.e., circularization) is performed and an exonuclease digest may subsequently be performed to remove unligated non-circular DNAs. Since DNA fragments not ligated to overhang adaptors have blunt ends due to polishing, they are not expected to ligate as efficiently as the 5' overhang ends (sticky ends) of the fragments with two overhang adaptors ligated one on each side. Following circularization, Mme I digest is used to remove DNA distal to the overhang adaptors (see FIG. 8F) leaving about 20 bases of the original genomic DNA on each side of the ligated overhang adaptors (FIG. 8G). The fragment with overhang adaptors are purified using a streptavidin bead which binds to the biotinylated adaptors (FIG. 8 H).

The resulting fragment may be sequenced by any method available such as, for example, the methods provided in this disclosure (e.g., step 3H).

The nucleic acids generated by the methods of the invention may be sequenced using one or more primers complementary to the end(s) of the sequence. That is, under the sequencing protocol described in Step 3H, a sequencing adaptor A and sequencing adaptor B is ligated to the ends of fragments before they are sequenced. Since the end sequence of the fragment is know to be either sequencing adaptor A or B, a sequencing primer complementary to sequencing adaptor A or B may be used to sequence the fragment. Furthermore, a sequence in the middle of each fragment, comprising ligated adaptors, is known (see, e.g., 703 in FIG. 7). Sequencing may also start from the middle using a primer complementary to this middle region. Furthermore, a sequencing primer from the end region and a sequencing primer from the middle region may be hybridized to a fragment to be sequenced concurrently (see FIG. 9). One primer is protected while the other primer is not. In FIG. 9, the primer hybridized to the end is protected by a phosphate group. The first round of sequencing will commence from the non-protected primer (FIG. 9, middle primer). After the first round of sequencing, the elongation of the first primer may optionally be terminated, for example by incorporation of a complementary dideoxynucleotide. Alternatively, elongation of the first primer may have proceeded to the end of the template strand, making termination unnecessary. The second protected primer may be deprotected and elongated in a second round of sequencing to determine the sequence from the end of the fragment. This method enables two long paired-end sequencing reads from a single template which can be single stranded.

In a second variation, the fragmented starting DNA (FIG. 10A) is ligated to adaptors with 3' CC overhangs and an optional internal Type IIS restriction endonuclease site. The ligated fragments cannot self ligate or self circularize because their ends are not compatible (not complementary). However, these fragments may be ligated using a linker with 5' GG overhangs on both sides (FIG. 10 B). After ligation, the nucleic acid fragments may be purified from non-circular DNA by standard gel and column chromatography discussed above or by exonuclease digestion which cleaves uncircularized molecules. The resulting circular DNA (FIG. 10 D) may be cleaved with MmeI as in the other methods and the resulting DNA may be sequenced.

In another variation, the methods of the invention may be used to produce A/B adapted ssDNA (FIG. 11, step 1). This single stranded fragment may be circularized by hybridization to an oligo comprising sequences complementary to the A/B adaptors (FIG. 11, step 2) and ligated in the presence of ligase. In addition to facilitating ligation, the oligo may be used as a primer to facilitate rolling circle amplification of the circularized ssDNA (FIG. 11, step 3). The rolling-circle amplified DNA may be cleaved as described for Method 1, Steps 1 K and L (FIGS. 1 L and M), Following amplification, standard library preparation and sequencing techniques may be applied to the product (FIG. 11, step 4).

Some embodiments of the present invention are based upon the surprising discovery that in a paired end sequencing experiment of the *E. coli* strain K12 genome, wherein the experimental protocol comprised the use of MmeI cleavage according to the methods described herein, the depth of read coverage across the genome varied greatly (FIG. 20, "no carrier(−)"). By depth is meant the number of sequence reads mapping to substantially the same region of the genome. This depth variation was correlated to the density of MmeI sites across the genome (FIG. 20). Unexpectedly and surprisingly, the inventors discovered that the addition of double stranded DNA known to contain MmeI sites (designated "(+)" in FIG. 20), i.e. *E. Coli* B Strain DNA ("EcoliBStrain(+)"), Salmon Sperm DNA ("SalSprmDNA(+)"), or a PCR amplification product known to contain MmeI sites ("AmpPosMmeI(+)") greatly decreased and randomized the variation of depth of coverage across the genome. However, addition of double stranded DNA lacking MmeI sites (designated "(−)" in FIG. 20), i.e. poly(dIdC) ("dIdC(−)"), or a PCR amplification product known to contain no MmeI sites ("AmpNeg MmeI(−)") did not change the pattern of variation of depth of coverage across the genome, as compared to the "no carrier" control. Therefore, the use of MmeI-positive carrier DNA provided a more even distribution of paired end reads across the genome, which is advantageous. These surprising findings are further substantiated by the data shown in the following Tables:

TABLE 1

Effect of MmeI carrier DNA on Depth Distribution and Length of Paired-End Reads

| Sample | Depth Ave | Depth STDEV | Depth % CV | Length Ave | LengthSTDEV | Length % CV |
|---|---|---|---|---|---|---|
| Stratagene_SS_dsDNA | 25.59 | 9.27 | 36.2% | 2,219 | 618 | 27.8% |
| EcoliBStrain | 21.99 | 8.32 | 37.8% | 2,210 | 618 | 28.0% |
| AmpPos | 22.82 | 7.51 | 32.9% | 2,199 | 618 | 28.1% |
| dIdC | 22.17 | 26.55 | 119.7% | 2,397 | 651 | 27.2% |
| AmpNeg | 21.10 | 22.93 | 108.7% | 2,363 | 639 | 27.0% |
| Negative | 23.05 | 26.01 | 112.8% | 2,385 | 654 | 27.4% |

Table 1 shows depth of coverage statistics for *E. Coli* K12. The top three samples (rows) had MmeI-positive carrier DNA added, while the bottom three samples had MmeI-negative carrier DNA added. Column headers represent: "Depth Ave"=average depth; "Depth STDEV"=standard deviation of depth; "Depth %CV"=Depth STDEV divided by Depth Ave (this quotient expresses the variation in depth corrected by the average depth); "Length Ave"=average distance of the paired reads in the genome; "LengthSTDEV"=standard deviation of the distance of the paired reads in the genome; "Length%CV"=LengthSTDEV divided by Length Ave.

Table 1 shows, in accordance with FIG. 20, that the variation in depth of coverage across the *E. coli* K12 genome was greatly lowered by the addition of MmeI-positive carrier DNA (see Depth STDEV and Depth %CV values; smaller Depth STDEV and Depth %CV values are advantageous). This lead to a more uniform distribution of paired end reads across the genome. This uniform distribution is advantageous.

TABLE 2

Effect of paired end sequencing with MmeI-positive carrier DNA on the genome scaffolding of *E. Coli* K12

| | Stratagene SS dsDNA (+) | E. Coli Bstrain (+) | Amplified Positive (+) | dIdC (−) | Amplified Negative (−) | NoCarrier (−) |
|---|---|---|---|---|---|---|
| Number of scaffolds | 25 | 22 | 19 | 56 | 53 | 48 |
| Number of bases scaffolded | 4,565,936 | 4,569,196 | 4,571,112 | 4,553,955 | 4,548,402 | 4,550,228 |
| Percent of genome scaffolded | 98.41% | 98.48% | 98.52% | 98.15% | 98.03% | 98.07% |

Table 2 shows the effect of paired end sequencing data obtained with MmeI-positive carrier DNA on the scaffolding of shotgun contigs. When 121 large contigs obtained by shotgun sequencing of *E. Coli* K12 genomic DNA on a GS20 sequencing apparatus (454 Life Sciences, Branford, Conn., USA) were assembled with paired end sequencing reads, a lower number (19-25) of scaffolds (i.e., larger scaffolds) resulted from paired end sequencing reads produced with MmeI-positive carrier DNA (columns "Stratagene SS dsDNA (+)", "*E. Coli* Bstrain (+)" and "Amplified Positive (+)"), compared to paired end sequencing reads produced without carrier DNA, or carrier DNA lacking MmeI sites (48-56 scaffolds). Therefore, the use of MmeI positive carrier DNA improves the genome assembly performance achieved by paired end sequencing performed according to the present invention.

In some embodiments, the methods of the invention include the use of double-stranded "carrier DNA" in any step that comprises DNA cleavage by the restriction endonuclease MmeI. The carrier DNA must contain MmeI sites. Endonucleolytic cleavage by MmeI occurs most efficiently when the number of moles of MmeI enzyme molecules about equals the number of moles of MmeI sites present in the DNA sample (Product Catalog of New England Biolabs, Ipswich, Mass., USA). In the methods of the present invention, the number of MmeI sites can be difficult to estimate due to low DNA concentrations (typically in the order of nanograms to tens of nanograms) which are difficult and time consuming to measure reliably, and also due to variations in the number of MmeI sites based on the target DNA to be sequenced. Thus, an accurate computation of the amount of MmeI enzyme to be added to a reaction (to achieve stoichiometric concentrations) is problematic. In order to overcome this difficulty and to satisfy the need to balance the number of MmeI sites with the number of MmeI enzyme molecules, some methods of the invention include the addition of an excess of carrier DNA (in relation to sample DNA). In this way, the amount of MmeI enzyme to be added to the reaction can be calculated based upon a known amount of carrier DNA, while the number of MmeI sites in the (circular) sample DNA becomes negligible. A measurement of the DNA concentration of the sample DNA therefore becomes unnecessary. This improves the speed and reduces cost and time required by the methods. The amount of carrier DNA may outweigh the amount of sample DNA by several fold to about tenfold, to about 100-fold, to about 1000-fold, or more. In a preferred embodiment, two micrograms of sonicated double stranded salmon sperm DNA is added to the sample DNA with 2 units of MmeI and all required reagents (e.g. 1×NEBuffer 4 (New England Biolabs) and 50 µM S-adenosylmethionine (SAM)) in a volume of 100 microliters, and incubated at about 37 degrees Celsius for about 15 minutes. The skilled artisan will recognize that reaction temperature and duration may be adjusted within practical ranges.

The use of excess MmeI-site containing carrier DNA in an MmeI restriction digestion, in conjunction with approximately stoichiometric amounts of MmeI enzyme, as described above, may optionally be incorporated in any of the methods comprising MmeI digestion described in the present disclosure, for example in Step 6 H of the sixth method (FIG. 17 H). The skilled artisan will also recognize that the strategy of adding "carrier DNA" containing MmeI sites is useful in any MmeI restriction digestion reaction, particularly reactions where the sample DNA amount is low and/or the number of MmeI sites in the sample DNA is unknown.

Ligation in Water-In-Oil Emulsion

The present invention also includes methods for circularization of nucleic acid molecules. Commonly, circularization of nucleic acid molecules is achieved by ligation at low nucleic concentrations. Low concentrations favor the desired intramolecular ligation reaction (i.e. circularization) which follow first-order reaction kinetics, over intermolecular events which follow second-order (or higher-order) reaction kinetics (F. M. Ausubel, et al., (eds), 2001, *Current Protocols in Molecular Biology*, John Wiley & Sons Inc.). However, even at high dilution, intermolecular events can not be prevented, and extreme dilutions of the nucleic acid is not practical. The occurrence of intermolecular ligation (concatemers, double-circles etc.) reduces the yield of the desired intramolecular circularization events. In some scenarios, intermolecular ligation products can be detrimental to downstream applications. In summary, the conventional approach has at least two major drawbacks. Firstly, the need to dilute the starting nucleic acid increases the reaction volume and associated reagent costs. The high dilution also makes efficient recovery of the reaction products difficult. Secondly, large numbers of intermolecular ligation events do occur, reducing the yield of the desired intramolecular ligation products.

The invention includes methods which largely eliminate the issues associated with the conventional circularization approaches described above. For example, according to the present invention, there is no need to perform the ligation reaction at high dilution, i.e. at low nucleic acid concentrations. In one embodiment, individual linear double-stranded DNA molecules having compatible ligatable ends, such as blunt ends or staggered ("sticky") ends, are ligated in physically isolated reaction environments. An aqueous solution containing the DNA to be ligated and all reagents necessary for the ligation reaction (for example, DNA ligase, ligase buffer, ATP, etc.), is emulsified in oil, preferably in the presence of a surfactant that serves to stabilize the emulsion. Suitable compositions and methods for creating emulsions are discussed in more detail below. The resulting water-in-oil emulsion contains microdroplets (microreactors), each containing zero, one, or more DNA molecules. The number of DNA molecules per microreactor can be adjusted by modifying the DNA concentration and the size of the microdroplets. For a skilled artisan, it is a matter of routine optimization to calculate appropriate conditions based on nucleic acid concentration, the size of the polynucleotides (length measured as the number of bases), and the average volume of the microdroplets. An ideal microdroplet will contain a single ligatable DNA molecule. However, it is understood that in a population of microreactors, the number of DNA molecules per microreactor will vary depending, in part, on size variability of the microreactors and random distribution of the DNA molecules. Thus, some microreactors may contain no DNA molecule, some may contain one DNA molecule, and some may contain two or more DNA molecules. One skilled in the art will recognize that yield and cost (reagent use) can be balanced as needed by varying the average number of DNA molecules per microreactor.

Preferably, the ligation mixture will be kept cold (for example, at 0-4 degrees Celsius) while it is being assembled and until the emulsification process is complete. This will prevent the ligation reaction from proceeding before the desired emulsion environment is formed, and will therefore prevent the formation of unwanted intermolecular bonds. Subsequently, the emulsified ligation reaction will be incubated at temperatures that are permissive of the ligation reaction. The incubation time may range from several minutes to an hour, to several hours, to overnight, or to 24 hours or more than a day. After this incubation, but prior to, during, and after the breaking of the emulsion, the ligation reaction may be halted to prevent undesirable intermolecular ligations in the combined ligation reactions. The ligation reaction may be halted by lowering the temperature to about 0-4 degrees Celsius (water ice), by heat inactivation of the ligase, by addition of EDTA, addition of a ligase inhibitor, etc. or any combination of such methods.

The skilled artisan will readily apply the above described methods of the invention to the circularization of single stranded or double stranded RNA, or single stranded or double stranded DNA. For example, the ends of a linear single stranded polynucleotide molecule can be brought in direct juxtaposition by annealing to a capping oligonucleotide (also termed a bridging oligonucleotide) that has portion complementary to each end of said linear single stranded polynucleotide molecule, as described in Step 1K of Method 1 (see FIG. 1L and FIG. 1I).

The emulsified ligation reaction may then be incubated at a suitable temperature. For example, for a "sticky-end" ligation with T4 DNA ligase, a suitable incubation temperature is 16 degrees Celsius, but a broad range of temperatures is acceptable. Conditions for ligation of DNA and other molecules are widely known in the art. One advantage of performing the circularization reaction in emulsion is that extended reaction times are neutral to, or even beneficial to the success of the procedure. For example, in an ideal scenario with no more than one DNA molecule per microreactor, the incubation time can be extended until most DNA molecules have been circularized. In contrast, by using the conventional non-emulsion methods described above, prolonged incubation may lead to a higher proportion of intermolecular ligation products. Another advantage of the emulsion based ligation methods of the invention is the ability to allow the reaction to proceed for relatively long periods of time without increasing the occurrence of intermolecular ligation. Such increased incubation times allow for a greater number of circularized products without the increased risk of inter molecular ligations to occur. Furthermore, since the molecules are being isolated by physical means and not in a concentration dependent manner, the reaction volumes may be much lower (i.e. the nucleic acid concentration of nucleic acid in the aqueous phase may be much higher) for the same number of ligation events, lowering the cost for the reagents and increasing the ease of processing the samples. The skilled artisan will understand that for ligation to occur in a given microdroplet, said microdroplet must contain sufficient reagents, including at least one molecule of ligase enzyme.

Breaking the Emulsion and Isolation of Circularized DNA

Following ligation, the ligation reaction may be halted, and the emulsion is "broken" (also referred to as "demulsification" in the art). There are many methods of breaking an emulsion (see, e.g., U.S. Pat. No. 5,989,892 and references cited therein) and one of skill in the art would be able to select an appropriate method. Demulsification may be followed by a nucleic acid isolation step that may be done by any suitable method for isolating nucleic acid. Once the nucleic acid is isolated, the unligated material may be removed by any method suitable for this task, one of which is to perform an exonuclease digestion of the sample. The particular exonuclease enzyme used will depend, in part, on the type of molecules being worked on (single stranded or double stranded, DNA or RNA), and other considerations, for example reaction temperatures conveniently incorporated into the process. The circularized material will have to be purified after the exonuclease treatment by one of the many procedures known in the art, such as phenol/chloroform extraction or any commercially available purification kit suitable for this purpose.

Using the conventional dilution-based circularization protocols described above, it has been observed that the recovery of desired circular products decreases with increasing length of the linear input DNA molecules. The emulsion ligation methods of the invention are particularly useful in the circularization of long polynucleotide molecules, such as molecules longer than about 500 bases, longer than about 1000 bases, longer than about 2000 bases, longer than about 5000 bases, longer than about 10000 bases, longer than about 20,000 bases, longer than about 50,000 bases, longer than about 100,000 bases, longer than about 250,000 bases, longer than about 1 million bases, or longer than about 5 million bases, or in fact any size deemed desirable in an experimental protocol of interest.

The emulsion ligation methods described herein are useful in a wide variety of ligation reactions, whether they result in circularization or not. Thus, the emulsion ligation methods described above may be used in any ligation step of the various methods described herein, especially ligation reactions where circularization of the input nucleic acids is desired.

Emulsification

Emulsions are heterogeneous systems of two immiscible liquid phases with one of the phases dispersed in the other as droplets of microscopic or colloidal size. Emulsions of the invention must enable the formation of microcapsules (microreactors). Emulsions may be produced from any suitable combination of immiscible liquids. The emulsion of the present invention has a hydrophilic phase (containing the biochemical components) as the phase present in the form of finely divided droplets (the disperse, internal or discontinuous phase) and a hydrophobic, immiscible liquid (an "oil") as the matrix in which these droplets are suspended (the nondisperse, continuous or external phase). Such emulsions are termed "water-in-oil" (W/O). This has the advantage that the entire aqueous phase containing the biochemical components is compartmentalised in discrete droplets (the internal phase). The external phase, being a hydrophobic oil, generally contains none of the biochemical components and hence is inert.

In some embodiments, microreactors contain reagents necessary for nucleic acid ligation. A plurality of microreactors may contain exactly one polynucleotide molecule each. In certain embodiments, a thermostable water-in-oil emulsion will be desirable, for example if heat inactivation of the ligase will be performed after the reaction, or if ligation is performed at elevated temperatures using a thermostable ligase (e.g. Taq DNA Ligase). The emulsion may be formed according to any suitable method known in the art. One method of creating emulsion is described below but any method for making an emulsion may be used. These methods are known in the art and include adjuvant methods, counter-flow methods, cross-current methods, shaking, rotating drum methods, and membrane methods. Furthermore, the size of the microcapsules may be adjusted by varying the flow rate and speed of the components. For example, in dropwise addition, the size of the drops and the total time of delivery may be varied. In some embodiments, the microdroplets may be created within a microfluidic device, for example as described by Link et al. (Angew. Chem. Int. Ed., 2006, 45, 2556-2560), hereby incorporated by reference in toto.

At least some of the microreactors should be sufficiently large to encompass sufficient nucleic acid and other ligation reagents. However, at least some of the microreactors should be sufficiently small so that a portion of the microreactor population contains a single self-ligatable polynucleotide molecule. In some embodiments, the emulsion is heat stable. Preferably, the droplets formed range in size from about 100 nanometers to about 500 micrometers in diameter, more preferably from about 1 micrometer to about 100 micronmeters. Advantageously, cross-flow fluid mixing, optionally in combination with an electric field, allows for control of the droplet formation, and uniformity of droplet size.

Various emulsions that are suitable for biologic reactions are referred to in Griffiths and Tawfik, EMBO, 22, pp. 24-35 (2003); Ghadessy et al., Proc. Natl. Acad. Sci. USA 98, pp. 4552-4557 (2001); U.S. Pat. No. 6,489,103 and WO 02/22869, each fully incorporated herein by reference. In a preferred embodiment, the oil is a silicone oil.

Surfactants

Emulsions of the invention may be stabilised by addition of one or more surface-active agents (emulsion stabilizers; surfactants). These surfactants are also termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash, M. and Ash, I. (1993) *Handbook of industrial surfactants*. Gower, Aldershot). Emulsion stabilizers used in the methods of the present invention include Atlox 4912, sorbitan monooleate (Span80; ICI), polyoxyethylenesorbitan monooleate (Tween80; ICI) and other recognized and commercially available suitable stabilizers.

In various embodiments, the surfactant is provided at a v/v concentration in the oil phase of the emulsion of 0.5 to 50%, preferably 10 to 45%, more preferably 30-40%.

In some embodiments, chemically inert silicone-based surfactants, such as silicone copolymers, are used. In one embodiment, silicone copolymer used is polysiloxane-polycetyl-polyethylene glycol copolymer (Cetyl Dimethicone Copolyol) e.g. Abil® EM90 (Goldschmidt).

The chemically inert silicone-based surfactant may be provided as the sole surfactant in the emulsion composition or may be provided as one of several surfactants. Thus, a mixture of different surfactants may be used.

In particular embodiments, one surfactant used is Dow Corning® 749 Fluid (used at 1-50%, preferably 10 to 45%, more preferably 25-35% w/w). In other particular embodiments, one surfactant used is Dow Corning® 5225C Formulation Aid (used at 1-50%, preferably 10 to 45%, more preferably 35-45% w/w). In a preferred embodiment, the oil/surfactant mixture consists of: 40% (w/w) Dow Corning® 5225C Formulation Aid, 30% (w/w) Dow Corning® 749 Fluid, and 30% (w/w) silicone oil.

The methods of the invention provide a plurality of benefits and advantages over current methods. One advantage of the current method over the prior art is that cloning and propagation of the prepared fragments in a eukaryotic or prokaryotic host is not required. This is especially useful where the target sequence comprise multiple repeats that may rearrange during propagation as an episome in a host cell.

Another advantage of the disclosed method is that it can facilitate genome assembly by providing not only contig sequences, but the end sequences and orientation of the end sequences of long contigs which may have a length of over 100 bp, over 300 bp, over 500 bp, over 1 kb, over 5 kb, over 10 kb, over 100 kb, over 1 Mb, over 10 Mb, or larger. This sequence information and orientation information may be used to facilitate genome assembly, and provide gap closure.

Furthermore, paired end reads provides a second level of confidence in the assembly of a genome. For example, if paired end sequencing and regular contig sequencing are in agreement about a DNA sequence, then the level of confidence of that sequence is increased. Alternatively, if the two sequence data contradicts each other, then the confidence is reduced and more analysis and/or sequencing would be necessary to locate the source of inconsistency.

The presence or absence of open reading frames in paired end reads also provides directions as to the location of open reading frames. For example, if both sequenced ends of a contig contain an open reading frame, there is a chance that the complete contig is an open reading frame. This can be confirmed by standard sequencing techniques. Alternatively, with the knowledge of the two ends, specific PCR primers may be constructed to amplify the two ends and the amplified region may be sequenced to determine the presence of open reading frames.

The methods of the invention will also improve the understanding of genome organization and structure. Since paired end sequencing has the ability to span regions that are difficult to sequence because a genomic structure may be deduced even if these regions are not sequenced. The difficult to sequence regions may be, for example, repeat regions and regions of secondary structure. In this case, the number and location of these difficult regions can be mapped in a genome even if the sequences of these regions are not known.

The methods of the invention also allow the haplotyping of a genome over an extended distance. For example, specific primers may be made to amplify regions of a genome containing two SNP linked by a long distance. The two ends of this amplified region may be sequenced, using the methods of the invention, to determine the haplotypes without sequencing the nucleic acid between the two SNP. This method is especially useful where the two SNPs span a region that is uneconomical to sequence. These regions include long regions, regions with repeats, or regions of secondary structure.

The biotinylated adaptors of the methods provide additional advantages (FIG. 7). FIG. 7A shows nucleic acids ligated to sequencing primers A and B in a format ready for sequencing. Some of the nucleic acids are contaminating nucleic acids which do not contain two ends of a single contig region (701). Nucleic acid fragments containing both ends of a contig are denoted as 702. Since nucleic acid 702 is the sole species of nucleic acid that comprises biotin, this species may be purified using a streptavidin bead (FIG. 7B). This specie is ready for sequencing after purification. By using affinity purification, the fraction of sequences that yield useful information may be substantially increased.

This is especially useful when the contaminating DNA (701) is long, for example, if each of the contaminating nucleic acids (701) in FIG. 7D is several kb in length. Sequencing these contaminants would consume a considerable portion of reagents, manpower, and computer power devoted to a project. In this case, the prior purification of the proper fragment by affinity chromatography (FIG. 7E) would provide substantial labor and reagent savings.

The skilled artisan will immediately appreciate that endonucleolytic cleavage by EndoV of any double-stranded DNA containing opposite strand inosines (as depicted in FIG. 14, with or without a hairpin) can produce single stranded overhangs (sticky ends), wherein the overhangs may have virtually any nucleotide sequence. The invention also includes polynucleotide designs and methods substantially similar to FIG. 14, but without a hairpin. Furthermore, it will be readily apparent that the methods and compositions of the invention as depicted in FIG. 14, with or without hairpins, as described above, will be useful in a large number of molecular biology and recombinant DNA techniques in which the introduction of unique endonuclease sites is desirable. Such techniques include, but are not limited to, the construction of DNA and cDNA libraries, various subcloning strategies, or any methodology that benefits from unique endonuclease sites in primers, adaptors, or linkers.

The paired-end nucleic acid constructs produced by any of the methods described herein may be sequenced by any sequencing method known in the art. Standard sequencing methods such as Sanger sequencing or Maxam-Gilbert sequencing are widely known in the art. Sequencing may also be performed, for example, by using the automated sequencing method known as 454 Sequencing™ developed by 454® Life Sciences Corporation (Branford, Conn., USA) which is described, for example, in International Application No. WO/05003375 filed Jan. 28, 2004 and in U.S. patent application Ser. Nos. 10/767,779 filed Jan. 28, 2004; 60/476,602, filed Jun. 6, 2003; 60/476,504, filed Jun. 6, 2003; 60/443,471, filed Jan. 29, 2003; 60/476,313, filed Jun. 6, 2003; 60/476, 592, filed Jun. 6, 2003; 60/465,071, filed Apr. 23, 2003; and 60/497,985; filed Aug. 25, 2003. Additional sequencing methods known in the art, for example any sequencing-by-synthesis or sequencing-by-ligation method, as reviewed by Metzger (Genome Res. 2005 December; 15(12):1767-76), hereby incorporated by reference), are also contemplated and may be used in the paired end sequencing methods of the invention.

Throughout this disclosure, the term "biotin" "avidin" or "streptavidin" have been used to describe a member of a binding pair. It is understood that these terms are merely to illustrate one method for using a binding pair. Thus, the term biotin, avidin, or streptavidin may be replaced by any one member of a binding pair. A binding pair may be any two molecules that show specific binding to each other and include, at least, binding pairs such as FLAG/anti-FLAG antibody; Biotin/avidin, biotin/streptavidin, receptor/ligand, antigen/antibody, receptor/ligand, polyHIS/nickel, protein A/antibody and derivatives thereof. Other binding pairs are known and are published in the literature.

All patents, patent applications and references cited anywhere in this disclosure are hereby incorporated by reference in their entirety.

The invention will now be further described by way of the following non-limiting Examples.

EXAMPLES

Example 1

Oligonucleotide Design

Oligonucleotides used in the experiments are designed and synthesized as follows.

Capture element oligonucleotides, shown on the top part of FIG. 3A, are designed to include UA3 adaptors and keys. A NotI site is located between the adaptors. The complete construct (the capture element) may be created using nested oligos and PCR. The sequence of the final product is synthesized and cloned.

Type IIS capture fragment oligonucleotides, shown on the bottom part of FIG. 3A, are similar to the capture fragment described above except that sequences representing a type IIS restriction endonuclease site (e.g., MmeI) are included in the capture fragment after the key sequence. These type IIS restriction endonuclease cleavage sites permit the cleavage of any construct made with these capture elements to be cut with a type IIS restriction endonuclease. As known in the art, type IIS restriction endonucleases cleave DNA at various distances from the recognition site, in the case of MmeI, at 20/18 bases.

A short adaptor capture fragment oligonucleotide was designed to contain SAD1 adaptors and keys (FIG. 3B). A NotI site is also situated between the adaptors. This oligonucleotide may be synthesized with a MmeI type IIS restriction endonuclease cleavage site after the key sequence (See FIG. 3B, short adaptor capture fragment (type IIS)).

Example 2

Protocol for the Hairpin Adaptor Paired End Sequencing

*E. Coli* K12 DNA (20 μg) in 100 μl was hydrosheared on speed 10 for 20 cycles using the standard HydroShear assembly (Genomic Solutions, Ann Arbor, Mich., USA). A methylation rection was performed on the sheared DNA by adding 50 μl of DNA (5 μg), 34.75 μl of $H_2O$, 10 μl of methylase buffer, 0.25 μl of 32 mM SAM, and 5 μl of EcoRI methylase (40,000 units/ml, New England Biolabs (NEB), Ipswich, Mass., USA). The reactions were incubated for 30 minutes at 37° C. After the methylation reaction, the sheared, methylated DNA was purified using a Qiagen MinElute PCR Purification column, according to the manufacturer's instructions. The purified DNA was eluted from the column with 10 μl of EB buffer.

The sheared, methylated DNA was subjected to a polishing step to create sheared material having blunt ends. DNA at 10 μl was added to a reaction mixture containing 13 μl $H_2O$, 5 μl of 10× polishing buffer, 5 μl of 1 mg/ml bovine serum albumin, 5 μl of 10 mM ATP, 3 μl of 10 mM dNTPs, 5 μl of 10 U/μl T4 polynucleotide kinase, and 5 μl of 3 U/μl T4 DNA polymerase. The reactions were incubated for 15 minutes at 12° C., after which the temperature was raised to 25° C. for an additional 15 minutes. The reactions were subsequently purified on a Qiagen MinElute PCR purification column according to the manufacturer's instructions.

The hairpin adaptor was ligated to the sheared, blunt-end DNA fragments by adding 10 μl of 5 μg sheared DNA, 17.5 μl of $H_2O$, 50 μl of 2× Quick Ligase Buffer, 20 μl of 10 μM Hairpin Adaptor, and 2.5 μl of Quick Ligase (T4 DNA Ligase, NEB). The reactions were incubated at 25° C. for 15 minutes, after which the ligated fragments were selected by adding to the mixture 2 μl of λ exonuclease, 1 μl Rec J (30,000 units/ml, NEB), 1 μl of T7 exonuclease (10,000 units/ml , NEB), and 1 μl of exonuclease I (20,000 units/ml, NEB). The reactions were incubated at 37° C. for 30 minutes, after which the samples were purified on a Qiagen MinElute PCR Purification column. The treated DNA was then passed through an Invitrogen Purelink column according to the manufacturer's instructions and eluted from the column in a volume of 50 μl.

The ligated, exonuclease-treated DNA was subjected to digestion by EcoRI. Reactions containing 50 μl of DNA, 30 μl of $H_2O$, 10 μl of EcoRI buffer, and 10 μl of EcoRI (20,000 units/ml) were incubated at 37° C. overnight. The cleaved products were purified using a Qiagen QiaQuick column according to the manufacturer's instructions. The cleaved products were ligated once more to generate closed circular DNA in reactions containing 50 μl of DNA, 20 μl of Buffer 4 (New England Biolabs), 2 μl of 100 mM ATP, 123 μl of $H_2O$, and 5 μl of ligase (as above). The ligation reactions were incubated at 25° C. for 15 minutes, after which they were subjected to another round of exonuclease treatment by adding to the mixture 1 μl of λ exonuclease (5,000 units/ml, NEB), 0.5 μl of Rec J (as above), 0.5 μl T7 exonuclease (as above), and 0.5 μl exonuclease I (as above). The exonuclease reactions were incubated at 37° C. for 30 minutes, after which the sample was purified with a Qiagen MinElute PCR Purification column.

The treated DNA was then subjected to Mme I digestion in a reaction mixture containing 10 μl of DNA, 78.75 μl of H2O, 10 μl of Buffer 4 (New England Biolabs), 0.25 μl of SAM, and 0.5 μl of Mme I (2,000 units/ml, NEB). The reactions were digested with Mme I for 60 minutes at 37° C., then purified on a Qiagen QiaQuick column that was buffered with a final concentration of 0.1% of 3 M sodium acetate. The column was washed with 700 μl of 8.0M guanidine HCl and the sample was added to the column according to the manufacturer's instructions. The DNA was eluted in 30 μl of EB buffer, and diluted to a final volume of 100 μl.

Streptavidin magnetic beads (50 μl) (Dynal Dynabeads M270, Invitrogen, Carlsbad, Calif., USA), were prepared by washing with 2× bead binding buffer and suspending the beads in 100 μl of 2× bead binding buffer, after which 100 μl of the DNA sample was added to the beads and mixed for 20 minutes at room temperature. The beads were washed twice in wash buffer. The SAD7 adaptor set (A/B set, wherein the single stranded oligonucleotides SAD7Ftop and SAD7Fbot are annealed to form the A adaptor, and the single stranded oligonucleotides SAD7Rtop and SADRFbot are annealed to form the B adaptor) (SAD7Ftop: 5'-CCGCCCAGCATCGC-CTCAGNN-3' (SEQ ID NO:51); SAD7Fbot: 5'-CTGAGGC-GATGCTGG-3' (SEQ ID NO:52); SAD7Rtop: 5'-CCGC-CCGAGCACCGCTCAGNN-3' (SEQ ID NO:53); SAD7Rbot: 5'-CTGAGCGGTGCTCGG-3' (SEQ ID NO:54), wherein N is any of the 4 bases A, G, T or C) was ligated to the DNA bound to the streptavidin beads, wherein a ligation reaction mix containing 15 μl of H2O, 25 μl of Quick Ligase buffer, 5 μl of the SAD7 adaptor set, and 5 μl of Quick Ligase (as above) was added to the bead-DNA mixture. The ligation reaction was incubated for 15 minutes at 25° C., and the beads were then washed twice with bead wash buffer.

A nucleotide fill-in reaction was performed by adding to the beads a mixture containing 40 μl H2O, 5 μl of 10× Fill-In buffer, 2 μl of 10 mM dNTPs, and 3 μl Fill-In polymerase (Bst DNA polymerase, 8,000 units/ml, NEB). The reaction was incubated at 37° C. for 20 minutes, and the beads washed twice in wash buffer. The beads were then suspended in 25 μl of TE buffer.

The DNA bound to beads were then subjected to PCR in reaction mixtures containing 30 µl of H2O, 5 µl 10× Advantage 2 Buffer, 2 µl of 10 mM dNTPs, 1 µl of 100 µM forward primer (SAD7FPCR: 5'-Bio-CCGCCCAGCATCGCC-3' (SEQ ID NO:55)), 1 µl of 100 µM reverse primer (SAD7RPCR: 5'-CCGCCCGAGCACCGC-3' (SEQ ID NO:56), 10 µl of DNA bound to beads, and 1 µl of Advantage 2 polymerase mix (Clontech, Mountain View, Calif., USA). PCR was carried out using the following program: (a) 4 minutes at 94° C., (b) 15 seconds at 94° C., (c) 15 seconds at 64° C., wherein steps (b) and (c) are carried out for 19 cycles, (d) 2 minutes at 68° C., after which the reactions were held at 14° C.

The PCR products were purified using a Qiagen MinElute PCR Purification column, and then the purified products were run on a 1.5% agarose gel at 5 volts per centimeter to detect the presence of a 120 bp product. The 120 bp fragment was excised from the gel and recovered using a Qiagen MinElute gel extraction protocol. The 120 bp fragment was eluted in 18 µl of EB buffer. The double-stranded products were bound to streptavidin beads and washed twice with bead wash buffer. The single stranded products were eluted in 125 mM NaOH, and purified on a Qiagen MinElute PCR purification column. This material was then sequenced using standard 454 Life Sciences Corporation (Branford, Conn., USA) sequencing methods on 454 Life Sciences Corporation automated sequencing systems.

Example 3

Protocol for the Non Hairpin Adaptor Paired End Sequencing

*E. Coli* K12 DNA (5 µg) at 100 µl volume was hydrosheared on speed 11 for 20 cycles using a standard assembly (HydroShear, as above). The sheared DNA was purified on a Qiagen MinElute PCR Purification column according to the manufacturer's instructions and eluted with 23 µl of EB buffer. The purified sheared DNA was subjected to blunt-end polishing in a reaction mixture containing 23 µl of DNA, 5 µl of 10× polishing buffer, 5 µl of 1 mg/ml bovine serum albumin, 5 µl of 10 mM ATP, 3 µl of 10 mM dNTPs, 5 µl of 10 U/µl T4 polynucleotide kinase, and 5 µl of 3 U/µl T4 DNA polymerase. The reactions were incubated for 15 minutes at 12° C., after which the temperature was raised to 25° C. for another 15 minutes. The reactions were subsequently purified on a Qiagen MinElute PCR Purification column according to the manufacturer's instructions. Ligation of the non-hairpin adaptor was carried out using 2 µg of the sheared, purified DNA in a reaction mixture containing 25 µl of 2× Quick Ligase buffer, 18.5 µl of 10 µM of the non-hairpin adaptor, and 2.5 µl of Quick Ligase (as above). The ligation reaction was incubated at 25° C. for 15 minutes, after which the sample was passed through a Sephacryl S-400 spin column, followed by a Qiagen MinElute PCR Purification column. The DNA was then eluted from the column with 10 µl of EB buffer.

The purified, ligated DNA was then subjected to a kinase reaction, wherein the mixture contained 13 µl of H2O, 25 µl of 2× buffer, 10 µl of DNA, and 2 µl of 10 U/µl T4 polynucleotide kinase. The reactions were incubated at 37° C. for 60 minutes, after which the samples were run on a 1% agarose gel at 5 volts per cm. Bands between 1500 and 4000 bp were excised from the gel and recovered using a Qiagen MinElute gel extraction protocol.

The purified DNA was subjected to another round of ligation to generate circular DNA in reaction mixtures containing 18 µl DNA, 20 µl of Buffer 4 (New England Biolabs), 2 µl of ATP, 150 µl of H2O, and 10 µl of ligase (as above). The reactions were incubated for 15 minutes at 25° C., after which a mixture containing 2 µl λ exonuclease (as above), 1 µl Rec J (as above), 1 µl of T7 exonuclease (as above) and 1 µl of exonuclease I (as above), and incubated for 30 minutes at 37° C. After the exonuclease reaction, the DNA was purified on a Qiagen MinElute PCR Purification column and eluted with 20 µl of EB buffer.

The purified ligated DNA was then added to a mixture containing 68.6 µl H2O, 10 µl of Buffer 4 (New England Biolabs), 0.2 µl of SAM, and 1 µl of Mme I restriction endonuclease (as above). The DNA was cleaved at 37° C. for 30 minutes, after which the DNA was purified using a Qiagen QiaQuick column that was pre-buffered at a final concentration of 0.1% of 3M sodium acetate and washed with 700 µl of 8.0M guanidine HCl. The purified DNA was then eluted with 30 µl of EB buffer and the volume adjusted to 100 µl.

Streptavidin magnetic beads (50 µl) (as above) were washed with 2× bead binding buffer and suspended in 100 µl of bead binding buffer. The beads were then mixed with 100 µl of the DNA sample and allowed to bind to each other for 20 minutes at room temperature. Thereafter, the beads were washed twice in wash buffer and subjected to a ligation reaction with the SAD7 adaptor set (A/B set) (as above). A mixture containing 15 µl H2O, 25 µl of Quick Ligase buffer, 5 µl of SAD7 adaptor, and 5 µl Quick Ligase (as above) were added to the DNA bound to beads, and incubated for 15 minutes at 25° C., after which the beads were washed twice in wash buffer.

The DNA bound to beads were subjected to a fill-in reaction in a mixture containing 40 µl of H2O, 5 µl of 10× Fill-in buffer, 2 µl of 10 mM dNTPs, and 3 µl of Fill-in polymerase (as above). The reaction took place for 20 minutes at 37° C., after which the beads were washed twice in wash buffer and suspended in 25 µl of TE buffer. The DNA bound to beads was amplified in a reaction mixture containing 30 µl H2O, 5 µl of 10× Advantage 2 buffer, 2 µl of dNTPs, 0.5 µl of 100 µM forward primer (as above), 0.5 µl of 100 µM reverse primer (as above), 10 µl of DNA bound to beads, and 1 µl of Advantage 2 enzyme (as above). The PCR reaction took place under the following conditions: (a) 4 minutes at 94° C., (b) 15 seconds at 94° C., (c) 15 seconds at 64° C., wherein steps (b) and (c) were repeated for 24 cycles, (d) 2 minutes at 68° C., after which the PCR reaction was held at 14° C. The PCR products were purified on a Qiagen MinElute PCR Purification column and run on a 1.5% agarose gel at 5 volts per cm. A product of 120 bp was excised from the gel and recovered with the Qiagen MinElute gel extraction protocol. The DNA was subsequently eluted in 18 µl of EB buffer.

The double-stranded DNA was bound to streptavidin beads and the beads were washed twice with wash buffer. The single-stranded DNA was then eluted with 125 mM NaOH and subsequently purified using a Qiagen MinElute PCR purification column. The purified material was subjected to a standard 454 emulsion and sequencing protocol.

Using the procedure described above, we achieved the following results:

*E. coli* contigs were produced from normal 454 sequences from four 60×60 runs (approximately 1.3 million reads): 303 contigs of greater than 1000 bp were produced, which had an average size of 16,858 bp and a maximum size of 94,060 bp. Table 3 contains additional results achieved using the above procedure.

TABLE 3

Results from paired-end sequencing procedures

| Paired Reads | Region | Adaptor Set | Total Set of Oriented Contigs | Average Size of Ordered Set of Contigs | Largest Ordered Set of Contigs |
|---|---|---|---|---|---|
| 19,605 | One 14 × 43 | Hairpin | 15 | 308,129 bp | 2,989,419 bp |
| 71,822 | Multiple 14 × 43 | Hairpin | 11 | 420,302 bp | 3,330,963 bp |
| 20,571 | Two 14 × 43 | Overhang | 19 | 243,197 bp | 1,512,859 bp |

The analysis was performed by first blasting all paired reads to the *E. coli* K12 genome acquired from Genbank. Reads that matched to the reference genome with an expected value of less than 0.1 were kept. All reads that contained two separate blast hits separated by the internal linker sequence were analyzed for their blasted distance apart in the genome and only kept if the distance was less than 5,000 bp. These reads were then ordered by first and second position hit in the genome and tested to see if overlapping occurred to the next sorted paired sequence. Each of these ordered contigs was then tested for overlapping partners to the 454 sequencing contigs in the same manner as above.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention. Modifications and variations of the methods described herein will be obvious to those skilled in the art and are intended to be encompassed by the following claims.

We claim:

1. A method for obtaining a DNA construct comprising two end regions of a target nucleic acid comprising the steps of:
    (a) fragmenting a large nucleic acid molecule to produce a target nucleic acid;
    (b) ligating a hairpin adaptor to each end of said target nucleic acids from step (a), digesting with exonuclease to remove nucleic acids with exposed 5' or 3' ends and cleaving said hairpin adaptors to create sticky ends for circularization;
    (c) ligating a signature tag to said sticky ends to form a circular nucleic acid molecule;
    (d) digesting said circular nucleic acid with a restriction endonucleases which cuts said target nucleic acid but which does not cut said hairpin adaptor or said signature tag to produce said DNA construct comprising two end regions of a target nucleic acid;
    (e) ligating a PCR primer to each end of said DNA construct; and
    (f) amplifying said DNA construct by PCR.

2. The method of claim 1 wherein said restriction endonucleases is a type I or type IIS restriction endonucleases.

3. The method of claim 1 wherein said target nucleic acid is at least 50 kb, at least 20 kb, at least 10 kb or at least 5 kb.

4. The method of claim 1 wherein said target nucleic acid is between 50 kb and 3 kb, between 20 and 3 kb, or between 10 kb and 3 kb.

5. The method of claim 1 wherein said signature tag comprises a marker gene or an origin of replication.

6. The method of claim 1 wherein said hairpin adaptors or said signature tag is biotinylated.

7. The method of claim 6 further comprising the step of isolating nucleic acid fragments comprising a signature tag or hairpin adaptors after said digesting step.

8. A method for obtaining a DNA construct comprising two end regions of a target nucleic acid comprising the steps of:
    (a) fragmenting a large nucleic acid molecule to produce a target nucleic acid;
    (b) ligating a first hairpin adaptor to one end of said target nucleic acid and a second hairpin adaptor to a second end of said target nucleic acid to form an adaptor tagged target nucleic acid, wherein the first and second hairpin adaptors comprise a hairpin element and at least one hairpin adaptor is biotinylated;
    (c) cleaving the hairpin element from the first and second hairpin adaptors of the adaptor tagged nucleic acid producing a cleaved end on the first and second hairpin adaptor;
    (d) circularizing said adaptor tagged target nucleic acid by ligating the cleaved end of said first hairpin adaptor to the cleaved end of said second hairpin adaptor to form a circular nucleic acid molecule comprising a target nucleic acid region and an adaptor region;
    (e) fragmenting said circular nucleic acid molecule to produce at least one said DNA construct comprising two end regions of a target nucleic acid with a ligated adaptor region therebetween; and
    (f) enriching for said DNA construct by affinity purification with an avidin or streptavidin coated solid support.

9. The method of claim 8 wherein said large nucleic acid or said target nucleic acid is methylated with a methylase before step (b).

10. The method of claim 9 wherein the methylation prevents restriction endonuclease cleavage of the target nucleic acid by one or more restriction endonucleases.

11. The method of claim 8 further comprising the following steps after step (b):
    (b1) treating said adaptor tagged target nucleic acid with an exonuclease to digest any target nucleic acids not ligated to hairpin adaptors at both ends;
    (b2) removing said exonuclease from said adaptor tagged target nucleic acid.

12. The method of claim 8 wherein cleaving the hairpin elements comprises digesting said adaptor tagged target nucleic acid with a restriction endonucleases which cleaves said first and second hairpin adaptors and which does not cleave said target nucleic acid to generate an adaptor tagged target nucleic acid with the cleaved ends.

13. The method of claim 8 further comprising a step of removing uncircularized target nucleic acid after step (d).

14. The method of claim 13 wherein removing the uncircularized target nucleic acid comprises contacting said target nucleic acid with exonuclease.

15. The method of claim 8 wherein step (e) is performed by mechanical shearing.

16. The method of claim 8 wherein said target nucleic acid is at least 50 kb, at least 20 kb, at least 10 kb or at least 5 kb.

17. The method of claim 8 wherein said target nucleic acid is between 50 kb and 3 kb, between 20 and 3 kb, or between 10 kb and 3 kb.

18. The method of claim 8 wherein said target nucleic acid is between at least 500 bp to 1 kb, between 1 kb and 3 kb or between 500 bp and 3 kb.

19. The method of claim 8 wherein said DNA construct comprising two end regions of a target nucleic acid is less than 10 kb in size.

20. The method of claim 8 wherein said DNA construct comprising two end regions of a target nucleic acid is less than 20 kb in size.

21. The method of claim 8 wherein said DNA construct comprising two end regions of a target nucleic acid is less than 40 kb in size.

22. The method of claim 8 wherein said DNA construct comprising two end regions of a target nucleic acid is less than 5 kb in size.

23. The method of claim 8 wherein said DNA construct comprising two end regions of a target nucleic acid is less than 3 kb in size.

24. The method of claim 8 wherein said DNA construct comprising two end regions of a target nucleic acid is less than 1 kb in size.

25. The method of claim 8 wherein said DNA construct comprising two end regions of a target nucleic acid is less than 500 bp in size.

26. The method of claim 8 wherein said DNA construct comprising two end regions of a target nucleic acid is less than 300 bp in size.

27. A method for obtaining a DNA construct comprising two end regions of a target nucleic acid comprising the steps of:
    (a) fragmenting a large nucleic acid molecule to produce a target nucleic acid;
    (b) ligating a hairpin adaptor to each end of said target nucleic acids from step (a), digesting with exonuclease to remove nucleic acids with exposed 5' or 3' ends and cleaving said hairpin adaptors to create sticky ends for circularization;
    (c) ligating a capture element to said target nucleic acid to form a circular nucleic acid molecule, wherein said capture element is a nucleic acid comprising one member of a binding pair;
    (d) digesting said circular nucleic acid with a restriction endonuclease which cuts said target nucleic acid but which does not cut said capture element to produce said DNA construct comprising two end regions of a target nucleic acid separated by said capture element; and
    (e) enriching for said DNA construct by affinity purification using a solid support comprising a second member of said binding pair.

28. The method of claim 27 wherein said binding pair is selected from the group consisting of FLAG/anti FLAG antibody, biotin/avidin, and biotin/streptavidin.

29. The method of claim 27 wherein said capture element is biotinylated.

30. The method of claim 27 further comprising a step of removing uncircularized target nucleic acid after step (c).

31. The method of claim 30 wherein removing the uncircularized target nucleic acid comprises contacting said target nucleic acid with an exonuclease.

32. The method of claim 27 wherein said target nucleic acid is at least 50 kb, at least 20 kb, at least 10 kb or at least 5 kb.

33. The method of claim 27 wherein said target nucleic acid is between 50 kb and 3 kb, between 20 and 3 kb, or between 10 kb and 3 kb.

34. The method of claim 27 wherein said DNA construct comprising two end regions of a target nucleic acid is less than 5 kb in size.

35. The method of claim 27 wherein said DNA construct comprising two end regions of a target nucleic acid is less than 3 kb in size.

36. The method of claim 27 wherein said DNA construct comprising two end regions of a target nucleic acid is less than 1 kb in size.

37. The method of claim 27 wherein said DNA construct comprising two end regions of a target nucleic acid is less than 500 bp in size.

38. The method of claim 27 wherein said DNA construct comprising two end regions of a target nucleic acid is less than 300 bp in size.

39. The method of claim 27 wherein said target nucleic acid is between at least 500 bp to 1 kb, between 1 kb and 3 kb or between 500 bp and 3 kb.

40. The method of claim 27 wherein said DNA construct comprising two end regions of a target nucleic acid is less than 10 kb in size.

41. The method of claim 27 wherein said DNA construct comprising two end regions of a target nucleic acid is less than 20 kb in size.

42. The method of claim 27 wherein said DNA construct comprising two end regions of a target nucleic acid is less than 40 kb in size.

43. The method of claim 8 wherein in step (de), said circular nucleic acid molecule is fragmented by digestion with a restriction endonucleases.

44. The method of any one of claims 2, 27 or 43, wherein the restriction endonucleases is MmeI.

45. The method of claim 44, wherein a carrier DNA containing MmeI restriction sites is added during the MmeI digestion.

46. The method of claim 45, wherein the amount of carrier DNA is added in molar excess of the circular nucleic acid.

47. The method of claim 45, wherein MmeI enzyme and MmeI sites in the carrier DNA are present in stoichiometric amounts.

48. The method of claim 12 wherein the hairpin adaptors have at least one deoxyinosine in each strand of their double-stranded regions, and wherein the endonucleases is Endonuclease V.

49. A method for obtaining a DNA construct comprising two end regions of a target nucleic acid comprising the steps of:
    (a) fragmenting a large nucleic acid molecule to produce a target nucleic acid, wherein said large nucleic acid or said target nucleic acid is methylated with a methylase;
    (b) ligating a first adaptor comprising a hairpin to one end of said target nucleic acid and a second adaptor comprising a hairpin to a second end of said target nucleic acid to form an adaptor tagged target nucleic acid;
    (b1) treating said adaptor tagged target nucleic acid with an exonuclease to digest any target nucleic acids not ligated to the hairpin adaptors at both ends;
    (b2) removing said exonuclease from said adaptor tagged target nucleic acid;
    (b3) digesting said adaptor tagged target nucleic acid with a restriction endonuclease which cleaves the hairpins from said first and second adaptors and which does not cleave said target nucleic acid to generate an adaptor tagged target nucleic acid with cleaved adaptors at both ends;
    (c) circularizing said adaptor tagged target nucleic acid by ligating said first adaptor to said second adaptor to form a circular nucleic acid molecule comprising a target nucleic acid region and an adaptor region; and (d) fragmenting said circular nucleic acid molecule at the target nucleic acid region to produce said DNA construct comprising two end regions of a target nucleic acid.

50. The method of claim 49, wherein at least one of said first or second adaptor is biotinylated.

51. The method of claim 49, further comprising the step of purifying said adaptor tagged target nucleic acid by affinity purification with an avidin or streptavidin coated solid support after step (d).

52. The method of claim 49, wherein at least one of said first or second adaptor additionally comprises a Type IIs restriction site and the fragmenting in step (d) is accomplished with a Type IIs restriction enzyme.

53. The method of claim 49, wherein the fragmenting in step (d) is accomplished with mechanical shearing.

* * * * *